United States Patent
Willot et al.

(10) Patent No.: US 11,926,623 B2
(45) Date of Patent: Mar. 12, 2024

(54) HETEROCYCLE DERIVATIVES AS PESTICIDES

(71) Applicant: Bayer Aktiengesellschaft, Leverkusen (DE)

(72) Inventors: Matthieu Willot, Duesseldorf (DE); Rüdiger Fischer, Pulheim (DE); Dominik Hager, Monheim (DE); Laura Hoffmeister, Duesseldorf (DE); David Wilcke, Duesseldorf (DE); Kerstin Ilg, Cologne (DE); Ulrich Goergens, Ratingen (DE)

(73) Assignee: Bayer Aktiengesellschaft, Leverkusen (DE)

(*) Notice: Subject to any disclaimer, the term of this patent is extended or adjusted under 35 U.S.C. 154(b) by 693 days.

(21) Appl. No.: 17/255,830

(22) PCT Filed: Jun. 19, 2019

(86) PCT No.: PCT/EP2019/066187
§ 371 (c)(1),
(2) Date: Dec. 23, 2020

(87) PCT Pub. No.: WO2020/002082
PCT Pub. Date: Jan. 2, 2020

(65) Prior Publication Data
US 2021/0139480 A1    May 13, 2021

(30) Foreign Application Priority Data

Jun. 26, 2018 (EP) .................................. 18179885

(51) Int. Cl.
| C07D 471/04 | (2006.01) |
| A01N 25/30 | (2006.01) |
| A01N 43/52 | (2006.01) |
| A01N 43/56 | (2006.01) |
| A01N 43/80 | (2006.01) |
| A01N 43/84 | (2006.01) |
| A01N 43/90 | (2006.01) |

(52) U.S. Cl.
CPC .......... *C07D 471/04* (2013.01); *A01N 25/30* (2013.01); *A01N 43/52* (2013.01); *A01N 43/56* (2013.01); *A01N 43/80* (2013.01); *A01N 43/84* (2013.01); *A01N 43/90* (2013.01)

(58) Field of Classification Search
CPC ...... C07D 471/04; A01N 25/30; A01N 43/52; A01N 43/56; A01N 43/80; A01N 43/84; A01N 43/90
See application file for complete search history.

(56) References Cited

U.S. PATENT DOCUMENTS

| 10,087,192 B2 | 10/2018 | Fischer et al. |
| 10,364,243 B2 | 7/2019 | Fischer et al. |
| 10,654,845 B2 | 5/2020 | Fischer et al. |
| 2019/0241564 A1 | 8/2019 | Fischer et al. |
| 2020/0045976 A1 | 2/2020 | Wilcke et al. |
| 2020/0054017 A1 | 2/2020 | Wilcke et al. |

FOREIGN PATENT DOCUMENTS

| CN | 102414195 A | 4/2012 | |
| CN | 104334552 A | 2/2015 | |
| EP | 2857396 A1 | 4/2015 | |
| JP | 2018024658 A | 2/2018 | |
| TW | 201819374 A | 6/2018 | |
| WO | WO-2004005264 A2 * | 1/2004 | ........... C07D 233/64 |
| WO | 2010125985 A1 | 11/2010 | |
| WO | 2012/074135 A1 | 6/2012 | |
| WO | 2012/086848 A1 | 6/2012 | |
| WO | 2013/018928 A1 | 2/2013 | |
| WO | 2013033901 A1 | 3/2013 | |
| WO | 2013034047 A1 | 3/2013 | |
| WO | 2013162715 A1 | 10/2013 | |
| WO | 2013/180193 A1 | 12/2013 | |
| WO | 2013/191113 A1 | 12/2013 | |
| WO | 2014/142292 A1 | 9/2014 | |
| WO | 2014/148451 A1 | 9/2014 | |
| WO | 2015/000715 A1 | 1/2015 | |
| WO | 2015/002211 A1 | 1/2015 | |
| WO | 2015000715 A1 | 1/2015 | |

(Continued)

OTHER PUBLICATIONS

PCT International Search Report for PCT/EP2019/066187, dated Aug. 19, 2019.

Donohoe, T.J., et al. "Direct preparation of thiazoles, imidazoles, imidazopyridines and thiazolidines from alkenes," Org. Biomol. Chem., (2012), vol. 10, issue 5: 1093-1101.

Robertson, D.W., et al. "Imidazole-pyridine bioisosterism: comparison of the inotropic activities of pyridine- and midazole-substituted 6-phenyldihydropyridazinone cardiotonics," Journal of Medicinal Chemistry, (1988), vol. 31, issue 2: 461-465.

*Primary Examiner* — John M Mauro
(74) *Attorney, Agent, or Firm* — McBee Moore & Vanik, IP, LLC

(57) ABSTRACT

The invention relates to novel compounds of the formula (I)

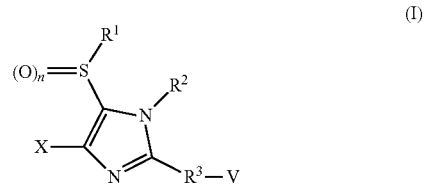

in which X, $R^1$, $R^2$, $R^3$, V and n have the meanings given above, to the use thereof as acaricides and/or insecticides for controlling animal pests and to methods and intermediates for the preparation thereof.

10 Claims, No Drawings

(56) References Cited

FOREIGN PATENT DOCUMENTS

| | | |
|---|---|---|
| WO | 2015/071180 A1 | 5/2015 |
| WO | 2015/091945 A1 | 6/2015 |
| WO | 2015/121136 A1 | 8/2015 |
| WO | 2015/133603 A1 | 9/2015 |
| WO | 2015/198817 A1 | 12/2015 |
| WO | 2015/198859 A1 | 12/2015 |
| WO | 2016/005263 A1 | 1/2016 |
| WO | 2016/020286 A1 | 2/2016 |
| WO | 2016/023954 A2 | 2/2016 |
| WO | 2016/026848 A1 | 2/2016 |
| WO | 2016/039441 A1 | 3/2016 |
| WO | 2016/039444 A1 | 3/2016 |
| WO | 2016/041819 A1 | 3/2016 |
| WO | 2016/046071 A1 | 3/2016 |
| WO | 2016039444 A1 | 3/2016 |
| WO | 2016/058928 A1 | 4/2016 |
| WO | 2016/059145 A1 | 4/2016 |
| WO | 2016/071214 A1 | 5/2016 |
| WO | 2016/091731 A1 | 6/2016 |
| WO | 2016/096584 A1 | 6/2016 |
| WO | 2016/107742 A1 | 7/2016 |
| WO | 2016/107831 A1 | 7/2016 |
| WO | 2016/113155 A1 | 7/2016 |
| WO | 2016/116338 A1 | 7/2016 |
| WO | 2016113155 A1 | 7/2016 |
| WO | 2016/121997 A1 | 8/2016 |
| WO | 2016/124557 A1 | 8/2016 |
| WO | 2016/124563 A1 | 8/2016 |
| WO | 2016/125621 A1 | 8/2016 |
| WO | 2016/125622 A1 | 8/2016 |
| WO | 2016/129684 A1 | 8/2016 |
| WO | 2016/142326 A1 | 9/2016 |
| WO | 2016/142327 A1 | 9/2016 |
| WO | 2016/169882 A1 | 10/2016 |
| WO | 2016/169886 A1 | 10/2016 |
| WO | 2016169886 A1 | 10/2016 |
| WO | 2017055185 A1 | 4/2017 |
| WO | 2017061497 A1 | 4/2017 |
| WO | 2018130437 A1 | 7/2018 |
| WO | 2018130443 A1 | 7/2018 |

\* cited by examiner

HETEROCYCLE DERIVATIVES AS PESTICIDES

CROSS-REFERENCE TO RELATED APPLICATIONS

This application is the National Stage entry of International Application No. PCT/EP2019/066187, filed 19 Jun. 2019, which claims priority to European Patent Application No. 18179885.1, filed 26 Jun. 2018.

BACKGROUND

Field

The present invention relates to heterocycle derivatives of the formula (I), to their use as acaricides and/or insecticides for controlling animal pests, particularly arthropods and especially insects and arachnids, and to methods and intermediates for their preparation.

DESCRIPTION OF RELATED ART

Heterocycle derivatives with insecticidal properties are already described in the literature, e.g. in WO 2010/125985, WO 2012/074135, WO 2012/086848, WO 2013/018928, WO 2013/180193, WO 2013/191113, WO 2014/142292, WO 2014/148451, WO 2015/000715, WO 2016/124563, WO 2016/124557, WO 2015/121136, WO 2015/133603, WO 2015/198859, WO 2015/002211, WO 2015/071180, WO 2015/091945, WO 2016/005263, WO 2016/039441, WO 2015/198817, WO 2016/041819, WO 2016/039441, WO 2016/039444, WO 2016/026848, WO 2016/023954, WO 2016/020286, WO 2016/046071, WO 2016/058928, WO 2016/059145, WO 2016/071214, WO 2016/091731, WO 2016/096584, WO 2016/107742, WO 2016/107831, WO 2016/113155, WO 2016/116338, WO 2016/121997, WO 2016/125621, WO 2016/125622, WO 2016/129684, WO 2016/142326, WO 2016/142327, WO 2016/169882, WO 2016/169886, WO 2018/130437 and WO 2018/130443.

Modern crop protection compositions have to meet many demands, for example in relation to extent, persistence and spectrum of their action and possible use. Questions of toxicity, sparing of beneficial species and pollinators, environmental properties, application rates, combinability with other active compounds or formulation auxiliaries play a role, as does the question of the complexity involved in the synthesis of an active compound, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

It was an object of the present invention to provide compounds which broaden the spectrum of the pesticides in various aspects and/or improve their activity.

Novel heterocycle derivatives have now been found, these having advantages over the compounds already known, examples of which include better biological or environmental properties, a wider range of application methods, better insecticidal or acaricidal action, and good compatibility with useful plants. The heterocycle derivatives can be used in combination with further compositions for improving efficacy, especially against insects that are difficult to control.

The subject matter of the present invention is therefore novel compounds of the formula (I)

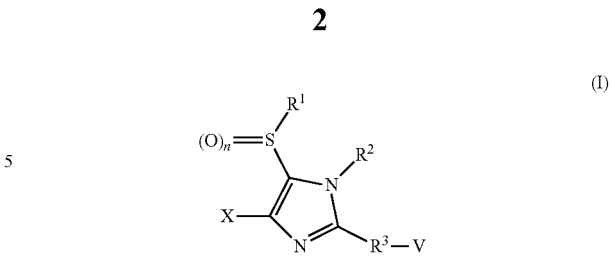

in which (configuration 1-1)
$R^1$ represents $(C_1-C_6)$alkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl or $(C_3-C_8)$cycloalkyl, $R^2$ represents hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, cyano$(C_3-C_8)$cycloalkyl, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl or $(C_1-C_6)$haloalkoxycarbonyl-$(C_1-C_6)$alkyl, $R^3$ represents aryl which is optionally mono- or polysubstituted by identical or different substituents or represents a saturated, partially saturated or heteroaromatic ring which is optionally mono- or polysubstituted by identical or different substituents, where at least one carbon atom is replaced by a heteroatom, which may in each case contain at least one carbonyl group and/or where possible substituents are in each case as follows: cyano, carboxyl, halogen, nitro, acetyl, hydroxy, amino, SCN, tri-$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkoxyimino, —N=C(H)—O$(C_1-C_6)$alkyl, —C(H)=N—O$(C_1-C_6)$alkyl, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkyl-aminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, V represents $(C_3-C_6)$cycloalkyl or aryl which are in each case optionally mono- or polysubstituted by identical or different substituents or represents a saturated, partially saturated or heteroaromatic ring which is optionally mono- or polysubstituted by identical or different substituents, where at least one carbon atom is replaced by a heteroatom, which may in each case contain at least one carbonyl group and/or where possible substituents are in each case as follows: cyano, carboxyl, halogen, nitro, acetyl, hydroxy, amino, SCN, tri-$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_6)$alkoxy, $(C_1-C_6)$haloalkoxy, $(C_1-C_6)$cyanoalkoxy, $(C_1-C_6)$alkoxy carbonyl-$(C_1-C_6)$alkoxy, $(C_1-C_6)$alkoxy-$(C_1-C_6)$alkoxy, $(C_1-C_6)$alkoxyimino, —N=C(H)—O$(C_1-C_6)$alkyl, —C(H)=N—O$(C_1-C_6)$alkyl, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkyl-aminocarbonyl, $(C_2-C_6)$alkenylaminocarbonyl, di-$(C_2-C_6)$-alkenylaminocarbonyl, $(C_3-C_5)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, X represents a heteroaromatic 9-membered fused bicyclic ring system from the series Q1 to Q6,

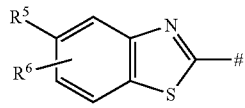

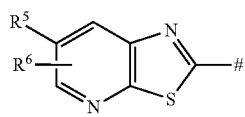

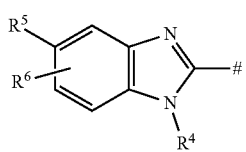

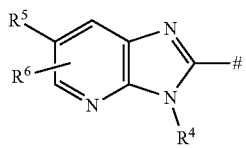

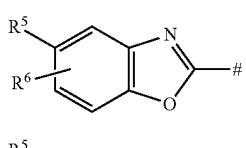

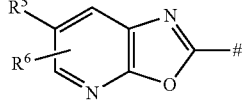

$R^4$ represents hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$haloalkynyl or $(C_3-C_5)$cycloalkyl, $R^5$, $R^6$ independently of one another represent hydrogen, cyano, halogen, $(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl, $(C_3-C_8)$cycloalkyl, $(C_3-C_5)$cycloalkyl-$(C_3-C_5)$cycloalkyl, $(C_1-C_6)$alkyl-$(C_3-C_5)$cycloalkyl, $(C_1-C_6)$haloalkyl-$(C_3-C_5)$cycloalkyl, cyano-$(C_3-C_5)$cycloalkyl, halo$(C_3-C_5)$cycloalkyl, $(C_1-C_6)$alkoxy, $(C_1-C_6)$haloalkoxy, $(C_1-C_6)$alkoxyimino, $(C_1-C_6)$haloalkoxyimino, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, $(C_1-C_6)$alkylsulfonyloxy, $(C_1-C_6)$haloalkylsulfonyloxy, $(C_1-C_6)$alkylcarbonyl, $(C_1-C_6)$haloalkylcarbonyl, aminocarbonyl, $(C_1-C_6)$alkylaminocarbonyl, di$(C_1-C_6)$alkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl or di$(C_1-C_6)$alkylaminosulfonyl, n represents 0, 1 or 2.

DETAILED DESCRIPTION OF A PREFERRED EMBODIMENT

It has additionally been found that the compounds of the formula (I) have very good efficacy as pesticides, preferably as insecticides and/or acaricides, and additionally generally have very good plant compatibility, in particular with respect to crop plants.

The compounds according to the invention are defined in general terms by the formula (I). Preferred substituents or ranges of the radicals given in the formulae mentioned above and below are illustrated hereinafter:

Configuration 2-1

$R^1$ preferably represents $(C_1-C_4)$alkyl, $(C_1-C_4)$cyanoalkyl, $(C_1-C_4)$alkoxy-$(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl or $(C_3-C_6)$cycloalkyl, $R^2$ preferably represents hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, cyano$(C_3-C_6)$cycloalkyl, $(C_1-C_4)$alkylthio-$(C_1-C_4)$alkyl, $(C_1-C_4)$haloalkylthio-$(C_1-C_4)$alkyl, $(C_1-C_4)$alkylsulfinyl-$(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl or $(C_1-C_4)$haloalkylsulfonyl-$(C_1-C_4)$alkyl, $R^3$ preferably represents aryl which is optionally mono- or disubstituted by identical or different substituents or represents a saturated, partially saturated or heteroaromatic ring which is optionally mono- or disubstituted by identical or different substituents, where at least one carbon atom is replaced by a heteroatom from the group consisting of N, O and S, which may in each case contain at least one carbonyl group and/or where possible substituents are in each case as follows: cyano, halogen, nitro, acetyl, amino, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkoxyimino, —N=C(H)—O$(C_1-C_4)$alkyl, —C(H)=N—O$(C_1-C_4)$alkyl, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, amino sulfonyl, $(C_1-C_4)$alkylaminosulfonyl, di$(C_1-C_4)$alkylaminosulfonyl, $(C_1-C_4)$alkylcarbonylamino, V preferably represents $(C_3-C_6)$cycloalkyl or aryl which are in each case optionally mono- or disubstituted by identical or different substituents or represents a saturated, partially saturated or heteroaromatic ring which is optionally mono- or disubstituted by identical or different substituents, where at least one carbon atom is replaced by a heteroatom from the group consisting of N, O and S, which may in each case contain at least one carbonyl group and/or where possible substituents are in each case as follows: cyano, halogen, nitro, acetyl, amino, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkoxyimino, —N=C(H)—O$(C_1-C_4)$alkyl, —C(H)=N—O$(C_1-C_4)$alkyl, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, aminosulfonyl, $(C_1-C_4)$alkylaminosulfonyl, di$(C_1-C_4)$alkylaminosulfonyl, $(C_1-C_4)$alkylcarbonylamino, X preferably represents a heteroaromatic 9-membered fused bicyclic ring system from the series Q1 to Q6, $R^4$ preferably represents hydrogen, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$haloalkenyl, $(C_2-C_4)$alkynyl, $(C_2-C_4)$haloalkynyl or $(C_3-C_6)$cycloalkyl, $R^5$, $R^6$ independently of one another preferably represent hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, cyano$(C_3-C_6)$cycloalkyl, halo$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, n preferably represents 0, 1 or 2.

Configuration 3-1

$R^1$ particularly preferably represents $(C_1-C_4)$alkyl, $(C_1-C_4)$haloalkyl, $(C_2-C_4)$alkenyl, $(C_2-C_4)$haloalkenyl or $(C_3-C_6)$cycloalkyl, $R^2$ particularly preferably represents hydrogen, $(C_1-C_4)$alkyl, $(C_1-C_4)$haloalkyl, $(C_3-C_6)$cycloalkyl or halo$(C_3-C_6)$cycloalkyl, $R^3$—V particularly preferably represents a 5- or 6-membered ring optionally mono- or disubstituted by identical or different substituents from the series U-1 to U-83, where possible substituents are in each case: cyano, halogen, $(C_1-C_4)$alkyl, $(C_1-C_4)$alkoxy or $(C_1-C_4)$haloalkoxy,

U-1

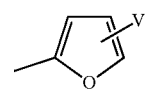
U-2

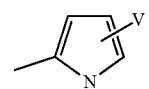
U-3

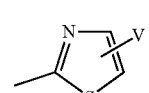
U-4

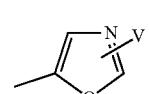
U-5

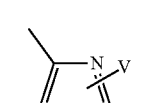
U-6

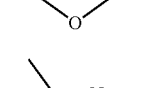
U-7

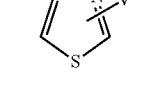
U-8

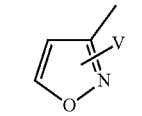
U-9

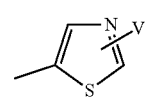
U-10

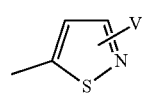 U-11
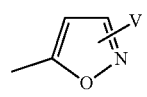 U-12
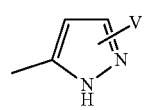 U-13
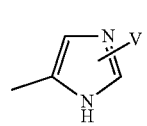 U-14
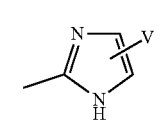 U-15
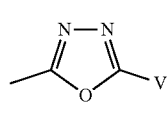 U-16
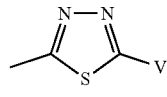 U-17
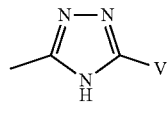 U-18
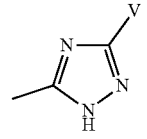 U-19
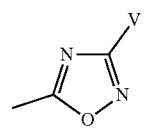 U-20
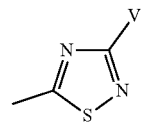 U-21
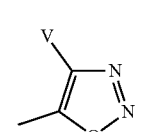 U-22
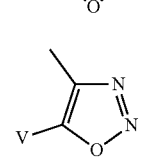 U-23
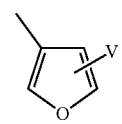 U-24
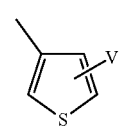 U-25
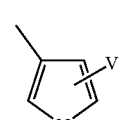 U-26
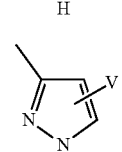 U-27
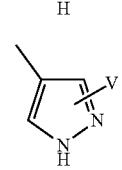 U-28
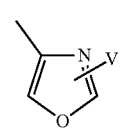 U-29
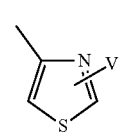 U-30
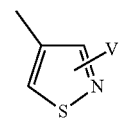 U-31
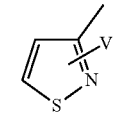 U-32
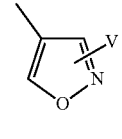 U-33
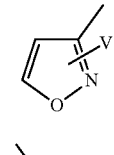 U-34
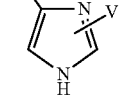 U-35

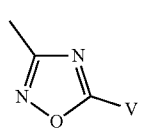 U-36
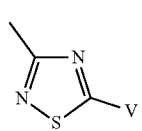 U-37
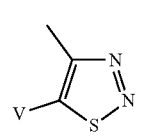 U-38
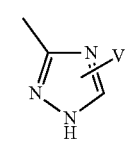 U-39
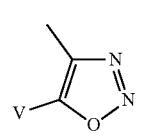 U-40
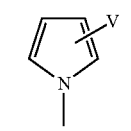 U-41
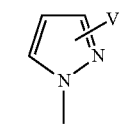 U-42
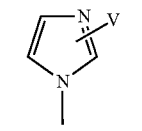 U-43
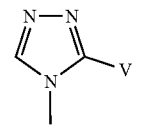 U-44
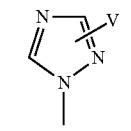 U-45
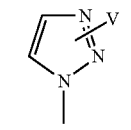 U-46
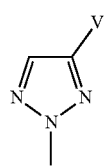 U-47
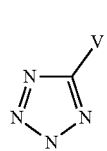 U-48
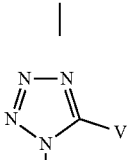 U-49
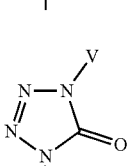 U-50
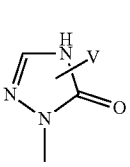 U-51
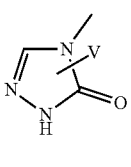 U-52
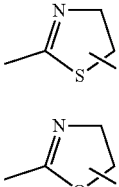 U-53
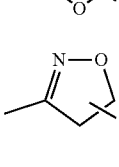 U-54
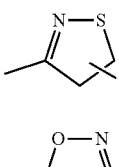 U-55
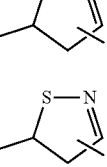 U-56
 U-57
 U-58

-continued
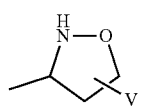 U-59
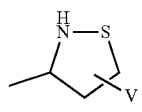 U-60
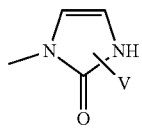 U-61
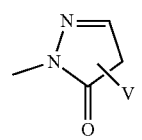 U-62
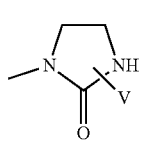 U-63
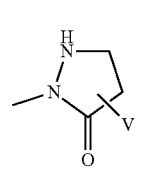 U-64
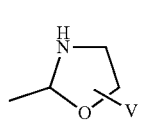 U-65
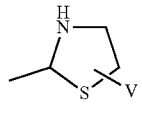 U-66
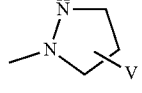 U-67
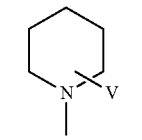 U-68
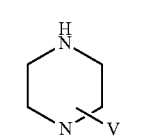 U-69
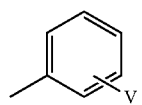 U-70
-continued
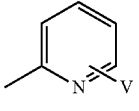 U-71
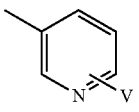 U-72
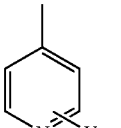 U-73
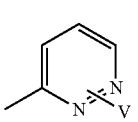 U-74
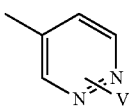 U-75
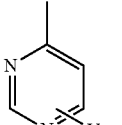 U-76
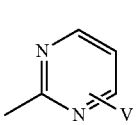 U-77
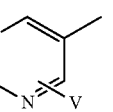 U-78
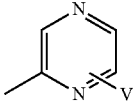 U-79
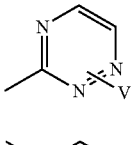 U-80
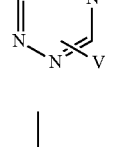 U-81
U-82

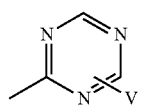
U-83
where
V particularly preferably represents a 3- to 6-membered ring optionally mono- or disubstituted by identical or different substituents from the series V-1 to V-105, where possible substituents are in each case: cyano, halogen, $(C_1-C_4)$alkyl, $(C_1-C_4)$alkoxy or $(C_1-C_4)$haloalkoxy,
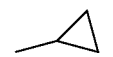
V-1
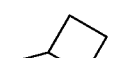
V-2
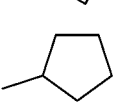
V-3
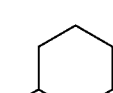
V-4
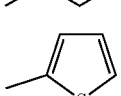
V-5
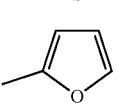
V-6
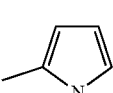
V-7
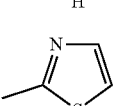
V-8
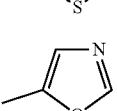
V-9
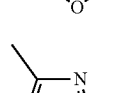
V-10
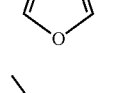
V-11
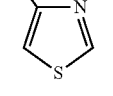
V-12
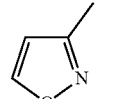
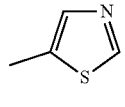
V-13
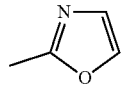
V-14
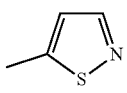
V-15
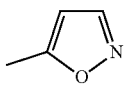
V-16
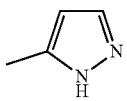
V-17
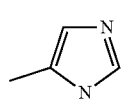
V-18
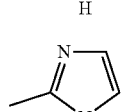
V-19
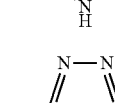
V-20
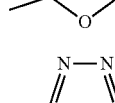
V-21
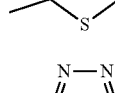
V-22
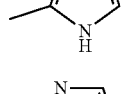
V-23
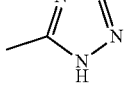
V-24
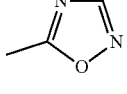
V-25
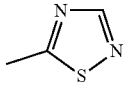
V-26
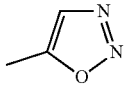
V-27

-continued
V-28 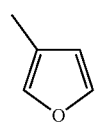
V-29 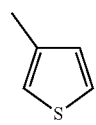
V-30 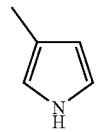
V-31 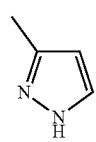
V-32 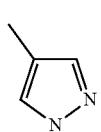
V-33 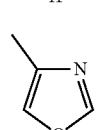
V-34 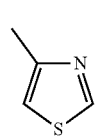
V-35 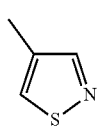
V-36 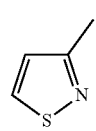
V-37 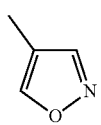
V-38 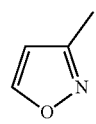
V-39 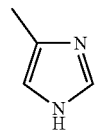
-continued
V-40 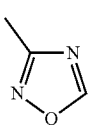
V-41 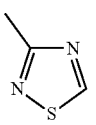
V-42 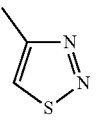
V-43 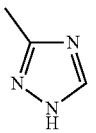
V-44 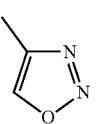
V-45 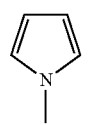
V-46 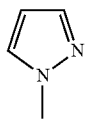
V-47 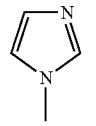
V-48 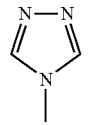
V-49 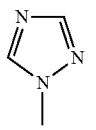
V-50 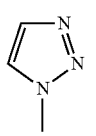
V-51 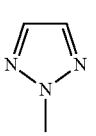

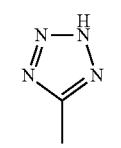 V-40
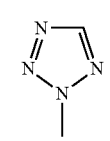 V-41
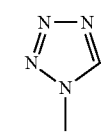 V-42
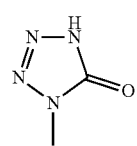 V-43
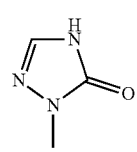 V-44
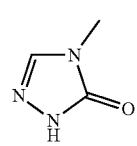 V-45
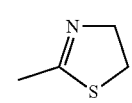 V-46
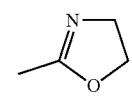 V-47
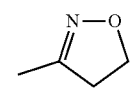 V-48
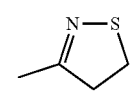 V-49
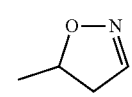 V-50
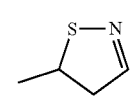 V-51
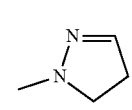 V-52
V-53
V-54
V-55
V-56
V-57
V-58
V-59
V-60
V-61
V-62
V-63
V-64
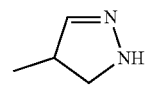 V-65
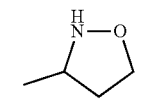 V-66
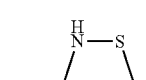 V-67
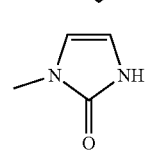 V-68
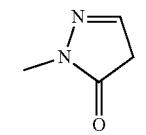 V-69
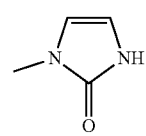 V-70
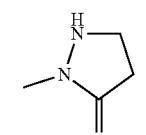 V-71
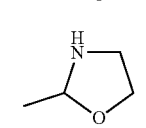 V-72
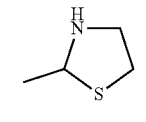 V-73
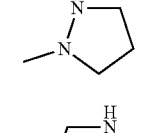 V-74
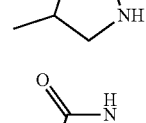 V-75
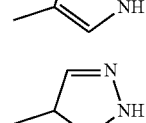 V-76
V-77

-continued
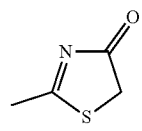 V-78
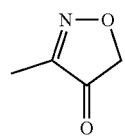 V-79
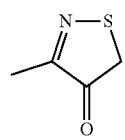 V-80
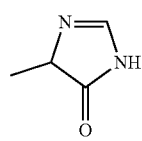 V-81
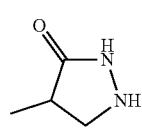 V-82
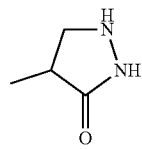 V-83
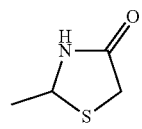 V-84
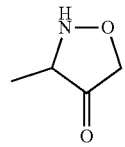 V-85
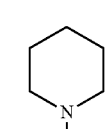 V-86
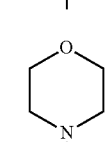 V-87
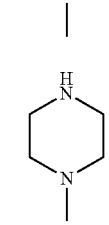 V-88
-continued
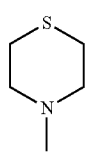 V-89
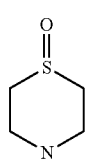 V-90
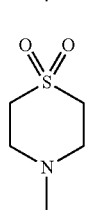 V-91
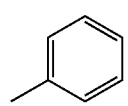 V-92
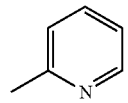 V-93
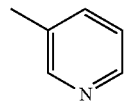 V-94
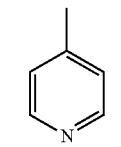 V-95
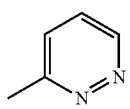 V-96
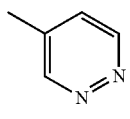 V-97
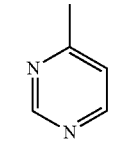 V-98
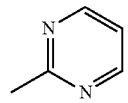 V-99

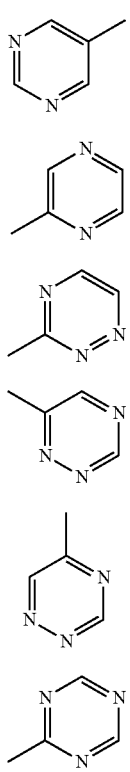

X particularly preferably represents a heteroaromatic 9-membered fused bicyclic ring system from the series Q1, Q2 and Q3, R⁴ particularly preferably represents hydrogen, (C₁-C₄)alkyl, (C₁-C₄)haloalkyl, (C₂-C₄)alkenyl, (C₂-C₄)haloalkenyl, (C₂-C₄)alkynyl, (C₂-C₄)haloalkynyl, (C₁-C₄)alkoxy-(C₁-C₄)alkyl or (C₃-C₆)cycloalkyl, R⁵ particularly preferably represents halogen, (C₁-C₄)alkyl, (C₁-C₄)haloalkyl, (C₂-C₄)alkenyl, (C₂-C₄)haloalkenyl, (C₂-C₄)alkynyl, (C₂-C₄)haloalkynyl, (C₃-C₆)cycloalkyl, (C₁-C₄)haloalkyl-(C₃-C₆)cycloalkyl, cyano-(C₃-C₆)cycloalkyl, halo-(C₃-C₆)cycloalkyl, (C₁-C₄)alkoxy, (C₁-C₄)haloalkoxy, (C₁-C₄)alkoxyimino, (C₁-C₄)haloalkoxyimino, (C₁-C₄)alkylthio, (C₁-C₄)haloalkylthio, (C₁-C₄)alkylsulfinyl, (C₁-C₄)haloalkylsulfinyl, (C₁-C₄)alkylsulfonyl, (C₁-C₄)haloalkylsulfonyl, (C₁-C₄)alkylsulfonyloxy, (C₁-C₄)haloalkylsulfonyloxy, (C₁-C₄)alkylcarbonyl or (C₁-C₄)haloalkylcarbonyl, R⁶ particularly preferably represents hydrogen, cyano, halogen, (C₁-C₄)alkyl, (C₁-C₄)haloalkyl or (C₃-C₆)cycloalkyl, n particularly preferably represents 0, 1 or 2.

In the particularly preferred embodiment, R³ can be optionally mono- or disubstituted, additionally to V, by identical or different substituents selected from cyano, halogen, (C₁-C₄)alkyl, (C₁-C₄)alkoxy or (C₁-C₄)haloalkoxy.

Configuration 4-1

R¹ very particularly preferably represents methyl, ethyl, n-propyl, isopropyl, cyclopropyl, fluoromethyl, difluoromethyl, trifluoromethyl, fluoroethyl, difluoroethyl, trifluoroethyl, tetrafluoroethyl or pentafluoroethyl, R² is very particularly preferably hydrogen, methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R³—V very particularly preferably represents an optionally monosubstituted 5- or 6-membered ring from the series U-1, U-2, U-3, U-4, U-5, U-6, U-7, U-8, U-9, U-10, U-11, U-12, U-13, U-14, U-15, U-24, U-25, U-26, U-27, U-28, U-29, U-30, U-31, U-32, U-33, U-34, U-35, U-41, U-42, U-43, U-44, U-45, U-46, U-47, U-51, U-52, U-53, U-54, U-55, U-56, U-57, U-58, U-61, U-62, U-68, U-69, U-70, U-71, U-72, U-73, U-74, U-75, U-76, U-77, U-78 or U-79, where possible substituents are in each case: cyano, fluorine, chlorine, bromine, methyl, ethyl, n-propyl, isopropyl, n-butyl, isobutyl, tert-butyl, methoxy or trifluoromethoxy, where V very particularly preferably represents a 3- to 6-membered ring, optionally mono- or disubstituted by identical or different substituents from the group consisting of cyano, fluorine, chlorine, bromine, methyl, ethyl, n-propyl, isopropyl, n-butyl, isobutyl, tert-butyl, methoxy and trifluoromethoxy, selected from V-1, V-2, V-3, V-4, V-5, V-6, V-7, V-8, V-9, V-10, V-11, V-12, V-13, V-14, V-15, V-16, V-17, V-18, V-19, V-28, V-29, V-30, V-31, V-32, V-33, V-34, V-35, V-36, V-37, V-38, V-39, V-45, V-46, V-47, V-48, V-49, V-50, V-51, V-58, V-59, V-62, V-63, V-86, V-87, V-88, V-89, V-90, V-91, V-92, V-93, V-94, V-95, V-96, V-97, V-98, V-99, V-100 or V-101, X very particularly preferably represents a heteroaromatic ring system from the series Q2 and Q3, R⁴ very particularly preferably represents methyl, ethyl, n-propyl, isopropyl, n-butyl, isobutyl, tert-butyl, methoxymethyl or methoxyethyl, R⁵ very particularly preferably represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl, R⁶ very particularly preferably represents hydrogen, cyano, methyl, trifluoromethyl, fluorine or chlorine, n very particularly preferably represents 0, 1 or 2.

In the very particularly preferred embodiment, R³ can be optionally monosubstituted, additionally to V, by cyano, fluorine, chlorine, bromine, methyl, ethyl, n-propyl, isopropyl, n-butyl, isobutyl, tert-butyl, methoxy or trifluoromethoxy.

Configuration 5-1

R¹ with emphasis represents ethyl,

R² with emphasis represents methyl,

R³—V with emphasis represents a ring, optionally monosubstituted by bromine, from the series U-1, U-13, U-28, U-42, U-57 and U-70, where V with emphasis represents a ring, optionally monosubstituted by cyano or chlorine, from the series V-1, V-92, V-93 and V-94, X with emphasis represents a heteroaromatic ring system from the series Q2, R⁴ with emphasis represents methyl, R⁵ with emphasis represents trifluoromethyl or pentafluoroethyl, R⁶ with emphasis represents hydrogen, n with emphasis represents 2.

In the emphasized embodiment 5-2, R³ can be optionally monosubstituted, additionally to V, by bromine.

Configuration 5-2
$R^1$ with emphasis represents ethyl,
$R^2$ with emphasis represents methyl,
$R^3$—V with emphasis represents a ring, optionally monosubstituted by cyano or bromine, from the series U-1, U-13, U-28, U-41, U-42, U-57, U-70, U-71 and U-72, where
V with emphasis represents a ring, optionally monosubstituted by cyano, fluorine or chlorine, from the series V-1, V-5, V-87, V-92, V-93 and V-94,
X with emphasis represents a heteroaromatic ring system from the series Q2,
$R^4$ with emphasis is methyl,
$R^5$ with emphasis represents trifluoromethyl or pentafluoroethyl,
$R^6$ with emphasis represents hydrogen,
n with emphasis represents 2.

In the emphasized embodiment 5-2, $R^3$ can be optionally monosubstituted, additionally to V, by cyano or bromine.

The substitution at rings U-1 to U-83 and also V-1 to V-105 can be by substitution of hydrogen at the carbon atom and/or at the nitrogen atom.

In a preferred embodiment, the invention relates to compounds of the formula (I) where X represents

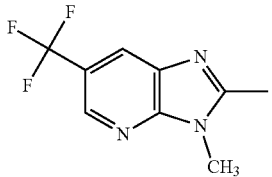

and $R^1$, $R^2$, $R^3$, V and n have the meanings described in configuration (1-1) or configuration (2-1) or configuration (3-1) or configuration (4-1) or configuration (5-1) or configuration (5-2).

In a preferred embodiment, the invention relates to compounds of the formula (I) where X represents

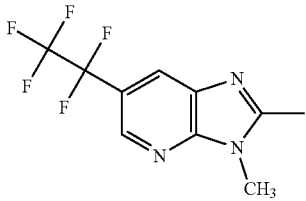 [SMILES: Cc1nc2cc(C(F)(F)C(F)(F)F)cnc2n1C]

and $R^1$, $R^2$, $R^3$, V and n have the meanings described in configuration (1-1) or configuration (2-1) or configuration (3-1) or configuration (4-1) or configuration (5-1) or configuration (5-2).

In a preferred embodiment, the invention relates to compounds of the formula (I) where X represents Q1 and $R^1$, $R^2$, $R^3$, $R^4$, $R^5$, $R^6$, V and n have the meanings given in configuration (2-1) or configuration (3-1) or configuration (4-1) or configuration (5-1) or configuration (5-2).

In a preferred embodiment, the invention relates to compounds of the formula (I) where X represents Q2 and $R^1$, $R^2$, $R^3$, $R^4$, $R^5$, $R^6$, V and n have the meanings given in configuration (2-1) or configuration (3-1) or configuration (4-1) or configuration (5-1) or configuration (5-2).

In a preferred embodiment, the invention relates to compounds of the formula (I) where X represents Q3 and $R^1$, $R^2$, $R^3$, $R^5$, $R^6$, V and n have the meanings given in configuration (2-1) or configuration (3-1) or configuration (4-1) or configuration (5-1) or configuration (5-2).

In a preferred embodiment, the invention relates to compounds of the formula (I) where X represents Q4 and $R^1$, $R^2$, $R^3$, $R^5$, $R^6$, V and n have the meanings given in configuration (2-1) or configuration (3-1) or configuration (4-1) or configuration (5-1) or configuration (5-2).

In a preferred embodiment, the invention relates to compounds of the formula (I) where X represents Q5 and $R^1$, $R^2$, $R^3$, $R^5$, $R^6$, V and n have the meanings given in configuration (2-1) or configuration (3-1) or configuration (4-1) or configuration (5-1) or configuration (5-2).

In a preferred embodiment, the invention relates to compounds of the formula (I) where X represents Q6 and $R^1$, $R^2$, $R^3$, $R^5$, $R^6$, V and n have the meanings given in configuration (2-1) or configuration (3-1) or configuration (4-1) or configuration (5-1) or configuration (5-2).

In the general or preferred definitions, unless stated otherwise, halogen is selected from the group consisting of fluorine, chlorine, bromine and iodine, preferably in turn from the group consisting of fluorine, chlorine and bromine.

Aryl (including as part of a larger unit, for example arylalkyl), unless defined differently elsewhere, is selected from the series phenyl, naphthyl, anthryl, phenanthrenyl, and is preferably in turn phenyl.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Particular preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. In this case, halogen represents fluorine, chlorine, bromine or iodine, in particular fluorine, chlorine or bromine.

Unless stated otherwise, optionally substituted radicals may be mono- or polysubstituted, where the substituents in the case of poly substitutions may be the same or different.

The radical definitions or illustrations given in general terms or listed within ranges of preference apply correspondingly to end products and to starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Emphasis according to the invention is given to using compounds of the formula (I) which contain a combination of the meanings listed above as being emphasized.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

The compounds of the formula (I) according to the invention can be obtained by the processes shown in the following schemes:

Process A

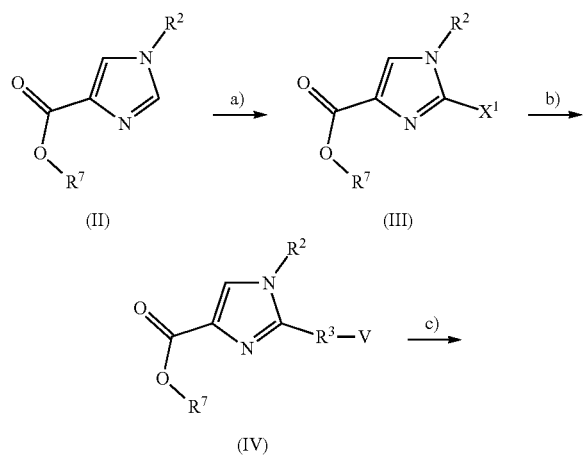

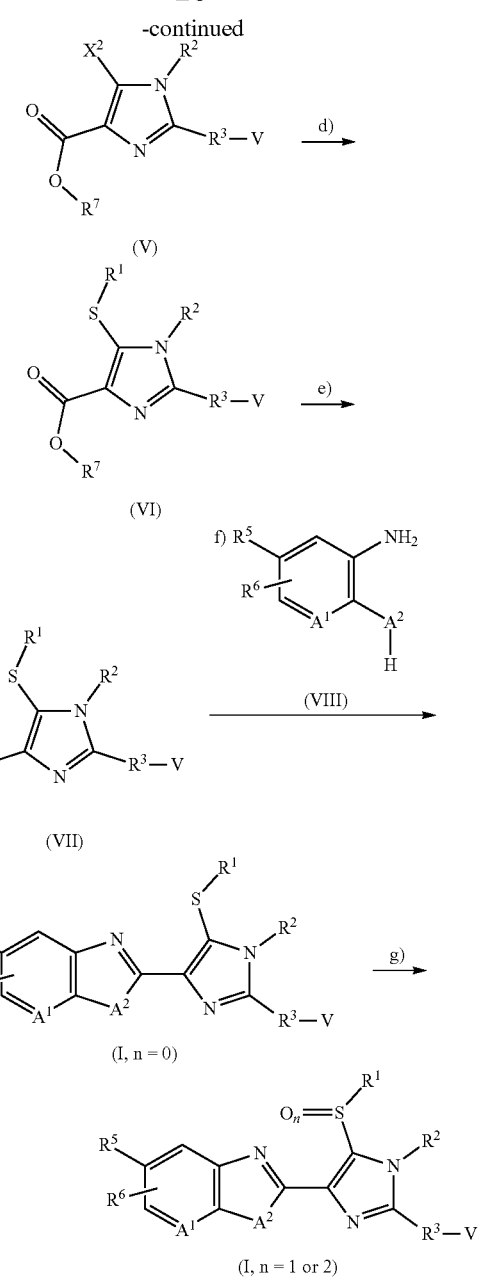

The radicals $R^1$, $R^2$, $R^3$, $R^5$, $R^6$ and V have the meanings described above. $A^1$ represents N or CH and $A^2$ represents —N—$R^4$, O or S, where $R^4$ has the meaning described above. $X^1$ and $X^2$ represent halogen. $R^7$ represents $(C_1$-$C_4)$-alkyl.

Step a)

Compounds of the formula (III) may be prepared from imidazole derivatives of the formula (II), for example by reaction with a halogenating reagent such as N-bromosuccinimide (NBS) in a solvent such as for example tetrahydrofuran or by reaction of compounds of the formula (II) with NBS in combination with azobis(isobutyronitrile) (AIBN) in tetrachloromethane or chloroform, for example analogously to the processes described in WO 2013/149997, WO 2014/115077 or WO 2011/123609.

Imidazole derivatives of the formula (II) are either commercially available or can be prepared by known methods, for example analogously to the processes described in WO 2014/191894, US 2003/229079 or WO 2013/156608.

Step b)

Compounds of the formula (III), in which $X^1$ is preferably halogen from the series chlorine or bromine, may be converted to compounds of the formula (IV), for example by transition metal-mediated cross-couplings [cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004] or by nucleophilic aromatic substitution (cf. the processes described in *Bioorganic and Medicinal Chemistry Letters* 2007, 17, 5825-5830 or U.S. Pat. No. 4,125,726).

For example, compounds of the formula (III), in which $X^1$ is preferably chlorine or bromine, may be reacted with suitable boronic acids $[V—R^3—B(OH)_2]$ or boronic esters according to known methods (cf. WO 2012/143599, US 2014/094474, US 2014/243316, US 2015/284358 or *Journal of Organic Chemistry* 2004, 69, 8829-8835) in the presence of suitable catalysts from the series of transition metal salts to give compounds of the formula (IV). Examples of preferred coupling catalysts include palladium catalysts such as [1,1'-bis(diphenylphosphino)ferrocene]dichloropalladium(II), bis(triphenylphosphine)palladium(II) dichloride or tetrakis(triphenylphosphine)palladium. Suitable basic reaction auxiliaries used to conduct the processes are preferably carbonates of sodium, potassium or caesium. Some of the required boronic acid derivatives $[V—R^3—B(OH)_2]$ or boronic ester derivatives are known and/or commercially available, or they can be prepared by generally known methods (cf. Boronic Acids (eds.: D. G. Hall), 2nd ed., Wiley-VCH, Weinheim, 2011). In this case, the reaction is preferably conducted in a mixture of water and an organic solvent selected from customary solvents that are inert under the prevailing reaction conditions. Ethers such as tetrahydrofuran, dioxane or 1,2-dimethoxyethane are frequently used.

Alternatively, it is possible to use stannane derivatives $[V—R^3—Sn(n-Bu)_3]$ as coupling partners (cf. US 2013/281433, WO 2004/099177 or WO 2016/071214). Some of the required stannane derivatives $[V—R^3—Sn(n-Bu)_3]$ are known and/or commercially available, or they can be prepared by generally known methods (cf. WO 2016/071214 or WO 2007/148093).

Coupling of the halogenated imidazole derivatives of the formula (III) with NH-containing heteroaromatics such as imidazoles or pyrazoles, optionally substituted as described above, to give compounds of the formula (IV) can be conducted by reaction under basic conditions (e.g. with sodium hydride in dimethylformamide, cf., for example WO 2005/058898). Alternatively, the reaction can be carried out under an inert gas atmosphere by catalysis with copper(I) salts, copper(I) iodide for example, in the presence of a suitable ligand, e.g. trans-N,N'-dimethylcyclohexane-1,2-diamine or R-(+)-proline, and a suitable base, e.g. potassium carbonate or potassium phosphate, in a suitable solvent such as 1,4-dioxane or toluene (cf., for example WO 2016/109559).

Step c)

Imidazole derivatives of the formula (V), in which $X^2$ is preferably halogen from the series of bromine or iodine, may be prepared using standard methods from compounds of the formula (IV) by reaction with, for example, bromine or N-bromosuccinimide (NBS), (cf. WO 2009/115572 or WO 2010/091411) or N-iodosuccinimide (NIS), optionally in the presence of acetic acid or trifluoroacetic acid (cf. WO 2008/063287, WO 2007/087548 or WO 2009/152025).

Step d)

Compounds of the formula (V), in which $X^2$ is preferably halogen from the series of bromine or iodine, may be converted to compounds of the formula (VI), for example by reaction under basic conditions with mercaptan derivatives $(R^1—SH)$ and copper(I) salts (cf. EP257918 or WO 2009/152025) or by nucleophilic aromatic substitution (cf. *Australian Journal of Chemistry* 1987, 40, 1415-1425).

Alternatively, the reaction of compounds of the formula (V), in which $X^2$ is preferably halogen from the series of bromine or iodine, with mercaptan derivatives $(R^1—SH)$ can be carried out in the presence of palladium catalysts such as tris(dibenzylideneacetone)dipalladium $[Pd_2(dba)_3]$. In this case, frequently used are amine bases such as triethylamine or N,N-diisopropylethylamine (DIPEA) and also phosphine ligands such as Xantphos (cf. WO 2013/025958, WO 2013/066869, US 2009/027039, WO 2011/058149, WO 2011/143466 or *Bioorganic and Medicinal Chemistry Letters* 2016, 26, 2984-2987). In this case, the reaction is preferably conducted in a solvent selected from customary solvents that are inert under the prevailing reaction conditions. Preference is given to ethers, for example dioxane or 1,2-dimethoxy ethane.

Mercaptan derivatives, for example methyl mercaptan, ethyl mercaptan or isopropyl mercaptan, are either commercially available or can be prepared by known methods, for example analogously to the processes described in US 2006/025633, US 2006/111591, U.S. Pat. No. 2,820,062, Chemical Communications 2000, 13, 1163-1164 or *Journal of the American Chemical Society* 1922, 44, 1323-1333.

Step e)

Esters of the formula (VI) can be converted to carboxylic acids of the formula (VII) using standard methods (cf., for example, WO 2014/191894, US 2006/194779, WO 2014/086663 or European *Journal of Organic Chemistry* 2009, 213-222), for example with an alkali metal hydroxide as base, such as sodium hydroxide or lithium hydroxide, in an alcohol as solvent, for example methanol or ethanol.

Step 1)

Compounds of the formula (I, n=0) can be prepared from compounds of the formulae (VII) with compounds of the formula (VIII) in the presence of a condensing agent.

Compounds of the formula (VIII) are either commercially available or can be prepared by known methods, for example analogously to the methods described in WO 2010/125985, WO 2012/074135, WO 2012/086848, WO 2013/018928, WO 2015/000715, WO 2015/121136, WO 2016/039441, WO 2016/059145, WO 2016/071214, WO 2016/169882, WO 2016/169886 or WO 2016/124557.

The conversion to compounds of the formula (I, n=0) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

The reaction can be conducted in the presence of a suitable catalyst, for example 1-hydroxybenzotriazole.

The reaction can be carried out in the presence of an acid or a base.

Examples of an acid which can be used in the reaction described are sulfonic acids such as methanesulfonic acid or para-toluenesulfonic acid; carboxylic acids such as acetic acid, or polyphosphoric acids.

Examples of suitable bases are nitrogenous heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

Step g)

The compounds of the formula (I, n=1 or 2) can be prepared by oxidation of compounds of the formula (I, n=0), for example analogously to the processes described in WO 2016/169882 or WO 2016/124557. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing compositions are hydrogen peroxide and meta-chloroperbenzoic acid.

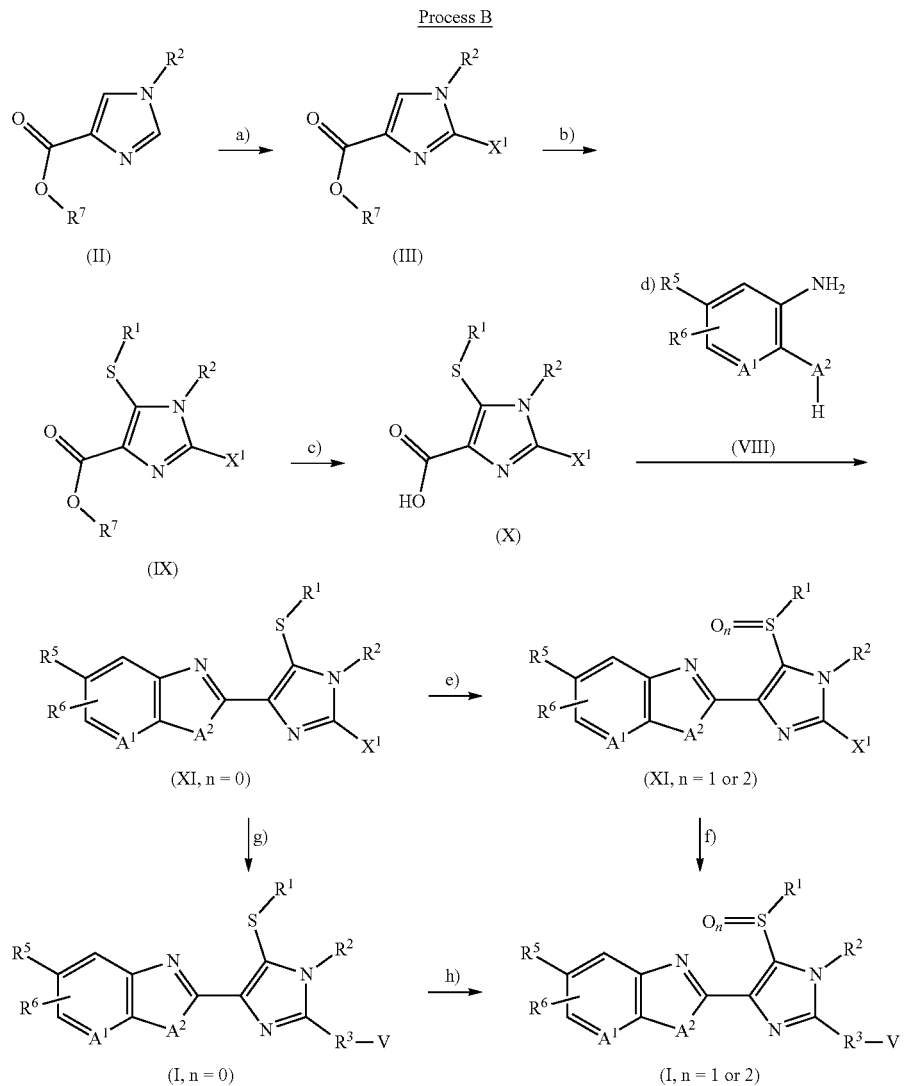

The radicals $R^1$, $R^2$, $R^3$, $R^5$, $R^6$ and V have the meanings described above. $A^1$ represents N or CH and $A^2$ represents —N—$R^4$, O or S, where $R^4$ has the meaning described above. $X^1$ represents halogen. $R^7$ represents $(C_1-C_4)$-alkyl.

Step a)

Compounds of the formula (III) may be prepared from imidazole derivatives of the formula (II), for example by reaction with a halogenating reagent such as N-bromosuccinimide (NBS) in a solvent such as for example tetrahydrofuran or by reaction of compounds of the formula (II) with NBS in combination with azobis(isobutyronitrile) (AIBN) in carbon tetrachloride or chloroform, for example analogously to the processes described in WO 2013/149997, WO 2014/115077 or WO 2011/123609.

Imidazole derivatives of the formula (II) are either commercially available or can be prepared by known methods, for example analogously to the processes described in WO 2014/191894, US 2003/229079 or WO 2013/156608.

Step b)

Imidazole derivatives of the formula (IX) may be prepared using standard methods from compounds of the formula (III) by reaction with a disulfide ($R^1$—S—S—$R^1$) and, for example, a strong base, preferably lithium diisopropylamide (LDA) in tetrahydrofuran (cf. *Bioorganic and Medicinal Chemistry Letters* 2010, 20, 1084-1089) or, for example, hydrogen peroxide and iodine in ethanol (cf. Synthesis 2015, 47, 659-671).

Step c)

The conversion of compounds of the formula (IX) into compounds of the formula (X) is carried out analogously to process A, step e).

Step d)

The reaction of compounds of the formula (X) with compounds of the formula (VIII) to give compounds of the formula (XI, n=0) is carried out analogously to process A, step f).

Step e, h)

The conversion of compounds of the formula (XI, n=0) into compounds of the formula (XI, n=1 or 2) and also the conversion of compounds of the formula (I, n=0) into compounds of the formula (I, n=1 or 2) are carried out analogously to process A, step g).

Step f, g)

The conversion of compounds of the formula (XI, n=0) into compounds of the formula (I, n=0) and also the conversion of compounds of the formula (XI, n=1 or 2) into compounds of the formula (I, n=1 or 2) are carried out analogously to process A, step b).

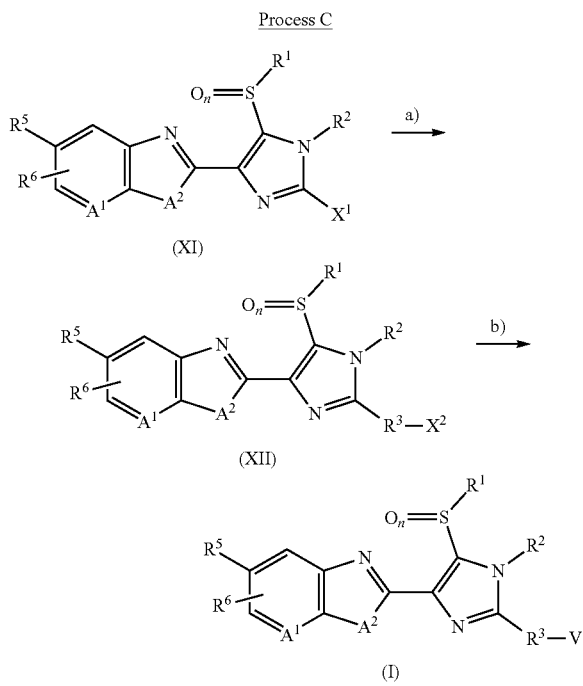

The radicals $R^1$, $R^2$, $R^3$, $R^5$, $R^6$ and V have the meanings described above. $A^1$ represents N or CH and $A^2$ represents —N—$R^4$, O or S, where $R^4$ has the meaning described above. $X^1$ and $X^2$ represent halogen. n represents 0, 1 or 2.

Step a)

The preparation of compounds of the formula (XII) in which $R^3$—$X^2$ represents a ring attached to the remainder of the molecule via nitrogen can take place for example from compounds of the formula (XI) for which $X^1$ is preferably halogen from the series chlorine or bromine, by methods known in the literature (see, for example, *Journal of Organic Chemistry* 2010, 69, 5578-5587), e.g. in the presence of copper(I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons. Preference is given to using toluene. Furthermore, the coupling can take place from compounds of the formula (XI), for which $X^1$ preferably represents halogen from the series fluorine, chlorine or bromine, without metal catalysis in the presence of a suitable base such as, for example, potassium carbonate or caesium carbonate in a suitable solvent or diluent. Useful solvents or diluents include all inert organic solvents, for example aliphatic or aromatic hydrocarbons. Preference is given here to using acetonitrile or dimethylformamide.

The required compounds of the formula H—$R^3$—$X^2$ are either commercially available or can be prepared by known methods.

Compounds of the formula (XII) for which $R^3$—$X^2$ represents a ring attached to the remainder of the molecule via carbon can be prepared for example from compounds of the formula (XI), for which $X^1$ preferably represents halogen from the series chlorine or bromine, by generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004).

For example, compounds of the formula (XI) in which $X^1$ preferably represents chlorine or bromine can be reacted with suitable arylboronic acids or esters thereof by known methods (cf. WO 2010071819) in the presence of suitable catalysts from the series of the transition metal salts to give compounds of the formula (XII). Examples of preferred coupling catalysts include palladium catalysts such as [1,1'-bis(diphenylphosphino)ferrocene]dichloropalladium(II) or tetrakis(triphenylphosphine)palladium. Suitable basic reaction auxiliaries used to conduct the processes are preferably carbonates of sodium or potassium.

Some of the (hetero)arylboronic acids or (hetero)arylboronic esters required are known and/or commercially available, or they can be prepared by generally known methods (cf. Boronic Acids (eds.: D. G. Hall), 2nd ed., Wiley-VCH, Weinheim, 2011).

Step b)

The preparation of compounds of the formula (I) in which $R^3$—V represents a bicyclic radical attached to the remainder of the molecule via nitrogen can take place for example from compounds of the formula (XII) for which $X^2$ is preferably halogen from the series chlorine or bromine, by methods known in the literature (see, for example, *Journal of Organic Chemistry* 2010, 69, 5578-5587), e.g. in the presence of copper(I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons. Preference is given to using toluene. Furthermore, the coupling can take place from compounds of the formula (XII), for which $X^2$ preferably represents halogen from the series fluorine, chlorine or bromine, without metal catalysis in the presence of a suitable base such as, for example, potassium carbonate or caesium carbonate in a suitable solvent or diluent. Useful solvents or diluents include all inert organic solvents, for example aliphatic or aromatic hydrocarbons. Preference is given here to using acetonitrile or dimethylformamide.

The required compounds of the formula H-V are either commercially available or can be prepared by known methods.

Compounds of the formula (I) for which $R^3$—V represents a bi-cycle attached to the remainder of the molecule via carbon can be prepared for example from compounds of the formula (XII), for which $X^2$ preferably represents halogen from the series chlorine or bromine, by generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004).

For example, compounds of the formula (XII) in which $X^2$ preferably represents chlorine or bromine can be reacted with suitable arylboronic acids or esters thereof by known methods (cf. WO 2010/071819) in the presence of suitable catalysts from the series of the transition metal salts to give compounds of the formula (I). Examples of preferred coupling catalysts include palladium catalysts such as [1,1'-bis(diphenylphosphino)ferrocene]dichloropalladium(II) or tetrakis(triphenylphosphine)palladium.

Suitable basic reaction auxiliaries used to conduct the processes are preferably carbonates of sodium or potassium.

Some of the (hetero)arylboronic acids or (hetero)arylboronic esters required are known and/or commercially available, or they can be prepared by generally known methods (cf. Boronic Acids (eds.: D. G. Hall), 2nd ed., Wiley-VCH, Weinheim, 2011).

The radicals $R^1$, $R^2$, $R^3$, $R^5$, $R^6$ and V have the meanings described above. A' represents N or CH and $A^2$ represents —N—$R^4$, O or S, where $R^4$ has the meaning described above. $X^1$ represents halogen. n represents 0, 1 or 2.

Step a)

Compounds of the formula (XI) are converted to compounds of the formula (XIII) analogously to process A, step b).

Step b)

Compounds of the formula (I) can be prepared from vinyl derivatives of the formula (XIII), for example by reaction with a halogenating reagent such as N-chlorosuccinimide (NCS) in a solvent such as trichloromethane, for example analogously to the processes described in WO 2009/067613 or Bulletin Chemical Society Japan 1984, 57, 2184-2187.

Aldoximes of the formula (XIV) are either commercially available or can be prepared by known methods, for example analogously to the processes described in US 2007/037816.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticides" in each case also always encompasses the term "crop protection agents".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are conducted on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

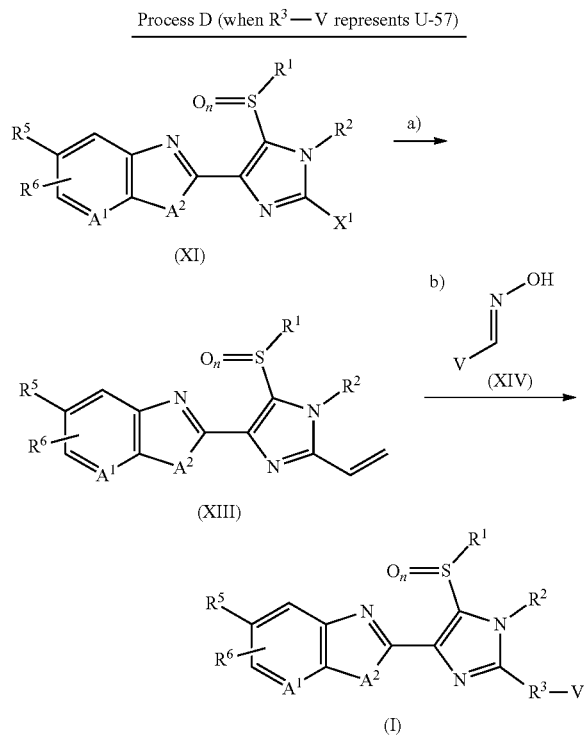

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus, Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conorus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloborus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasiorma serricorne, Latheticus oryzae, Lathridius* spp., *Lema* spp., *Leptinotarsa decemlineata, Leucoptera* spp., e.g. *Leucoptera coffeella, Limonius ectypus, Lissorhoptrus oryzophilus, Listronotus* (=*Hyperodes*) spp., *Lixus* spp., *Luperodes* spp., *Luperomorpha xanthora, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Spheno-*

*phorus* spp., *Stegobium paniceum*, *Sternechus* spp., e.g. *Sternechus paludatus*, *Symphyletes* spp., *Tanymecus* spp., e.g. *Tanymecus dilaticollis*, *Tanymecus indicus*, *Tanymecus palliatus*, *Tenebrio molitor*, *Tenebrioides mauretanicus*, *Tribolium* spp., e.g. *Tribolium audax*, *Tribolium castaneum*, *Tribolium confusum*, *Trogorma* spp., *Tychius* spp., *Xylotrechus* spp., *Zabrus* spp., e.g. *Zabrus tenebrioides;* from the order of the Dermaptera, for example *Anisolabis maritime*, *Forficula auricularia*, *Labidura riparia;* from the order of the Diptera, for example *Aedes* spp., e.g. *Aedes aegypti*, *Aedes albopictus*, *Aedes sticticus*, *Aedes vexans*, *Agromyza* spp., e.g. *Agromyza frontella*, *Agromyza parvicornis*, *Anastrepha* spp., *Anopheles* spp., e.g. *Anopheles quadrimaculatus*, *Anopheles gambiae*, *Asphondylia* spp., *Bactrocera* spp., e.g. *Bactrocera cucurbitae*, *Bactrocera dorsalis*, *Bactrocera oleae*, *Bibio hortulanus*, *Calliphora erythrocephala*, *Calliphora vicina*, *Ceratitis capitata*, *Chironomus* spp., *Chrysomya* spp., *Chrysops* spp., *Chrysozona pluvialis*, *Cochliomya* spp., *Contarinia* spp., e.g. *Contarinia johnsoni*, *Contarinia nasturtii*, *Contarinia pyrivora*, *Contarinia schulzi*, *Contarinia sorghicola*, *Contarinia tritici*, *Cordylobia anthropophaga*, *Cricotopus sylvestris*, *Culex* spp., e.g. *Culex pipiens*, *Culex quinquefasciatus*, *Culicoides* spp., *Culiseta* spp., *Cuterebra* spp., *Dacus oleae*, *Dasineura* spp., e.g. *Dasineura brassicae*, *Delia* spp., e.g. *Delia antiqua*, *Delia coarctata*, *Delia florilega*, *Delia platura*, *Delia radicum*, *Dermatobia hominis*, *Drosophila* spp., e.g. *Drosphila melanogaster*, *Drosophila suzukii*, *Echinocnemus* spp., *Euleia heraclei*, *Fannia* spp., *Gasterophilus* spp., *Glossina* spp., *Haematopota* spp., *Hydrellia* spp., *Hydrellia griseola*, *Hylemya* spp., *Hippobosca* spp., *Hyporma* spp., *Liriomyza* spp., e.g. *Liriomyza brassicae*, *Liriomyza huidobrensis*, *Liriomyza sativae*, *Lucilia* spp., e.g. *Lucilia cuprina*, *Lutzomyia* spp., *Mansonia* spp., *Musca* spp., e.g. *Musca domestica*, *Musca domestica vicina*, *Oestrus* spp., *Oscinella frit*, *Paratanytarsus* spp., *Paralauterborniella subcincta*, *Pegomya* or *Pegomyia* spp., e.g. *Pegomya betae*, *Pegomya hyoscyami*, *Pegomya rubivora*, *Phlebotomus* spp., *Phorbia* spp., *Phormia* spp., *Piophila casei*, *Platyparea poeciloptera*, *Prodiplosis* spp., *Psila rosae*, *Rhagoletis* spp., e.g. *Rhagoletis cingulata*, *Rhagoletis completa*, *Rhagoletis fausta*, *Rhagoletis indifferens*, *Rhagoletis mendax*, *Rhagoletis pomonella*, *Sarcophaga* spp., *Simulium* spp., e.g. *Simulium meridionale*, *Stomoxys* spp., *Tabanus* spp., *Tetanops* spp., *Tipula* spp., e.g. *Tipula paludosa*, *Tipula simplex*, *Toxotrypana curvicauda;* from the order of the Hemiptera, for example *Acizzia acaciaebaileyanae*, *Acizzia dodonaeae*, *Acizzia uncatoides*, *Acrida turrita*, *Acyrthosipon* spp., e.g. *Acyrthosiphon pisum*, *Acrogonia* spp., *Aeneolamia* spp., *Agonoscena* spp., *Aleurocanthus* spp., *Aleyrodes proletella*, *Aleurolobus barodensis*, *Aleurothrixus floccosus*, *Allocaridara malayensis*, *Amrasca* spp., e.g. *Amrasca bigutulla*, *Amrasca devastans*, *Anuraphis cardui*, *Aonidiella* spp., e.g. *Aonidiella aurantii*, *Aonidiella citrina*, *Aonidiella inornata*, *Aphanostigma piri*, *Aphis* spp., e.g. *Aphis citricola*, *Aphis craccivora*, *Aphis fabae*, *Aphis forbesi*, *Aphis glycines*, *Aphis gossypii*, *Aphis hederae*, *Aphis illinoisensis*, *Aphis middletoni*, *Aphis nasturtii*, *Aphis nerii*, *Aphis pomi*, *Aphis spiraecola*, *Aphis viburniphila*, *Arboridia apicalis*, *Arytainilla* spp., *Aspidiella* spp., *Aspidiotus* spp., e.g. *Aspidiotus nerii*, *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., e.g. *Cacopsylla pyricola*, *Calligypona marginata*, *Capulinia* spp., *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus aonidum*, *Chrysomphalus ficus*, *Cicadulina mbila*, *Coccomytilus halli*, *Coccus* spp., e.g. *Coccus hesperidum*, *Coccus longulus*, *Coccus pseudomagnoliarum*, *Coccus viridis*, *Cryptomyzus ribis*, *Cryptoneossa* spp., *Ctenarytaina* spp., *Dalbulus* spp., *Dialeurodes chittendeni*, *Dialeurodes citri*, *Diaphorina citri*, *Diaspis* spp., *Diuraphis* spp., *Doralis* spp., *Drosicha* spp., *Dysaphis* spp., e.g. *Dysaphis apiifolia*, *Dysaphis plantaginea*, *Dysaphis tulipae*, *Dysmicoccus* spp., *Empoasca* spp., e.g. *Empoasca abrupta*, *Empoasca fabae*, *Empoasca maligna*, *Empoasca solana*, *Empoasca stevensi*, *Eriosoma* spp., e.g. *Eriosoma americanum*, *Eriosoma lanigerum*, *Eriosoma pyricola*, *Erythroneura* spp., *Eucalyptolyma* spp., *Euphyllura* spp., *Euscelis bilobatus*, *Ferrisia* spp., *Fiorinia* spp., *Furcaspis oceanica*, *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., e.g. *Icerya purchasi*, *Idiocerus* spp., *Idioscopus* spp., *Laodelphax striatellus*, *Lecanium* spp., e.g. *Lecanium corni* (=*Parthenolecanium corni*), *Lepidosaphes* spp., e.g. *Lepidosaphes ulmi*, *Lipaphis erysimi*, *Lopholeucaspis japonica*, *Lycorma delicatula*, *Macrosiphum* spp., e.g. *Macrosiphum euphorbiae*, *Macrosiphum lilii*, *Macrosiphum rosae*, *Macrosteles facifrons*, *Mahanarva* spp., *Melanaphis sacchari*, *Metcalfiella* spp., *Metcalfa pruinosa*, *Metopolophium dirhodum*, *Monellia costalis*, *Monelliopsis pecanis*, *Myzus* spp., e.g. *Myzus ascalonicus*, *Myzus cerasi*, *Myzus ligustri*, *Myzus ornatus*, *Myzus persicae*, *Myzus nicotianae*, *Nasonovia ribisnigri*, *Neomaskellia* spp., *Nephotettix* spp., e.g. *Nephotettix cincticeps*, *Nephotettix nigropictus*, *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., e.g. *Paratrioza cockerelli*, *Parlatoria* spp., *Pemphigus* spp., e.g. *Pemphigus bursarius*, *Pemphigus populivenae*, *Peregrinus maidis*, *Perkinsiella* spp., *Phenacoccus* spp., e.g. *Phenacoccus madeirensis*, *Phloeomyzus passerinii*, *Phorodon humuli*, *Phylloxera* spp., e.g. *Phylloxera devastatrix*, *Phylloxera notabilis*, *Pinnaspis aspidistrae*, *Planococcus* spp., e.g. *Planococcus citri*, *Prosopidopsylla flava*, *Protopulvinaria pyriformis*, *Pseudaulacaspis pentagona*, *Pseudococcus* spp., e.g. *Pseudococcus calceolariae*, *Pseudococcus comstocki*, *Pseudococcus longispinus*, *Pseudococcus maritimus*, *Pseudococcus viburni*, *Psyllopsis* spp., *Psylla* spp., e.g. *Psylla buxi*, *Psylla mali*, *Psylla pyri*, *Pteromalus* spp., *Pulvinaria* spp., *Pyrilla* spp., *Quadraspidiotus* spp., e.g. *Quadraspidiotus juglansregiae*, *Quadraspidiotus ostreaeformis*, *Quadraspidiotus perniciosus*, *Quesada gigas*, *Rastrococcus* spp., *Rhopalosiphum* spp., e.g. *Rhopalosiphum maidis*, *Rhopalosiphum oxyacanthae*, *Rhopalosiphum padi*, *Rhopalosiphum rufiabdominale*, *Saissetia* spp., e.g. *Saissetia coffeae*, *Saissetia miranda*, *Saissetia neglecta*, *Saissetia oleae*, *Scaphoideus titanus*, *Schizaphis graminum*, *Selenaspidus articulatus*, *Sipha flava*, *Sitobion avenae*, *Sogata* spp., *Sogatella furcifera*,

*Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., e.g. *Toxoptera aurantii*, *Toxoptera citricidus*, *Trialeurodes vaporariorum*, *Trioza* spp., e.g. *Trioza diospyri*, *Typhlocyba* spp., *Unaspis* spp., *Viteus vitifolii*, *Zygina* spp.;

from the suborder of the Heteroptera, for example *Aelia* spp., *Anasa tristis*, *Antestiopsis* spp., *Boisea* spp., *Blissus* spp., *Calocoris* spp., *Campylomma livida*, *Caverius* spp., *Cimex* spp., e.g. *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., e.g. *Euschistus heros*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygocoris* spp., e.g. *Lygocoris pabulinus*, *Lygus* spp., e.g. *Lygus elisus*, *Lygus hesperus*, *Lygus lineolaris*, *Macropes excavatus*, *Megacopta cribraria*, *Miridae*, *Monalonion atratum*, *Nezara* spp., e.g. *Nezara viridula*, *Nysius* spp., *Oebalus* spp., *Pentomidae*, *Piesma quadrata*, *Piezodorus* spp., e.g. *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example *Acromyrmex* spp., *Athalia* spp., e.g. *Athalia rosae*, *Atta* spp., *Camponotus* spp., *Dolichovespula* spp., *Diprion* spp., e.g. *Diprion similis*, *Hoplocampa* spp., e.g. *Hoplocampa cookei*, *Hoplocampa testudinea*, *Lasius* spp., *Linepithema* (*Iridiomyrmex*) *humile*, *Monomorium pharaonis*, *Paratrechina* spp., *Paravespula* spp., *Plagiolepis* spp., *Sirex* spp., e.g. *Sirex noctilio*, *Solenopsis invicta*, *Tapinoma* spp., *Technomyrmex albipes*, *Urocerus* spp., *Vespa* spp., e.g. *Vespa crabro*, *Wasmannia auropunctata*, *Xeris* spp.;

from the order of the Isopoda, for example *Armadillidium vulgare*, *Oniscus asellus*, *Porcellio scaber*;

from the order of the Isoptera, for example *Coptotermes* spp., e.g. *Coptotermes formosanus*, *Cornitermes cumulans*, *Cryptotermes* spp., *Incisitermes* spp., *Kalotermes* spp., *Microtermes obesi*, *Nasutitermis* spp., *Odontotermes* spp., *Porotermes* spp., *Reticulitermes* spp., e.g. *Reticulitermes flavipes*, *Reticulitermes hesperus*;

from the order of the Lepidoptera, for example *Achroia grisella*, *Acronicta major*, *Adoxophyes* spp., e.g. *Adoxophyes orana*, *Aedia leucomelas*, *Agrotis* spp., e.g. *Agrotis segetum*, *Agrotis ipsilon*, *Alabama* spp., e.g. *Alabama argillacea*, *Amyelois transitella*, *Anarsia* spp., *Anticarsia* spp., e.g. *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., e.g. *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., e.g. *Cydia nigricana*, *Cydia pomonella*, *Dalaca noctuides*, *Diaphania* spp., *Diparopsis* spp., *Diatraea saccharalis*, *Dioryctria* spp., e.g. *Dioryctria zimmermani*, *Earias* spp., *Ecdytolopha aurantium*, *Elasmopalpus lignosellus*, *Eldana saccharina*, *Ephestia* spp., e.g. *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., e.g. *Euproctis chrysorrhoea*, *Euxoa* spp., *Feltia* spp., *Galleria mellonella*, *Gracillaria* spp., *Grapholitha* spp., e.g. *Grapholita molesta*, *Grapholita prunivora*, *Hedylepta* spp., *Helicoverpa* spp., e.g. *Helicoverpa armigera*, *Helicoverpa zea*, *Heliothis* spp., e.g. *Heliothis virescens*, *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., e.g. *Leucoptera coffeella*, *Lithocolletis* spp., e.g. *Lithocolletis blancardella*, *Lithophane antennata*, *Lobesia* spp., e.g. *Lobesia botrana*, *Loxagrotis albicosta*, *Lymantria* spp., e.g. *Lymantria dispar*, *Lyonetia* spp., e.g. *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., e.g. *Ostrinia nubilalis*, *Panolis flammea*, *Parnara* spp., *Pectinophora* spp., e.g. *Pectinophora gossypiella*, *Perileucoptera* spp., *Phthorimaea* spp., e.g. *Phthorimaea operculella*, *Phyllocnistis citrella*, *Phyllonorycter* spp., e.g. *Phyllonorycter blancardella*, *Phyllonorycter crataegella*, *Pieris* spp., e.g. *Pieris rapae*, *Platynota stultana*, *Plodia interpunctella*, *Plusia* spp., *Plutella xylostella* (=*Plutella maculipennis*), *Podesia* spp., e.g. *Podesia syringae*, *Prays* spp., *Prodenia* spp., *Protoparce* spp., *Pseudaletia* spp., e.g. *Pseudaletia unipuncta*, *Pseudoplusia includens*, *Pyrausta nubilalis*, *Rachiplusia nu*, *Schoenobius* spp., e.g. *Schoenobius bipunctifer*, *Scirpophaga* spp., e.g. *Scirpophaga innotata*, *Scotia segetum*, *Sesamia* spp., e.g. *Sesamia inferens*, *Sparganothis* spp., *Spodoptera* spp., e.g. *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., e.g. *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., e.g. *Gryllotalpa gryllotalpa*, *Hieroglyphus* spp., *Locusta* spp., e.g. *Locusta migratoria*, *Melanoplus* spp., e.g. *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., e.g. *Ctenocephalides canis*, *Ctenocephalides felis*, *Pulex irritans*, *Tunga penetrans*, *Xenopsylla cheopis*;

from the order of the Thysanoptera, for example *Anaphothrips obscurus*, *Baliothrips biformis*, *Chaetanaphothrips leeuweni*, *Drepanothrips reuteri*, *Enneothrips*

*flavens, Frankliniella* spp., e.g. *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., e.g. *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, e.g. from the class of the Bivalvia, e.g. *Dreissena* spp.;

and from the class of the Gastropoda, for example *Anion* spp., e.g. *Anion ater rufus, Biomphalaria* spp., *Bulinus* spp., *Deroceras* spp., e.g. *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., e.g. *Aglenchus agricola, Anguina* spp., e.g. *Anguina tritici, Aphelenchoides* spp., e.g. *Aphelenchoides arachidis, Aphelenchoides fragariae, Belonolaimus* spp., e.g. *Belonolaimus gracilis, Belonolaimus longicaudatus, Belonolaimus nortoni, Bursaphelenchus* spp., e.g. *Bursaphelenchus cocophilus, Bursaphelenchus eremus, Bursaphelenchus xylophilus, Cacopaurus* spp., e.g. *Cacopaurus pestis, Criconemella* spp., e.g. *Criconemella curvata, Criconemella onoensis, Criconemella ornata, Criconemella rusium, Criconemella xenoplax* (=*Mesocriconema xenoplax*), *Criconemoides* spp., e.g. *Criconemoides ferniae, Criconemoides onoense, Criconemoides ornatum, Ditylenchus* spp., e.g. *Ditylenchus dipsaci, Dolichodorus* spp., *Globora* spp., e.g. *Globora pallida, Globora rostochiensis, Helicotylenchus* spp., e.g. *Helicotylenchus dihystera, Hemicriconemoides* spp., *Hemicycliophora* spp., *Heterora* spp., e.g. *Heterora avenae, Heterora glycines, Heterora schachtii, Hirschmaniella* spp., *Hoplolaimus* spp., *Longidorus* spp., e.g. *Longidorus africanus, Meloidogyne* spp., e.g. *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., e.g. *Paratrichodorus minor, Paratylenchus* spp., *Pratylenchus* spp., e.g. *Pratylenchus penetrans, Pseudohalenchus* spp., *Psilenchus* spp., *Punctora* spp., *Quinisulcius* spp., *Radopholus* spp., e.g. *Radopholus citrophilus, Radopholus similis, Rotylenchulus* spp., *Rotylenchus* spp., *Scutellonema* spp., *Subanguina* spp., *Trichodorus* spp., e.g. *Trichodorus obtusus, Trichodorus primitivus, Tylenchorhynchus* spp., e.g. *Tylenchorhynchus annulatus, Tylenchulus* spp., e.g. *Tylenchulus semipenetrans, Xiphinema* spp., e.g. *Xiphinema index.*

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*Mycoplasma*-like organisms) and RLO (*Rickettsia*-like organisms). They can, as the case may be, also be used as intermediates or precursors for the synthesis of other active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers 173, prepared by the FAO/WHO Joint Meeting on Pesticide Specifications, 2004, ISBN: 9251048576. The formulations, in addition to one or more compounds of the formula (I), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), the esters (including fats and oils) and (poly)ethers, the simple and substituted amines, amides, lactams (such as N-alkylpyrrolidones) and lactones, the sulfones and sulfoxides (such as dimethyl sulfoxide), the carbonates and the nitriles.

If the extender used is water, it is also possible to employ, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, carbonates such as propylene carbonate, butylene carbonate, diethyl carbonate or dibutyl carbonate, or nitriles such as acetonitrile or propanenitrile.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents such as dimethyl sulfoxide, carbonates such as propylene carbonate, butylene carbonate, diethyl carbonate or dibutyl carbonate, nitriles such as acetonitrile or propanenitrile, and also water.

In principle, it is possible to use all suitable carriers. Suitable carriers include more particularly the following: e g ammonium salts and natural, finely ground rocks, such as kaolins, aluminas, talc, chalk, quartz, attapulgite, montmorillonite or diatomaceous earth, and synthetic, finely ground rocks, such as finely divided silica, aluminium oxide and natural or synthetic silicates, resins, waxes and/or solid fertilizers. It is likewise possible to use mixtures of such carriers. Useful carriers for granules include:

for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), isethionate derivatives, phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam formers or antifoams may also be present.

In addition, the formulations and use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence to increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. The compounds are employed in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active compounds specified here with their common names are known and are described for example in "*The Pesticide Manual*", 16th ed., British Crop Protection Council 2012, or can be searched for on the Internet (e.g. http//www.alanwood.net/pesticides). The classification is based on the IRAC Mode of Action Classification Scheme applicable at the time of filing of this patent application.

(1) Acetylcholinesterase (AChE) inhibitors, preferably carbamates selected from alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates selected from acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, preferably cyclodiene-organochlorines selected from chlordane and endosulfan or phenylpyrazoles (fiproles) selected from ethiprole and fipronil.

(3) Sodium channel modulators, preferably pyrethroids selected from acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Competitive modulators of the nicotinic acetylcholine receptor (nAChR), preferably neonicotinoids selected from acetamiprid, clothianidin, dinotefuran, imidacloprid, nitenpyram, thiacloprid and thiamethoxam, or nicotine, or sulfoximines selected from sulfoxaflor, or butenolides selected from flupyradifurone.

(5) Nicotinic acetylcholine receptor (nAChR) allosteric modulators, preferably spinosyns selected from spinetoram and spinosad.

(6) Glutamate-gated chloride channel (GluCl) allosteric modulators, preferably avermectins/milbemycins selected from abamectin, emamectin benzoate, lepimectin and milbemectin.

(7) Juvenile hormone mimetics, preferably juvenile hormone analogues selected from hydroprene, kinoprene and methoprene or fenoxycarb or pyriproxyfen.

(8) Miscellaneous non-specific (multi-site) inhibitors, preferably alkyl halides selected from methyl bromide and other alkyl halides; or chloropicrin or sulfuryl fluoride or borax or tartar emetic or methyl isocyanate generators selected from diazomet and metam.

(9) TRPV channel modulators of chordotonal organs selected from pymetrozine and pyrifluquinazon.

(10) Mite growth inhibitors selected from clofentezine, hexythiazox, diflovidazin and etoxazole.

(11) Microbial disruptors of the insect gut membrane selected from *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and B.t. plant proteins selected from Cry1Ab, Cry1Ac, Cry1Fa, Cry1A.105, Cry2Ab, VIP3A, mCry3A, Cry3Ab, Cry3Bb and Cry34Ab1/35Ab1.

(12) Inhibitors of mitochondrial ATP synthase, preferably ATP disruptors selected from diafenthiuron or organotin compounds selected from azocyclotin, cyhexatin and fenbutatin oxide, or propargite or tetradifon.

(13) Uncouplers of oxidative phosphorylation via disruption of the proton gradient selected from chlorfenapyr, DNOC and sulfluramid.

(14) Nicotinic acetylcholine receptor channel blockers selected from bensultap, cartap hydrochloride, thiocyclam, and thiosultap-sodium.

(15) Inhibitors of chitin biosynthesis, type 0, selected from bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, selected from buprofezin.

(17) Moulting disruptors (especially in the case of Diptera) selected from cyromazine.

(18) Ecdysone receptor agonists selected from chromafenozide, halofenozide, methoxyfenozide and tebufenozide.

(19) Octopamine receptor agonists selected from amitraz.

(20) Mitochondrial complex III electron transport inhibitors selected from hydramethylnon, acequinocyl and fluacrypyrim.

(21) Mitochondrial complex I electron transport inhibitors, preferably METI acaricides selected from fenazaquin, fenpyroximate, pyrimidifen, pyridaben, tebufenpyrad and tolfenpyrad, or rotenone (Derris).

(22) Voltage-dependent sodium channel blockers selected from indoxacarb and metaflumizone.

(23) Inhibitors of acetyl-CoA carboxylase, preferably tetronic and tetramic acid derivatives selected from spirodiclofen, spiromesifen and spirotetramat.

(24) Mitochondrial complex IV electron transport inhibitors, preferably phosphines selected from aluminium phosphide, calcium phosphide, phosphine and zinc phosphide, or cyanides selected from calcium cyanide, potassium cyanide and sodium cyanide.

(25) Mitochondrial complex II electron transport inhibitors, preferably beta-keto nitrile derivatives selected from cyenopyrafen and cyflumetofen, or carboxanilides selected from pyflubumide.

(28) Ryanodine receptor modulators, preferably diamides selected from chlorantraniliprole, cyantraniliprole and flubendiamide (29) Modulators of chordotonal organs (with undefined target structure) selected from flonicamid.

(30) Further active compounds selected from acynonapyr, afidopyropen, afoxolaner, azadirachtin, benclothiaz, benzoximate, benzpyrimoxan, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, flupyrimin, fluralaner, fluxametamide, fufenozide, guadipyr, heptafluthrin, imidaclothiz, iprodione, kappa bifenthrin, kappa tefluthrin, lotilaner, meperfluthrin, oxazosulfyl, paichongding, pyridalyl, pyrifluquinazon, pyriminostrobin, spirobudiclofen, spiropidion, tetramethylfluthrin, tetraniliprole, tetrachlorantraniliprole, tigolaner, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO 2006/043635) (CAS 885026-50-6), {[(2E)-3-(4-chlorophenyl)prop-2-en-1-yl]-5-fluorospiro[indole-3,4'-piperidine]-1 (2H)-yl}(2-chloropyridin-4-yl)methanone (known from WO 2003/106457) (CAS 637360-23-7), 2-chloro-N-[2-{1-[(2E)-3-(4-chlorophenyl) prop-2-en-1-yl]piperidin-4-yl}-4-(trifluoromethyl)phenyl] isonicotinamide (known from WO 2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO 2004/099160) (CAS 792914-58-0), PF1364 (known from JP2010/018586) (CAS Reg. No. 1204776-60-2), (3E)-3-[1-[(6-chloro-3-pyridyl)methyl]-2-pyridylidene]-1,1,1-trifluoropropan-2-one (known from WO 2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO 2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl] amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide (Liudaibenjiaxuanan, known from CN 103109816 A) (CAS 1232543-85-9); N-[4-chloro-2-[[(1,1-dimethylethyl)amino] carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy] phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio] phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]pyrimidine (known from WO 2013/115391 A1) (CAS 1449021-97-9), 3-(4-chloro-2,6-dimethylphenyl)-8-methoxy-1-methyl-1,8-diazaspiro[4.5] decane-2,4-dione (known from WO 2014/187846 A1) (CAS 1638765-58-8), ethyl 3-(4-chloro-2,6-dimethylphenyl)-8- methoxy-1-methyl-2-oxo-1,8-diazaspiro[4.5]dec-3-en-4-yl-carboxylate (known from WO 2010/066780 A1, WO 2011/151146 A1) (CAS 1229023-00-0), 4-[(5S)-5-(3,5-dichloro-4-fluorophenyl)-4,5-dihydro-5-(trifluoromethyl)-3-isoxazolyl]-N-[(4R)-2-ethyl-3-oxo-4-isoxazolidinyl]-2-methylbenzamide (known from WO 2011/067272, WO 2013/050302) (CAS 1309959-62-3).

Fungicides

The active compounds specified herein by their common name are known and described, for example, in "Pesticide Manual" (16th Ed. British Crop Protection Council) or searchable on the Internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Inhibitors of ergosterol biosynthesis, for example (1.001) cyproconazole, (1.002) difenoconazole, (1.003) epoxiconazole, (1.004) fenhexamide, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazole, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2 S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055)-2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)ox)]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1 S)-1-(3,5-difluorophenyl) ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3 S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3 S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3 S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy) methyl]phenyl}-2-(methoxyimino)-N-methylacetamide, (3.022) (2E,3Z)-5-{[1-(4-chlorophenyl)-1H-pyrazol-3-yl] oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2 S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy) methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5- phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multi-site activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium poly sulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defense, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxy phenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({

[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6[({[(1-methyl-1H-tetrazol-5-yl) (phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SCI (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., insbesondere *Rhizobium trifolii, Rhizopogon* spp., *Sclerorma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, *Quassia amara, Quercus, Quillaja, Regalia*, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The treatment according to the invention of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain active herbicidal compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants, or by drip application (frequently also referred to as "chemigation"), meaning that the compounds of the formula (I) according to the invention are introduced via surface or underground drip lines over certain periods of time together with varying amounts of water at defined locations in the vicinity of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus*, *Rhizobium*, *Pseudomonas*, *Serratia*, *Trichoderma*, *Clavibacter*, *Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants especially include ethylene oxide/propylene oxide block polymers, alkylphenol poly glycol ethers and tristyrylphenol polyglycol ethers, and the phosphated or sulfated derivatives thereof. Suitable anionic dispersants are especially ligno-sulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example *Haematopinus* spp., *Linognathus* spp., *Pediculus* spp., *Phtirus* spp., *Solenopotes* spp.;

from the order of Mallophagida and the suborders Amblycerina and Ischnocerina, for example *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hyporma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example *Ceratophyllus* spp., *Ctenocephalides* spp., *Pulex* spp., *Tunga* spp., *Xenopsylla* spp.;

from the order of Heteropterida, for example *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example Giardia spp., *Spironucleus* spp.

Parabasala: from the order of Trichomonadida, for example *Histomonas* spp., *Pentatrichomonas* spp., *Tetratrichomonas* spp., *Trichomonas* spp., *Tritrichomonas* spp.

Euglenozoa: from the order of Trypanosomatida, for example *Leishmania* spp., *Trypanosoma* spp.

Sarcomastigophora (Rhizopoda) such as Entamoebidae, for example *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order Eimeriida, for example *Besnoitia* spp., *Cystoisospora* spp., *Eimeria* spp., *Hammondia* spp., *Isospora* spp., *Neospora* spp., *Sarcocystis* spp., *Toxoplasma* spp.; from the order Adeleida e.g. *Hepatozoon* spp., *Klossiella* spp.; from the order Haemosporida e.g. *Leucocytozoon* spp., *Plasmodium* spp.; from the order Piroplasmida e.g. *Babesia* spp., *Ciliophora* spp., *Echinozoon* spp., *Theileria* spp.; from the order Vesibuliferida e.g. *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminths (e.g. Monogenea, cestodes and trematodes).

Illustrative helminths include, but are not limited to:

Monogenea: e.g.: *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp. *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hyporaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of the Polymorphida, for example *Filicollis* spp.; from the order Echinorhynchida, for example *Acanthocephalus* spp., *Echinorhynchus* spp., *Leptorhynchoides* spp.

Pentastoma: from the order of Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention refers to the compounds of the formula (I) for use as a medicament.

A further aspect relates to the compounds of the formula (I) for use as an antiendoparasitic agent.

A further specific aspect of the invention relates to the compounds of the formula (I) for use as an antihelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active compounds, especially with endo- and ectoparasiticides, are provided for the field of veterinary medicine.

In the field of animal health, "mixture" means not just that two (or more) different active compounds are formulated in a common formulation and are correspondingly employed together, but also relates to products comprising formulations separated for each active compound. Accordingly, when more than two active compounds are to be employed, all active compounds can be formulated in a common formulation or all active compounds can be formulated in separate formulations; likewise conceivable are mixed forms in which some of the active compounds are formulated together and some of the active compounds are formulated separately. Separate formulations allow the separate or successive application of the active compounds in question.

The active compounds specified here by their "common names" are known and are described, for example, in the "Pesticide Manual" (see above) or can be searched for on the Internet (e.g.: http://www.alanwood.net/pesticides).

Illustrative active compounds from the group of the ectoparasiticides as mixing components, without any intention that this should constitute a restriction, include the insecticides and acaricides listed in detail above. Further usable active compounds are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active compounds having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, tigolaner, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron;

amidine derivatives, e.g. chlormebuform, cymiazole, demiditraz beehive *Varroa* acaricides, for example organic acids, e.g. formic acid, oxalic acid.

Illustrative active compounds from the group of the endoparasiticides, as mixing components, include, but are not limited to, active anthelmintic ingredients and active antiprotozoic ingredients.

The active anthelmintic ingredients include but are not limited to the following active nematicidal, trematicidal and/or cestocidal ingredients:

from the class of the macrocyclic lactones, for example; eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example; oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example morantel, pyrantel, oxantel;

from the class of the imidazothiazoles, for example: butamisole, levamisole, tetramisole;

from the class of the aminophenylamidines, for example; amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example tribromsalan, bromoxanide, brotianide, clioxanide, closantel, niclosamide, oxyclozanide, rafoxanide;

from the class of the substituted phenols, for example; nitroxynil, bithionol, disophenol, hexachlorophen, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example; praziquantel, epsiprantel;

from the class of the piperazines, for example: piperazine, hydroxyzine;

from the class of the tetracyclines, for example; tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include, but are not limited to, the following active compounds:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example enrofloxacin, pradofloxacin;

from the class of the quinines, for example: chloroquin;

from the class of the pyrimidines, for example: pyrimethamine;

from the class of the sulfonamides, for example: sulfaquinoxaline, trimethoprim, sulfaclozin;

from the class of the thiamines, for example amprolium;

from the class of the lincosamides, for example clindamycin;

from the class of the carbanilides, for example; imidocarb;

from the class of the nitrofurans, for example nifurtimox;

from the class of the quinazolinone alkaloids, for example: halofuginone;

from various other classes, for example oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, filariasis, other viral diseases, transmission of other worms;

*Aedes*: yellow fever, dengue fever, further viral disorders, filariasis;

Simuliidae: transmission of worms, especially *Onchocerca volvulus*;

Psychodidae: transmission of leishmaniasis

2) Lice: skin infections, epidemic typhus;

3) Fleas: plague, endemic typhus, tapeworms;

4) Flies: sleeping sickness (trypanosomiasis); cholera, other bacterial diseases;

5) Mites: acariosis, epidemic typhus, Rickettsialpox, tularaemia, Saint Louis encephalitis, tick-borne encephalitis (TBE), Crimean-Congo haemorrhagic fever, borreliosis;

6) Ticks: borrelioses such as *Borrelia bungdorferi* sensu lato., *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *Thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus*, A. dims (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is carried out, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Ethyl 2-bromo-1-methyl-1H-imidazole-4-carboxylate
(III-1)

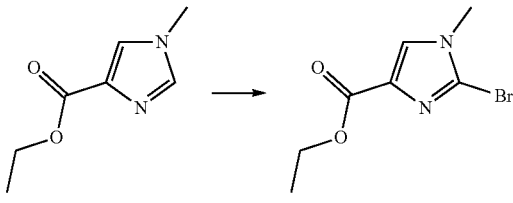

30.0 g (195 mmol) of ethyl 1-methyl-1H-imidazole-4-carboxylate were dissolved in 1.0 l of tetrahydrofuran and cooled to 0° C. To this solution 34.5 g (195 mmol) of N-bromosuccinimide were added a little at a time, and the reaction mixture was stirred at room temperature overnight. The reaction was terminated by the addition of saturated sodium thiosulfate solution ($Na_2S_2O_3$), and 800 ml of ethyl acetate were added. The phases were separated and the aqueous phase was extracted three times with 800 ml of ethyl acetate each time. The organic phases were combined, dried over sodium sulfate and filtered. The solvent was distilled off under reduced pressure and the residue was purified by column chromatography purification using a petroleum ether/ethyl acetate gradient (3:1) as mobile phase.

$^1$H-NMR (300 MHz, $d_6$-DMSO) δ ppm: 1.26 (t, 3H), 3.64 (s, 3H), 4.22 (q, 2H), 8.07 (s, 1H).

2-Bromo-5-(ethylsulfanyl)-1-methyl-1H-imidazole-4-carboxylic acid (X-1)

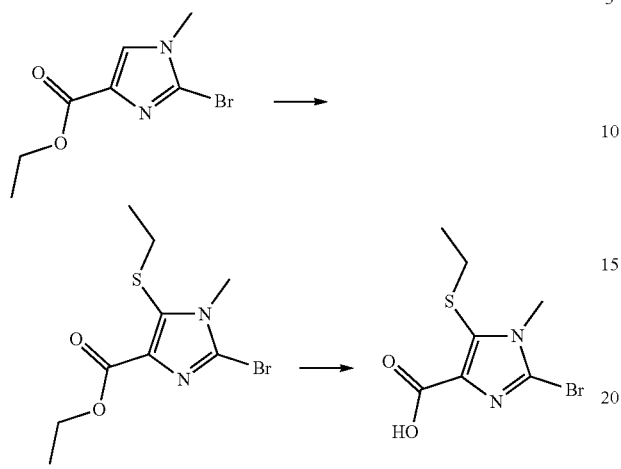

31.0 g (134 mmol) of ethyl 2-bromo-1-methyl-1H-imidazole-4-carboxylate and 24.4 g (200 mmol) of diethyl disulfide were dissolved in 620 ml of tetrahydrofuran and cooled to 78° C. To this solution were added dropwise 100 ml (2M in THF, 200 mmol) of lithium diisopropylamide (LDA) and the reaction mixture was stirred at 78° C. for 30 minutes. The reaction was terminated by adding saturated ammonium chloride solution. The phases were separated and the aqueous phase was extracted three times with 300 ml of ethyl acetate each time. The organic phases were combined, dried over magnesium sulfate and filtered. The solvent was distilled off under reduced pressure and the residue was purified by column chromatography purification using a petroleum ether/ethyl acetate gradient as mobile phase. This gave 28.5 g (97.3 mmol) of ethyl 2-bromo-5-(ethylsulfanyl)-1-methyl-1H-imidazole-4-carboxylate. This was dissolved in 300 ml of methanol and the solution was cooled to 0° C. 300 ml (2N in water, 600 mmol) of sodium hydroxide were then added and the mixture was stirred at room temperature for 1 h. The mixture was concentrated on a rotary evaporator and neutralized by adding 1N HCl. The mixture was extracted with ethyl acetate. The solvent was distilled off under reduced pressure and the target compound was obtained.

$^1$H-NMR (300 MHz, $d_6$-DMSO) δ ppm: 1.09 (t, 3H), 2.86 (q, 2H), 3.64 (s, 3H), 12.60 (s, 1H).

2-[2-Bromo-5-(ethylsulfanyl)-1-methyl-1H-imidazol-4-yl]-3-methyl-6-(trifluoromethyl)-3 11-imidazo[4,5-b]pyridine (XI-1)

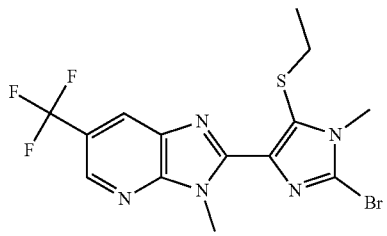 [SMILES: CCSc1c(-c2nc3cc(C(F)(F)F)cnc3n2C)nc(Br)n1C]

To a solution of 4.99 g (18.8 mmol) of 2-bromo-5-(ethylsulfanyl)-1-methyl-1H-imidazole-4-carboxylic acid in 30.5 ml of pyridine were added 3.00 g (15.7 mmol) of $N^2$-methyl-5-(trifluoromethyl)pyridine-2,3-diamine and 6.02 g (31.4 mmol) of 1-(3-dimethylaminopropyl)-3-ethyl-carbodiimide hydrochloride (EDCI). The mixture was stirred at 120° C. overnight. Subsequently, the reaction mixture was cooled to room temperature. The mixture was freed of the solvent under reduced pressure. The residue was purified on RP18 by HPLC using the mobile phase acetonitrile/water+0.1% formic acid.

$^1$H-NMR (400 MHz, $d_6$-DMSO) δ ppm: 1.115 (t, 3H), 3.02 (q, 2H), 3.76 (s, 3H), 4.06 (s, 3H), 8.535 (s, 1H), 8.77 (s, 1H).

2-[2-Bromo-5-(ethylsulfonyl)-1-methyl-1H-imidazol-4-yl]-3-methyl-6-(trifluoromethyl)-311-imidazo[4,5-b]pyridine (XI-2)

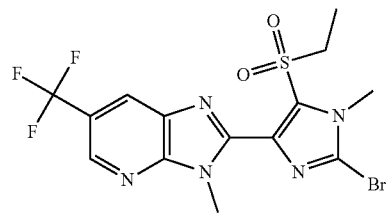 [SMILES: CCS(=O)(=O)c1c(-c2nc3cc(C(F)(F)F)cnc3n2C)nc(Br)n1C]

3.22 g (7.66 mmol) of 2-[2-bromo-5-(ethylsulfanyl)-1-methyl-1H-imidazol-4-yl]-3-methyl-6-(trifluoromethyl)-3H-imidazo[4,5-b]pyridine were dissolved in 2.0 ml of dichloromethane, at room temperature, 1.45 ml (38.3 mmol) of formic acid and 5.21 g (53.6 mmol) of hydrogen peroxide were added and the mixture was then stirred at room temperature for 18 h. The mixture was freed of the solvent under reduced pressure. The solution was then diluted by addition of dichloromethane and washed with saturated sodium thiosulfate solution. The organic phase was removed, dried over sodium sulfate and filtered. The solvent was distilled off under reduced pressure.

$^1$H-NMR (400 MHz, $d_6$-DMSO) δ ppm: 1.29 (t, 3H), 3.76 (q, 2H), 3.86 (s, 3H), 3.93 (s, 3H), 8.62 (s, 1H), 8.85 (s, 1H).

2-[5-(Ethylsulfonyl)-1-methyl-2-vinyl-1H-imidazol-4-yl]-3-methyl-6-(trifluoromethyl)-3H-imidazo[4,5-b]pyridine (XII-1)

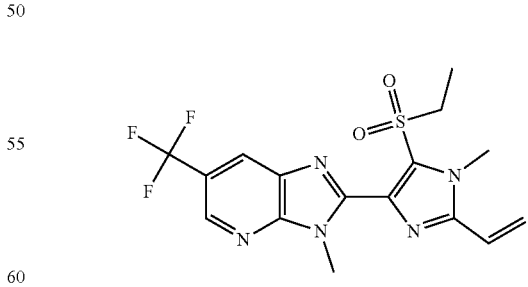

A solution of 624 mg (1.37 mmol) of 2-[2-bromo-5-(ethylsulfonyl)-1-methyl-1H-imidazol-4-yl]-3-methyl-6-(trifluoromethyl)-3H-imidazo[4,5-b]pyridine and 697 mg (2.20 mmol) of tributyl(vinyl)stannane in 2.9 ml of N,N-dimethylformamide was degassed with argon. 14.5 mg (0.021 mmol) of palladiumbis(triphenylphosphine) dichloride were added and the solution was stirred at 75° C. for 4 hours. The mixture was concentrated. The residue was purified on silica gel by MPLC using the mobile phase cyclohexane/ethyl acetate.

¹H-NMR (400 MHz, d₆-DMSO) δ ppm: 1.27 (t, 3H), 3.72 (q, 2H), 3.87 (s, 3H), 3.98 (s, 3H), 5.77 (dd, 1H), 6.36 (dd, 1H), 7.01 (dd, 1H), 8.60 (s, 1H), 8.84 (s, 1H).

2-[2-(3-Cyclopropyl-4,5-dihydro-1,2-oxazol-5-yl)-5-(ethylsulfonyl)-1-methyl-1H-imidazol-4-yl]-3-methyl-6-(trifluoromethyl)-3H-imidazo[4,5-b]pyridine (I-1)

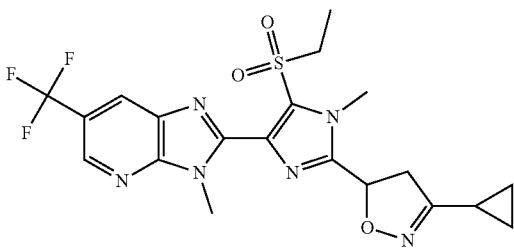 [SMILES: CCS(=O)(=O)c1c(-c2nc3cc(C(F)(F)F)cnc3n2C)nc(C2CC(C3CC3)=NO2)n1C]

A solution of 107 mg (1.25 mmol) of N-(cyclopropylmethylene)hydroxylamine, 167 mg (1.25 mmol) of N-chlorosuccinimide and 10.1 μl (0.125 mmol) of pyridine was stirred at room temperature for 4.5 hours. 100 mg (0.250 mmol) of 2-[5-(ethylsulfonyl)-1-methyl-2-vinyl-1H-imidazol-4-yl]-3-methyl-6-(trifluoromethyl)-3H-imidazo[4,5-b]pyridine and 0.174 ml (1.25 mmol) of triethylamine were added and the solution was stirred at room temperature for 18 hours. The mixture was extracted with water/dichloromethane. The organic phase was dried over sodium sulfate, filtered and concentrated. The residue was purified on silica gel by MPLC using the mobile phase cyclohexane/ethyl acetate. The desired fraction was purified on RP18 by HPLC using the mobile phase acetonitrile/water.

log P[acidic]: 2.73; log P[neutral]: 2.72; MH⁺: 483; ¹H-NMR (400 MHz, d₆-DMSO) δ ppm: 0.83 (m, 2H), 0.90 (m, 2H), 1.27 (t, 3H), 1.86 (m, 1H), 3.28 (dd, 1H), 3.60 (dd, 1H), 3.79 (m, 2H), 3.86 (s, 3H), 3.98 (s, 3H), 5.91 (dd, 1H), 8.60 (s, 1H), 8.84 (s, 1H).

1-(4-{5-(Ethylsulfonyl)-1-methyl-4-[3-methyl-6-(trifluoromethyl)-3H-imidazo[4,5-b]pyridin-2-yl]-1H-imidazol-2-yl}phenyl)cyclopropanecarbonitrile (I-5)

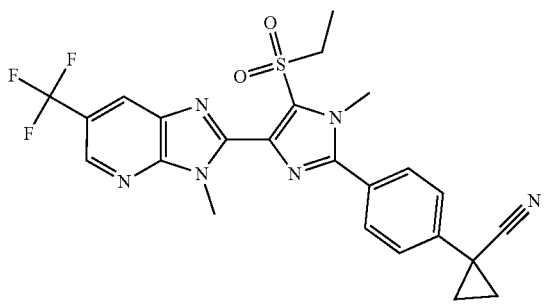 [SMILES: CCS(=O)(=O)c1c(-c2nc3cc(C(F)(F)F)cnc3n2C)nc(-c2ccc(C3(C#N)CC3)cc2)n1C]

A solution of 150 mg (0.332 mmol) of 2-[2-bromo-5-(ethylsulfonyl)-1-methyl-1H-imidazol-4-yl]-3-methyl-6-(trifluoromethyl)-3H-imidazo[4,5-b]pyridine, 268 mg (0.995 mmol) of 1-[4-(4,4,5,5-tetramethyl-1,3,2-dioxaborolan-2-yl)phenyl]cyclopropanecarbonitrile and 324 mg (0.995 mmol) of caesium carbonate in 2.5 ml of 1,4-dioxane and 0.55 ml of water was degassed with argon. 38.2 mg (0.033 mmol) of tetrakis(triphenylphosphine)palladium were added and the solution was stirred at 110° C. in a microwave for 30 min. The mixture was concentrated. The residue was purified on RP18 by HPLC using the mobile phase acetonitrile/water.

log P[acidic]: 3.14; log P[neutral]: 3.07; MW: 515; ¹H-NMR (400 MHz, d₆-DMSO) δ ppm: 1.33 (t, 3H), 1.64 (m, 2H), 1.86 (m, 2H), 3.83 (q, 2H), 3.91 (s, 3H), 3.965 (s, 3H), 7.54 (d, 2H), 7.85 (d, 2H), 8.61 (s, 1H), 8.85 (s, 1H).

2-[2-(3-Cyclopropyl-1H-pyrazol-1-yl)-5-(ethylsulfonyl)-1-methyl-1H-imidazol-4-yl]-3-methyl-6-(trifluoromethyl)-3H-imidazo[4,5-b]pyridine (I-9)

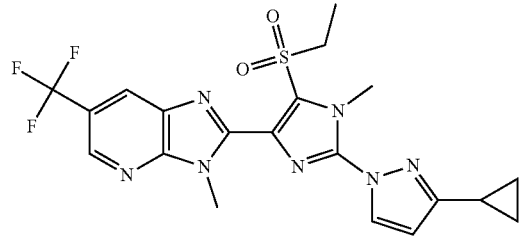 [SMILES: CCS(=O)(=O)c1c(-c2nc3cc(C(F)(F)F)cnc3n2C)nc(-n2ccc(C3CC3)n2)n1C]

A solution of 100 mg (0.221 mmol) of 2-[2-bromo-5-(ethylsulfonyl)-1-methyl-1H-imidazol-4-yl]-3-methyl-6-(trifluoromethyl)-3H-imidazo[4,5-b]pyridine, 167 mg (1.25 mmol) of N-chlorosuccinimide and 30.6 mg (0.221 mmol) of potassium carbonate was stirred at 95° C. for 18 hours. The mixture was concentrated. The residue was purified on RP18 by HPLC using the mobile phase acetonitrile/water. The residue was purified on RP18 by HPLC using the mobile phase acetonitrile/water+0.1% formic acid.

log P[acidic]: 3.46; log P[neutral]: 3.36; MW: 480; ¹H-NMR (400 MHz, d₆-DMSO) δ ppm: 0.81 (m, 2H), 0.995 (m, 2H), 1.31 (t, 3H), 2.04 (m, 1H), 3.80 (q, 2H), 3.89 (s, 3H), 4.03 (s, 3H), 6.40 (d, 1H), 8.26 (d, 1H), 8.63 (m, 1H), 8.85 (m, 1H).

In analogy to the examples and according to the above-described preparation processes, the following compounds of the formula (I) can be obtained:

| Example | Structure |
|---|---|
| I-1 | 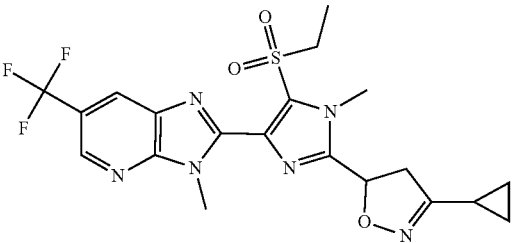 [SMILES: CCS(=O)(=O)c1c(-c2nc3cc(C(F)(F)F)cnc3n2C)nc(C2CC(C3CC3)=NO2)n1C] |
| I-2 | 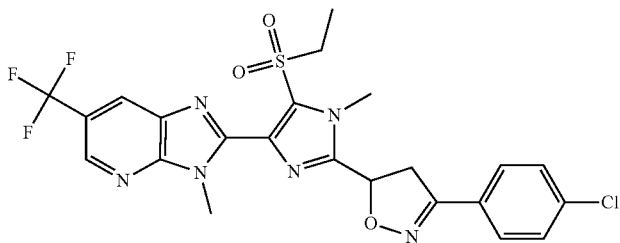 [SMILES: CCS(=O)(=O)c1c(-c2nc3cc(C(F)(F)F)cnc3n2C)nc(C2CC(c3ccc(Cl)cc3)=NO2)n1C] |
| I-3 | 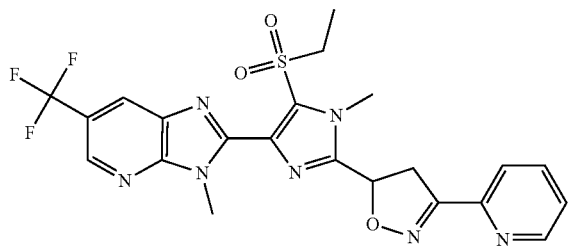 [SMILES: CCS(=O)(=O)c1c(-c2nc3cc(C(F)(F)F)cnc3n2C)nc(C2CC(c3ccccn3)=NO2)n1C] |
| I-4 | 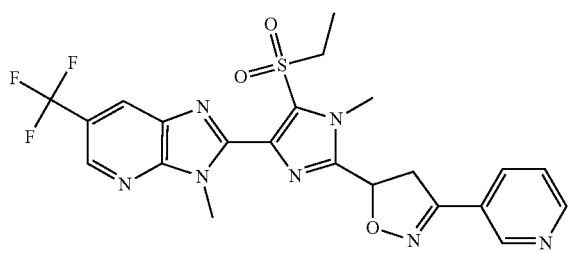 [SMILES: CCS(=O)(=O)c1c(-c2nc3cc(C(F)(F)F)cnc3n2C)nc(C2CC(c3cccnc3)=NO2)n1C] |
| I-5 | 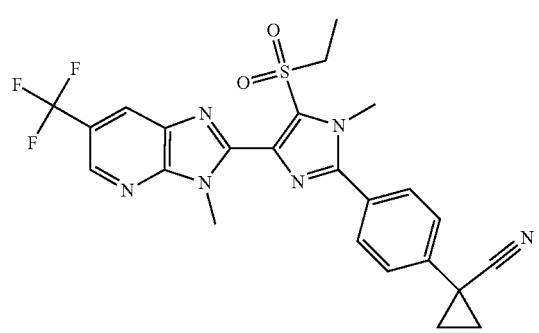 [SMILES: CCS(=O)(=O)c1c(-c2nc3cc(C(F)(F)F)cnc3n2C)nc(-c2ccc(C3(C#N)CC3)cc2)n1C] |
| I-6 | 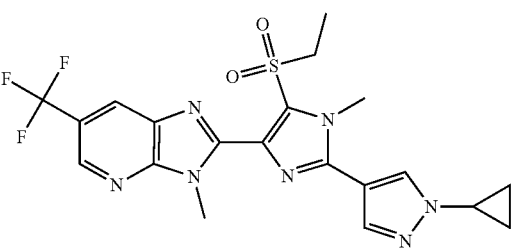 [SMILES: CCS(=O)(=O)c1c(-c2nc3cc(C(F)(F)F)cnc3n2C)nc(-c2cnn(C3CC3)c2)n1C] |

-continued

| Example | Structure |
|---------|-----------|
| I-7 | 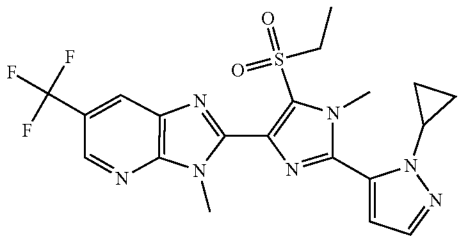 [SMILES: CCS(=O)(=O)c1c(-c2nc3cc(C(F)(F)F)cnc3n2C)nc(-c2ccnn2C2CC2)n1C] |
| I-8 | 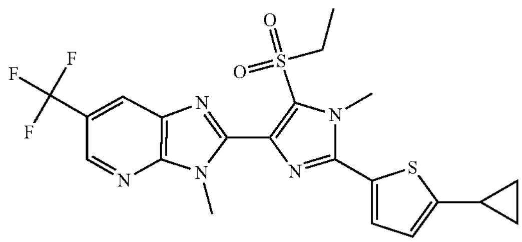 [SMILES: CCS(=O)(=O)c1c(-c2nc3cc(C(F)(F)F)cnc3n2C)nc(-c2ccc(C3CC3)s2)n1C] |
| I-9 | 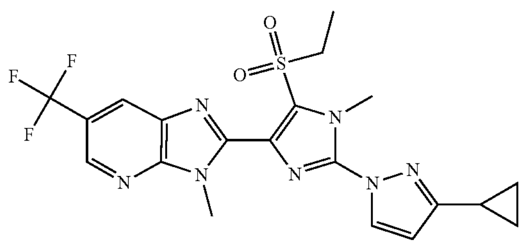 [SMILES: CCS(=O)(=O)c1c(-c2nc3cc(C(F)(F)F)cnc3n2C)nc(-n2ccc(C3CC3)n2)n1C] |
| I-10 | 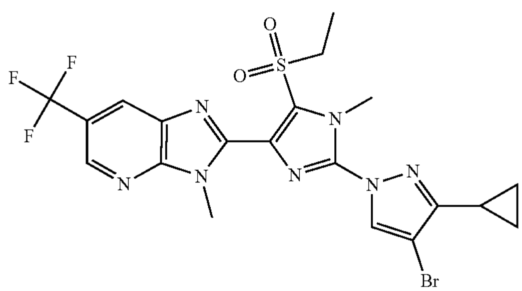 [SMILES: CCS(=O)(=O)c1c(-c2nc3cc(C(F)(F)F)cnc3n2C)nc(-n2cc(Br)c(C3CC3)n2)n1C] |
| I-11 | 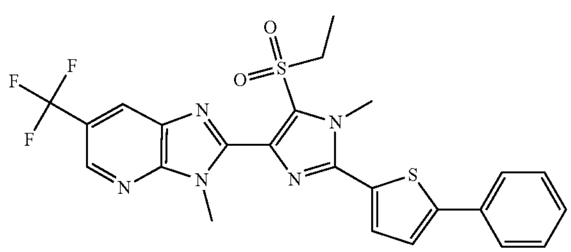 [SMILES: CCS(=O)(=O)c1c(-c2nc3cc(C(F)(F)F)cnc3n2C)nc(-c2ccc(-c3ccccc3)s2)n1C] |
| I-12 | 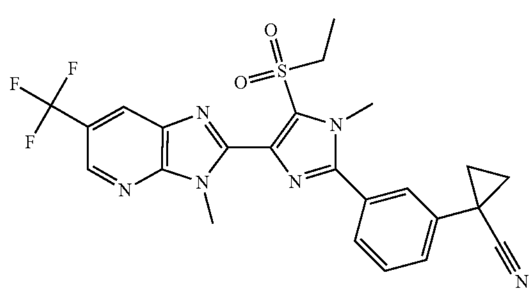 [SMILES: CCS(=O)(=O)c1c(-c2nc3cc(C(F)(F)F)cnc3n2C)nc(-c2cccc(C3(C#N)CC3)c2)n1C] |

| Example | Structure |
|---|---|
| I-13 | 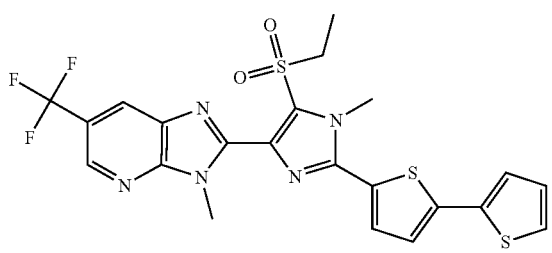 [SMILES: CCS(=O)(=O)c1c(-c2nc3cc(C(F)(F)F)cnc3n2C)nc(-c2ccc(-c3cccs3)s2)n1C] |
| I-14 | 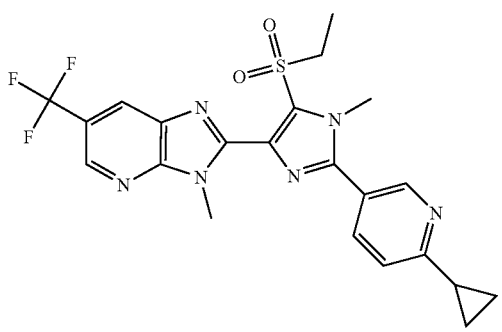 [SMILES: CCS(=O)(=O)c1c(-c2nc3cc(C(F)(F)F)cnc3n2C)nc(-c2ccc(C3CC3)nc2)n1C] |
| I-15 | 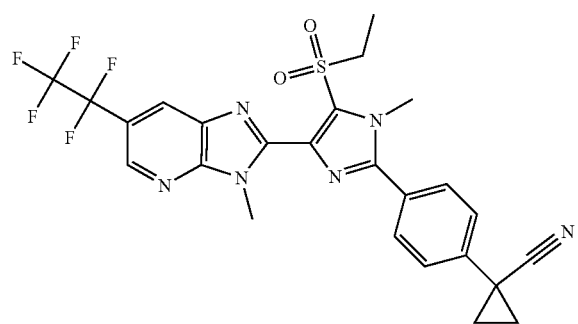 [SMILES: CCS(=O)(=O)c1c(-c2nc3cc(C(F)(F)C(F)(F)F)cnc3n2C)nc(-c2ccc(C3(C#N)CC3)cc2)n1C] |
| I-16 | 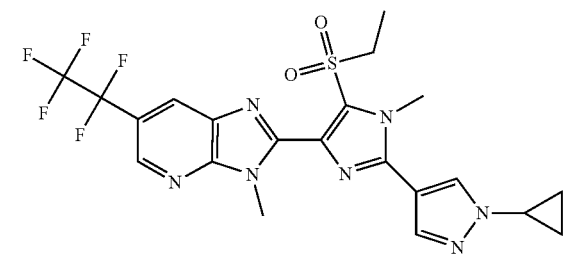 [SMILES: CCS(=O)(=O)c1c(-c2nc3cc(C(F)(F)C(F)(F)F)cnc3n2C)nc(-c2cnn(C3CC3)c2)n1C] |
| I-17 | 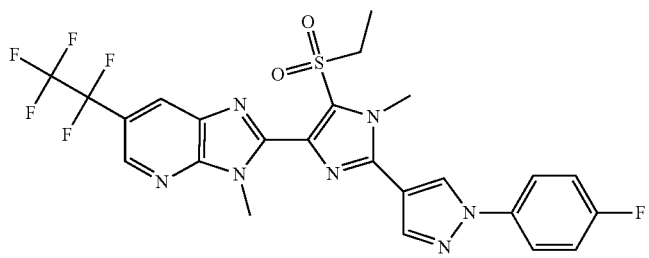 [SMILES: CCS(=O)(=O)c1c(-c2nc3cc(C(F)(F)C(F)(F)F)cnc3n2C)nc(-c2cnn(-c3ccc(F)cc3)c2)n1C] |

| Example | Structure |
|---|---|
| I-18 | 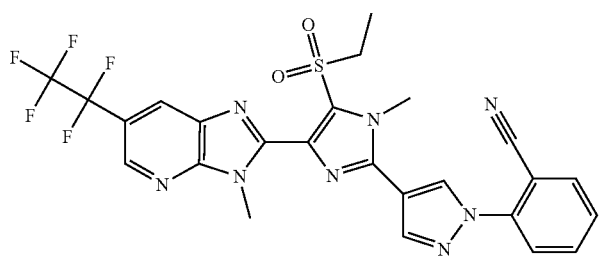 [SMILES: CCS(=O)(=O)c1c(-c2nc3cc(C(F)(F)C(F)(F)F)cnc3n2C)nc(-c2cnn(-c3ccccc3C#N)c2)n1C] |
| I-19 | 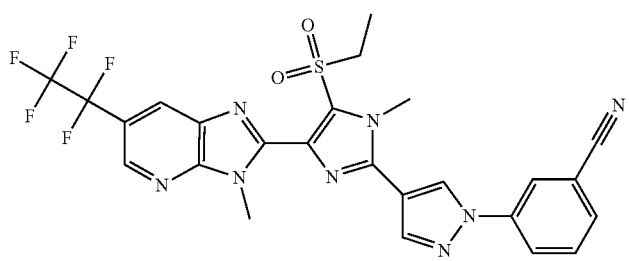 [SMILES: CCS(=O)(=O)c1c(-c2nc3cc(C(F)(F)C(F)(F)F)cnc3n2C)nc(-c2cnn(-c3cccc(C#N)c3)c2)n1C] |
| I-20 | 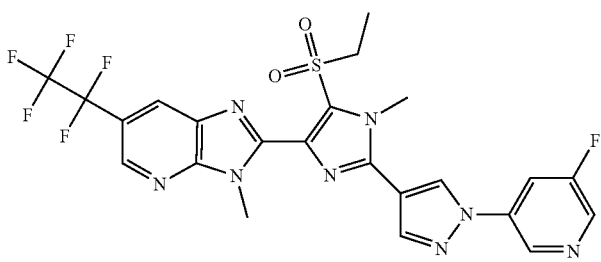 [SMILES: CCS(=O)(=O)c1c(-c2nc3cc(C(F)(F)C(F)(F)F)cnc3n2C)nc(-c2cnn(-c3cncc(F)c3)c2)n1C] |
| I-21 | 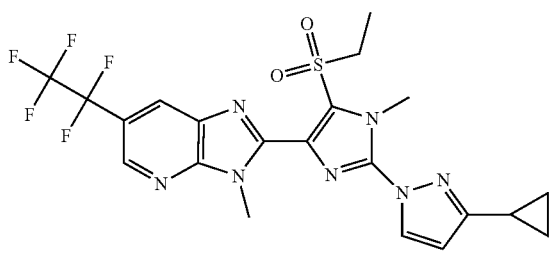 [SMILES: CCS(=O)(=O)c1c(-c2nc3cc(C(F)(F)C(F)(F)F)cnc3n2C)nc(-n2ccc(C3CC3)n2)n1C] |
| I-22 | 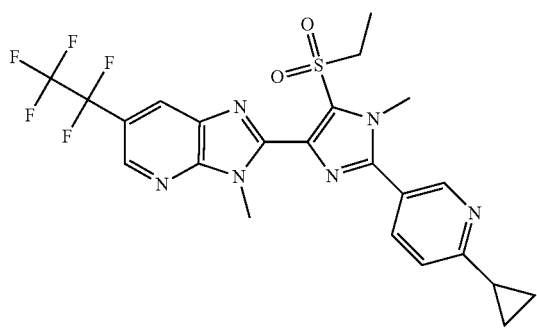 [SMILES: CCS(=O)(=O)c1c(-c2nc3cc(C(F)(F)C(F)(F)F)cnc3n2C)nc(-c2ccc(C3CC3)nc2)n1C] |

| Example | Structure |
|---|---|
| I-23 | 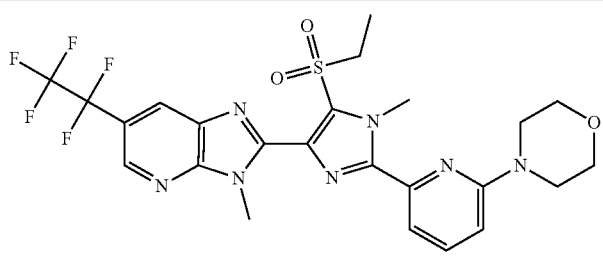 [SMILES: CCS(=O)(=O)c1c(-c2nc3cc(C(F)(F)C(F)(F)F)cnc3n2C)nc(-c2cccc(N3CCOCC3)n2)n1C] |
| I-24 | 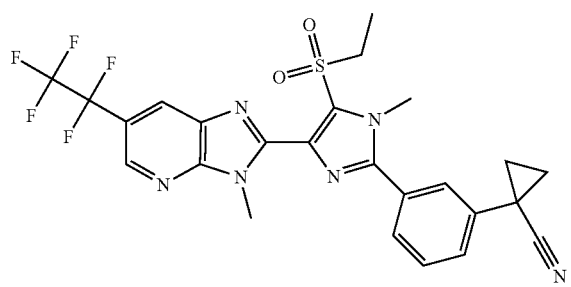 [SMILES: CCS(=O)(=O)c1c(-c2nc3cc(C(F)(F)C(F)(F)F)cnc3n2C)nc(-c2cccc(C3(C#N)CC3)c2)n1C] |
| I-25 | 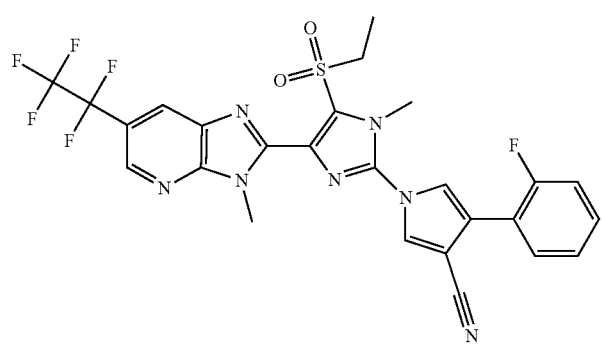 [SMILES: CCS(=O)(=O)c1c(-c2nc3cc(C(F)(F)C(F)(F)F)cnc3n2C)nc(-n2cc(C#N)c(-c3ccccc3F)c2)n1C] |
| I-26 | 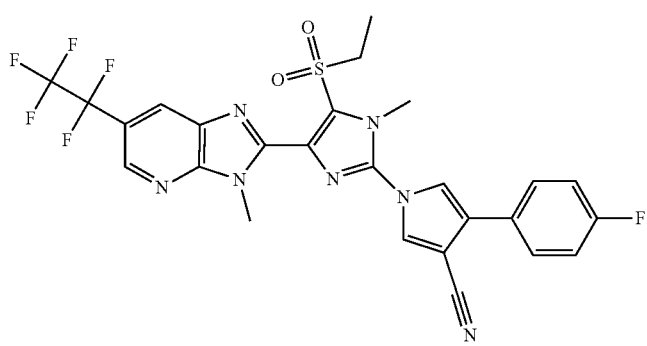 [SMILES: CCS(=O)(=O)c1c(-c2nc3cc(C(F)(F)C(F)(F)F)cnc3n2C)nc(-n2cc(C#N)c(-c3ccc(F)cc3)c2)n1C] |
| I-27 | 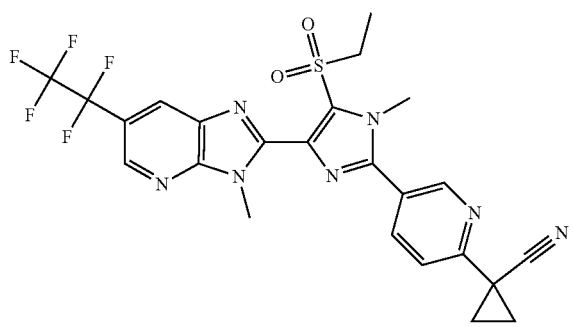 [SMILES: CCS(=O)(=O)c1c(-c2nc3cc(C(F)(F)C(F)(F)F)cnc3n2C)nc(-c2ccc(C3(C#N)CC3)nc2)n1C] |

The log P values were determined according to EEC Directive 79/831 Annex V.A8 by HPLC (high-performance liquid chromatography) on a reversed-phase column ($C_{18}$) using the following methods:

[a] The log P value is determined by LC-UV measurement in the acidic range using 0.9 ml/l formic acid in water and 1.0 ml/l formic acid in acetonitrile as mobile phases (linear gradient from 10% acetonitrile to 95% acetonitrile).

[b] The log P value is determined by LC-UV measurement in the neutral range using 79 mg/l ammonium carbonate in water and acetonitrile as mobile phases (linear gradient from 10% acetonitrile to 95% acetonitrile).

Calibration was carried out using a homologous series of straight-chain alkan-2-ones (having 3 to 16 carbon atoms) with known log P values. The values between successive alkanones are determined by linear regression.

The determination of $[M+H]^+$ or $M^-$ by LC-MS under acidic chromatographic conditions was carried out using 1 ml of formic acid per litre of acetonitrile and 0.9 ml of formic acid per litre of Millipore water as mobile phases. The Zorbax Eclipse Plus $C_{18\ 50}$ mm*2.1 mm, 1.8 µm column was used at a column oven temperature of 55° C.

Instruments:

LC-MS3: Waters UPLC with SQD2 mass spectrometer and SampleManager sample changer. Linear gradient from 0.0 to 1.70 minutes from 10% acetonitrile to 95% acetonitrile, from 1.70 to 2.40 minutes constant 95% acetonitrile, flow rate 0.85 ml/min.

LC-MS6 and LC-MS7: Agilent 1290 LC, Agilent MSD mass spectrometer, HTS PAL sample changer. Linear gradient from 0.0 to 1.80 minutes from 10% acetonitrile to 95% acetonitrile, from 1.80 to 2.50 minutes constant 95% acetonitrile, flow rate 1.0 ml/min.

The determination of $[M+H]^+$ by LC-MS under neutral chromatographic conditions was carried out using acetonitrile and Millipore water with 79 mg/l ammonium carbonate as mobile phases.

Instruments:

LC-MS4: Waters IClass Acquity with QDA mass spectrometer and FTN sample changer (column Waters Acquity 1.7 µm 50 mm*2.1 mm, column oven temperature 45° C.). Linear gradient from 0.0 to 2.10 minutes from 10% acetonitrile to 95% acetonitrile, from 2.10 to 3.00 minutes constant 95% acetonitrile, flow rate 0.7 ml/min.

LC-MS5: Agilent 1100 LC system with MSD mass spectrometer and HTS PAL sample changer (column: Zorbax XDB C18 1.8 µm 50 mm*4.6 mm, column oven temperature 55° C.). Linear gradient from 0.0 to 4.25 minutes from 10% acetonitrile to 95% acetonitrile, from 4.25 to 5.80 minutes constant 95% acetonitrile, flow rate 2.0 ml/min.

In all cases, the retention time indices were determined from a calibration measurement of a homologous series of straight-chain alkan-2-ones having 3 to 16 carbons, where the index of the first alkanone was set to 300, the index of the last alkanone was set to 1600 and linear interpolation was carried out between the values of successive alkanones.

The $^1H$ NMR spectra were measured with a Bruker Avance III 400 MHz spectrometer fitted with a 1.7 mm TCI sample head using tetramethylsilane as standard (0.00 ppm), of solutions in the solvents $CD_3CN$, $CDCl_3$ or $d_6$-DMSO. Alternatively, a Bruker Avance III 600 MHz spectrometer fitted with a 5 mm CPNMP sample head or a Bruker Avance NEO 600 MHz spectrometer fitted with a 5 mm TCI sample head was employed for the measurements. In general, the measurements were carried out at a sample head temperature of 298 K. If other measurement temperatures were used, this is specifically mentioned.

The NMR data of selected examples are listed either in conventional form (6 values, multiplet splitting, number of hydrogen atoms) or as NMR peak lists.

In each case, the solvent in which the NMR spectrum was recorded is stated.

NMR Data of Selected Examples

NMR Peak List Method

The $^1H$ NMR data of selected examples are stated in the form of $^1H$ NMR peak lists. For each signal peak, first the δ value in ppm and then the signal intensity in round brackets is listed. The δ value signal intensity number pairs for different signal peaks are listed with separation from one another by semicolons.

The peak list for one example therefore has the form:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed representation of a $^1H$ NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1H$ NMR spectra is accomplished using tetramethylsilane or the chemical shift of the solvent if the sample does not contain any tetramethylsilane. Accordingly, in certain cases the $^1H$ NMR peak lists may comprise the tetramethylsilane peak.

The $^1H$ NMR peak lists are equivalent to conventional $^1H$ NMR representations and thus usually contain all peaks listed in a conventional $^1H$ NMR interpretation.

In addition, like conventional $^1H$ NMR representations, they may show solvent signals, signals of stereoisomers of the compounds according to the invention which are optionally provided by the invention, and/or peaks of impurities.

NMR solvent signals, the tetramethylsilane peak and the water signal in the solvent in question are excluded from the calibration of the relative intensity since their stated intensity values can be very high.

The peaks of (stereo)isomers of the compounds of the invention and/or peaks of impurities usually have a lower intensity on average than the peaks of the compounds of the invention (for example at a purity of >90%).

Such stereoisomers and/or impurities may be typical of the particular preparation process. Their peaks can thus help in this case to identify reproduction of a preparation process with reference to "by-product fingerprints".

An expert calculating the peaks of the compounds according to the invention by known methods (MestreC, ACD simulation, but also with empirically evaluated expected values) can, if required, identify the peaks of the compounds of the invention, optionally using additional intensity filters. This identification is equivalent to the relevant peak listing in conventional 1H NMR interpretation.

In the JCAMP database, the solvent employed, the measuring frequency of the spectrometer and the spectrometer model can be found using the parameter "solvent", "observe frequency" and "spectrometer/data system", respectively.

$^{13}C$ NMR data are stated analogously to the $^1H$ NMR data as peak lists using broadband-decoupled $^{13}C$ NMR spectra. Here, too, NMR solvent signals and tetramethylsilane are excluded from the calibration of the relative intensity since these signals may have very high intensity values.

Further details on $^1H$ NMR peak lists can be found in: "Citation of NMR Peaklist Data within Patent Applications" in Research Disclosure Database Number 564025.

I-2: $^1$H-NMR(400.2 MHz, d$_6$-DMSO):
δ = 8.8203 (2.6); 8.8171 (2.7); 8.5802 (2.7); 8.5763 (2.7); 7.7928 (4.0); 7.7714 (5.0); 7.5621 (5.0); 7.5406 (4.2); 6.2402 (1.1); 6.2234 (1.3); 6.2128 (1.3); 6.1959 (1.2); 4.2762 (1.0); 4.2594 (1.0); 4.2332 (1.2); 4.2166 (1.2); 4.0561 (14.1); 4.0381 (1.1); 4.0202 (0.9); 4.0023 (0.3); 3.9433 (1.1); 3.9158 (1.4); 3.9005 (1.0); 3.8732 (0.9); 3.8042 (16.0); 3.7792 (2.2); 3.7749 (2.2); 3.7573 (0.8); 3.3194 (114.5); 2.6749 (1.1); 2.6707 (1.4); 2.6663 (1.1); 2.5060 (178.0); 2.5017 (229.6); 2.4973 (181.7); 2.3329 (1.2); 2.3286 (1.6); 2.3243 (1.3); 1.9886 (3.5); 1.2979 (3.7); 1.2795 (7.9); 1.2611 (3.7); 1.2364 (0.4); 1.1929 (1.0); 1.1751 (1.9); 1.1574 (1.1); 1.0687 (0.4); −0.0002 (3.5)

I-3: $^1$H-NMR(400.2 MHz, d$_6$-DMSO):
δ = 8.8170 (1.9); 8.8135 (1.9); 8.6853 (1.0); 8.6826 (1.2); 8.6787 (1.0); 8.6731 (1.0); 8.6706 (1.3); 8.6691 (1.2); 8.6665 (1.0); 8.5768 (2.0); 8.5724 (2.0); 7.9712 (0.6); 7.9684 (1.0); 7.9656 (0.7); 7.9513 (1.4); 7.9486 (2.2); 7.9458 (1.3); 7.9238 (1.1); 7.9195 (1.1); 7.9053 (1.4); 7.9009 (1.3); 7.8855 (0.7); 7.8812 (0.6); 7.5108 (0.9); 7.5074 (1.0); 7.4986 (0.9); 7.4952 (1.0); 7.4925 (1.0); 7.4891 (0.9); 7.4802 (0.8); 7.4768 (0.8); 6.2751 (1.0); 6.2584 (1.2); 6.2474 (1.2); 6.2305 (1.0); 4.3573 (0.9); 4.3404 (0.9); 4.3132 (1.1); 4.2965 (1.0); 4.0693 (13.1); 3.9632 (1.0); 3.9352 (1.2); 3.9191 (1.0); 3.8913 (0.8); 3.8142 (0.8); 3.7995 (16.0); 3.7777 (2.3); 3.7592 (0.8); 3.3224 (42.3); 2.6764 (0.4); 2.6718 (0.5); 2.6672 (0.4); 2.5252 (1.8); 2.5204 (2.9); 2.5119 (29.9); 2.5074 (58.5); 2.5028 (76.4); 2.4982 (56.1); 2.4937 (27.5); 2.3343 (0.3); 2.3296 (0.5); 2.3252 (0.3); 2.0749 (5.9); 1.3006 (3.2); 1.2821 (7.4); 1.2637 (3.1); −0.0002 (0.7)

I-4: $^1$H-NMR(400.2 MHz, d$_6$-DMSO):
δ = 8.9502 (2.2); 8.9462 (2.2); 8.8204 (2.1); 8.8170 (2.1); 8.6820 (1.6); 8.6780 (1.7); 8.6700 (1.7); 8.6660 (1.7); 8.5820 (2.2); 8.5775 (2.2); 8.1740 (0.9); 8.1693 (1.3); 8.1643 (0.9); 8.1540 (1.1); 8.1492 (1.4); 8.1443 (0.9); 7.5326 (1.1); 7.5222 (1.1); 7.5206 (1.1); 7.5141 (1.1); 7.5022 (1.0); 7.5006 (1.0); 6.2717 (1.0); 6.2548 (1.2); 6.2442 (1.2); 6.2271 (1.1); 4.3316 (0.9); 4.3145 (0.9); 4.2885 (1.1); 4.2716 (1.1); 4.0662 (13.7); 3.9928 (1.0); 3.9650 (1.2); 3.9497 (1.0); 3.9222 (0.8); 3.8227 (1.0); 3.8106 (16.0); 3.7999 (2.0); 3.7861 (1.8); 3.7815 (1.8); 3.7636 (0.3); 3.3212 (74.0); 2.6756 (0.8); 2.6710 (1.0); 2.6666 (0.8); 2.6621 (0.4); 2.5244 (3.6); 2.5196 (5.8); 2.5111 (62.3); 2.5066 (121.6); 2.5020 (158.7); 2.4975 (116.5); 2.4930 (58.1); 2.3380 (0.4); 2.3334 (0.8); 2.3289 (1.0); 2.3244 (0.8); 1.3020 (3.4); 1.2836 (7.7); 1.2651 (3.3); 0.0079 (2.8); −0.0002 (73.2); −0.0085 (2.7)

I-6: $^1$H-NMR(400.2 MHz, d$_6$-DMSO):
δ = 8.8406 (2.0); 8.8371 (2.0); 8.6042 (2.1); 8.6001 (2.0); 8.4768 (4.2); 8.3153 (0.6); 8.0015 (4.2); 8.0002 (4.2); 4.0224 (14.0); 3.8960 (0.4); 3.8865 (0.8); 3.8732 (16.0); 3.8590 (1.1); 3.8499 (0.7); 3.8403 (0.4); 3.7681 (0.9); 3.7495 (3.1); 3.7311 (3.1); 3.7126 (0.9); 3.3217 (77.4); 2.6795 (0.6); 2.6750 (1.3); 2.6705 (1.8); 2.6659 (1.3); 2.6612 (0.6); 2.5645 (1.0); 2.5239 (5.8); 2.5192 (8.5); 2.5105 (106.4); 2.5061 (213.9); 2.5015 (278.8); 2.4969 (198.4); 2.4924 (94.1); 2.3375 (0.6); 2.3329 (1.3); 2.3283 (1.7); 2.3238 (1.2); 2.3194 (0.6); 1.9885 (0.4); 1.3040 (3.4); 1.2856 (7.8); 1.2671 (3.2); 1.1695 (0.5); 1.1568 (1.3); 1.1545 (1.3); 1.1481 (2.2); 1.1401 (2.2); 1.1299 (0.8); 1.0995 (0.4); 1.0605 (0.8); 1.0483 (1.6); 1.0424 (1.9); 1.0297 (1.9); 1.0260 (1.3); 1.0238 (1.3); 1.0100 (0.5); 0.1459 (0.8); 0.0080 (6.5); −0.0002 (204.2); −0.0085 (6.5); −0.1497 (0.8)

I-7: $^1$H-NMR(400.2 MHz, d$_6$-DMSO):
δ = 10.2045 (0.6); 8.8555 (2.8); 8.6313 (2.8); 8.6271 (2.8); 7.6490 (3.3); 7.6443 (3.5); 6.8814 (3.4); 6.8767 (3.5); 5.7569 (6.6); 4.0179 (0.4); 4.0083 (0.7); 3.9993 (1.1); 3.9902 (1.5); 3.9808 (1.1); 3.9719 (0.9); 3.9629 (0.7); 3.9433 (14.6); 3.9293 (16.0); 3.8999 (1.3); 3.8820 (3.5); 3.8635 (3.6); 3.8450 (1.2); 3.3269 (144.2); 2.6710 (1.0); 2.5056 (119.2); 2.5021 (152.4); 2.3290 (1.0); 1.3569 (3.7); 1.3385 (7.9); 1.3201 (3.6); 1.0769 (0.6); 1.0638 (1.9); 1.0562 (3.0); 1.0478 (2.8); 1.0373 (0.9); 0.9571 (0.9); 0.9456 (2.0); 0.9393 (2.6); 0.9272 (2.4); 0.9223 (2.0); 0.9082 (0.6); 0.1458 (0.4); −0.0003 (72.6); −0.1501 (0.4)

I-8: $^1$H-NMR(400.2 MHz, d$_6$-DMSO):
δ = 8.8442 (3.2); 8.6094 (3.2); 7.5732 (3.1); 7.5637 (3.2); 7.0012 (3.0); 6.9917 (3.0); 4.0812 (14.8); 3.8691 (16.0); 3.7818 (1.2); 3.7636 (3.6); 3.7451 (3.7); 3.7270 (1.2); 3.3270 (128.5); 2.6717 (1.0); 2.5061 (134.1); 2.5024 (172.5); 2.4987 (143.8); 2.3289 (1.0); 2.2680 (0.4); 2.2559 (0.7); 2.2470 (0.8); 2.2351 (1.4); 2.2229 (0.9); 2.2145 (0.8); 2.2018 (0.4); 1.3110 (3.9); 1.2926 (8.2); 1.2742 (3.8); 1.1122 (0.9); 1.1013 (2.4); 1.0957 (2.9); 1.0806 (2.6); 1.0752 (2.8); 1.0649 (1.0); 0.7952 (1.0); 0.7842 (3.1); 0.7798 (3.2); 0.7728 (2.9); 0.7677 (3.4); 0.7564 (0.9); 0.1461 (0.4); −0.0004 (72.8); −0.1497 (0.4)

I-10: $^1$H-NMR(400.2 MHz, d$_6$-DMSO):
δ = 8.8584 (2.4); 8.8539 (2.4); 8.6343 (2.5); 8.6298 (2.4); 8.5855 (6.3); 8.3149 (0.4); 5.7553 (0.8); 3.9505 (14.7); 3.8928 (16.0); 3.8522 (1.0); 3.8337 (3.3); 3.8152 (3.4); 3.7968 (1.0); 3.3225 (137.3); 2.6749 (0.8); 2.6703 (1.1); 2.6661 (0.8); 2.5235 (3.0); 2.5098 (65.9); 2.5059 (129.2); 2.5015 (169.0); 2.4971 (124.0); 2.3327 (0.8); 2.3283 (1.0); 2.3240 (0.8); 2.0036 (0.6); 1.9952 (0.7); 1.9830 (1.3); 1.9706 (0.8); 1.9623 (0.7); 1.9497 (0.3); 1.3335 (3.7); 1.3151 (8.1); 1.2966 (3.6); 1.0651 (0.6); 1.0543 (1.7); 1.0479 (2.2); 1.0388 (1.2); 1.0336 (1.6); 1.0272 (2.0); 1.0186 (0.8); 0.9420 (0.9); 0.9331 (2.2); 0.9274 (2.2); 0.9211 (2.3); 0.9151 (2.1); 0.9037 (0.6); 0.1455 (0.3); 0.0072 (2.7); −0.0003 (70.7); −0.0008 (70.7); −0.0083 (3.1); −0.1498 (0.4)

I-11: $^1$H-NMR(400.2 MHz, d$_6$-DMSO):
δ = 8.8579 (1.1); 8.8546 (1.1); 8.6268 (1.2); 8.6230 (1.1); 7.8131 (1.2); 7.8032 (1.5); 7.7826 (1.4); 7.7640 (1.6); 7.7198 (1.4); 7.7099 (1.2); 7.4935 (0.7); 7.4752 (1.6); 7.4556 (1.0); 7.4074 (0.6); 7.3889 (0.8); 4.1619 (5.3); 4.0570 (1.3); 4.0392 (4.0); 4.0214 (4.0); 4.0036 (1.4); 3.9048 (6.9); 3.8111 (0.4); 3.7927 (1.5); 3.7743 (1.5); 3.7559 (0.5); 3.5871 (0.5); 3.5813 (0.3); 3.5693 (0.5); 3.3275 (12.5); 2.5083 (10.6); 2.5039 (13.7); 2.4996 (10.3); 1.9901 (16.0); 1.3363 (1.7); 1.3179 (3.6); 1.2995 (1.6); 1.1938 (4.4); 1.1760 (8.7); 1.1582 (4.3); 0.0078 (0.4); −0.0002 (8.9); −0.0083 (0.4)

I-12: $^1$H-NMR(400.2 MHz, d$_6$-DMSO):
δ = 8.8514 (2.3); 8.8469 (2.3); 8.6230 (2.4); 8.6189 (2.3); 8.3153 (1.2); 7.7710 (1.3); 7.7523 (1.7); 7.7215 (2.6); 7.6507 (1.0); 7.6314 (2.3); 7.6126 (1.6); 7.5936 (2.0); 7.5736 (0.8); 3.9639 (0.8); 3.9506 (13.8); 3.9029 (16.0); 3.8468 (1.0); 3.8284 (3.2); 3.8099 (3.2); 3.7915 (1.0); 3.3261 (799.2); 2.6753 (2.9); 2.6707 (4.0); 2.6662 (2.9); 2.6003 (0.4); 2.5241 (11.2); 2.5106 (243.5); 2.5063 (492.3); 2.5019 (647.4); 2.4974 (463.6); 2.4930 (223.2); 2.3330 (2.7); 2.3287 (3.9); 2.3241 (2.8); 1.8444 (1.1); 1.8312 (3.2); 1.8242 (3.5); 1.8127 (1.4); 1.6466 (1.5); 1.6345 (3.3); 1.6274 (3.5); 1.6139 (1.1); 1.3519 (3.5); 1.3336 (7.8); 1.3151 (3.4); 1.2332 (0.4); 0.1463 (0.4); 0.0079 (3.2); −0.0002 (95.6); −0.0084 (3.4); −0.1496 (0.4)

I-13: $^1$H-NMR(400.2 MHz, d$_6$-DMSO):
δ = 8.8577 (2.1); 8.8542 (2.2); 8.6263 (2.2); 8.6222 (2.2); 7.7558 (3.3); 7.7459 (3.5); 7.6292 (1.9); 7.6264 (2.0); 7.6165 (2.0); 7.6137 (2.0); 7.4902 (4.9); 7.4802 (5.1); 7.1616 (2.1); 7.1525 (2.0); 7.1398 (2.0); 5.7558 (2.2); 4.1468 (14.4); 3.8949 (16.0); 3.8019 (0.9); 3.7834 (3.2); 3.7649 (3.2); 3.7465 (1.0); 3.3240 (148.1); 2.6755 (0.6); 2.6709 (0.8); 2.6665 (0.7); 2.5245 (2.7); 2.5197 (4.0); 2.5110 (51.5); 2.5066 (105.2); 2.5020 (139.6); 2.4974 (101.8); 2.4929 (49.7); 2.3334 (0.7); 2.3288 (0.9); 2.3243 (0.6); 1.3293 (3.5); 1.3109 (8.1); 1.2925 (3.5); −0.0002 (4.8)

I-14: $^1$H-NMR(400.2 MHz, d$_6$-DMSO):
δ = 8.8489 (0.7); 8.8453 (0.7); 8.8184 (0.7); 8.8131 (0.7); 8.6188 (0.7); 8.6147 (0.7); 8.1020 (0.5); 8.0962 (0.5); 8.0816 (0.5); 8.0759 (0.5); 7.5414 (0.7); 7.5209 (0.6); 3.9687 (4.4); 3.9298 (2.4); 3.9097 (4.9); 3.8381 (1.0); 3.8196 (1.0); 3.5858 (0.4); 3.5800 (0.3); 3.3257 (24.3); 2.5245 (0.7); 2.5112 (10.7); 2.5070 (20.8); 2.5025 (26.9); 2.4979 (19.6); 2.4936 (9.7); 2.2354 (0.4); 1.3493 (1.1); 1.3309 (2.4); 1.3124 (1.1); 1.2343 (0.6); 1.0914 (0.4); 1.0691 (16.0); 1.0485 (0.4); 1.0415 (1.1); 1.0359 (1.1); 1.0280 (0.8); 1.0232 (0.9); 1.0165 (0.7); 0.0078 (0.7); −0.0002 (16.2); −0.0084 (0.6)

I-15: $^1$H-NMR(400.2 MHz, d$_6$-DMSO):
δ = 8.7799 (2.3); 8.7751 (2.4); 8.5716 (2.4); 8.5669 (2.3); 7.8567 (3.8); 7.8520 (1.4); 7.8402 (1.4); 7.8354 (4.6); 7.8303 (0.7); 7.5568 (4.4); 7.5520 (1.4); 7.5401 (1.3); 7.5354 (3.9); 5.7563 (1.8); 3.9669 (14.3); 3.9281 (0.6); 3.9190 (16.0); 3.8655 (0.9); 3.8471 (3.1); 3.8286 (3.2); 3.8101 (0.9); 3.3263 (47.6); 2.5255 (0.9); 2.5208 (1.3); 2.5121 (17.1); 2.5077 (35.1); 2.5031 (46.5);

2.4985 (33.6); 2.4939 (16.2); 1.8795 (1.1); 1.8666 (3.0); 1.8594 (3.4); 1.8481 (1.4); 1.6604 (1.3); 1.6479 (3.2); 1.6408 (3.3); 1.6271 (1.0); 1.3529 (3.5); 1.3345 (8.1); 1.3160 (3.4); −0.0002 (1.8)

I-16: $^1$H-NMR(400.2 MHz, $d_6$-DMSO):
δ = 8.7728 (2.1); 8.7680 (2.2); 8.5585 (2.2); 8.5538 (2.2); 8.4753 (4.3); 8.3150 (0.4); 7.9996 (4.3); 7.9983 (4.3); 4.0230 (14.2); 3.8976 (0.5); 3.8857 (16.0); 3.8701 (1.5); 3.8606 (1.1); 3.8516 (0.7); 3.8419 (0.4); 3.7788 (0.9); 3.7604 (3.0); 3.7419 (3.1); 3.7235 (0.9); 3.3238 (229.8); 2.6797 (0.4); 2.6753 (1.0); 2.6707 (1.4); 2.6661 (1.0); 2.6618 (0.4); 2.5242 (3.7); 2.5194 (5.6); 2.5108 (78.3); 2.5063 (160.1); 2.5017 (212.3); 2.4972 (154.0); 2.4926 (74.8); 2.3377 (0.5); 2.3331 (1.0); 2.3286 (1.4); 2.3240 (1.0); 2.3195 (0.5); 1.3070 (3.5); 1.2886 (8.0); 1.2702 (3.4); 1.2345 (0.4); 1.1696 (0.7); 1.1591 (1.4); 1.1568 (1.4); 1.1548 (1.5); 1.1483 (2.5); 1.1403 (2.4); 1.1301 (1.0); 1.0999 (0.6); 1.0897 (0.4); 1.0821 (0.4); 1.0613 (1.0); 1.0491 (1.8); 1.0431 (2.1); 1.0304 (2.1); 1.0266 (1.6); 1.0247 (1.5); 1.0108 (0.6); −0.0003 (7.7)

I-17: $^1$H-NMR(400.2 MHz, $d_6$-DMSO):
δ = 9.1379 (4.9); 8.7903 (1.3); 8.7845 (2.3); 8.7799 (2.4); 8.5759 (2.4); 8.5713 (2.4); 8.3354 (5.2); 8.3153 (0.4); 8.0499 (1.2); 8.0353 (2.1); 8.0298 (0.8); 8.0234 (2.2); 8.0180 (1.3); 8.0124 (2.4); 8.0063 (0.8); 8.0006 (2.2); 7.8876 (0.5); 7.8758 (0.5); 7.8646 (0.5); 7.8529 (0.5); 7.4519 (2.3); 7.4463 (0.7); 7.4399 (0.4); 7.4298 (3.7); 7.4201 (0.3); 7.4134 (0.7); 7.4077 (2.7); 7.3852 (0.9); 7.3632 (0.5); 5.7557 (3.2); 4.1185 (14.4); 3.9196 (16.0); 3.8128 (0.9); 3.7943 (3.2); 3.7758 (3.3); 3.7574 (1.0); 3.3245 (187.5); 2.6756 (0.8); 2.6710 (1.1); 2.6666 (0.8); 2.6619 (0.4); 2.5245 (3.5); 2.5197 (5.2); 2.5110 (61.8); 2.5066 (124.0); 2.5021 (162.7); 2.4975 (117.2); 2.4930 (56.0); 2.3334 (0.7); 2.3289 (1.0); 2.3243 (0.7); 1.3321 (3.6); 1.3137 (8.2); 1.2953 (3.5); 1.2346 (1.2); 1.1587 (0.5); 1.0687 (0.6); −0.0002 (5.7)

I-18: $^1$H-NMR(400.2 MHz, $d_6$-DMSO):
δ = 9.0982 (4.9); 9.0969 (4.9); 8.7860 (2.2); 8.7813 (2.2); 8.5790 (2.3); 8.5742 (2.1); 8.4501 (4.9); 8.4489 (4.8); 8.3143 (0.6); 8.1622 (2.5); 8.1083 (1.5); 8.1069 (1.5); 8.0893 (1.6); 8.0868 (1.5); 7.9834 (0.4); 7.9798 (0.7); 7.9629 (2.3); 7.9590 (3.5); 7.9419 (1.5); 7.9384 (1.5); 7.9214 (0.5); 7.9178 (0.5); 7.7040 (1.1); 7.6992 (1.1); 7.6868 (1.0); 7.6845 (1.2); 7.6823 (1.2); 7.6802 (1.1); 7.6672 (0.8); 7.6628 (0.8); 5.7549 (3.2); 4.1168 (14.1); 3.9216 (16.0); 3.8213 (0.9); 3.8030 (3.1); 3.7845 (3.2); 3.7661 (1.0); 3.4734 (0.4); 3.4613 (0.4); 3.3312 (172.6); 2.6803 (0.6); 2.6758 (1.2); 2.6713 (1.6); 2.6667 (1.2); 2.6620 (0.6); 2.5416 (0.7); 2.5248 (4.5); 2.5200 (6.6); 2.5113 (91.3); 2.5068 (188.7); 2.5023 (249.9); 2.4977 (178.1); 2.4931 (83.7); 2.3382 (0.5); 2.3337 (1.1); 2.3291 (1.6); 2.3245 (1.1); 2.3201 (0.5); 1.3356 (3.4); 1.3172 (8.0); 1.2988 (3.6); 1.2350 (1.6); 0.8541 (0.4); −0.0003 (3.3)

I-19: $^1$H-NMR(400.2 MHz, $d_6$-DMSO):
δ = 9.2917 (4.7); 8.9826 (0.5); 8.7875 (2.2); 8.7825 (2.2); 8.5802 (2.3); 8.5755 (2.2); 8.5249 (1.5); 8.5209 (2.2); 8.4122 (5.3); 8.3592 (1.1); 8.3564 (1.0); 8.3537 (1.0); 8.3410 (1.0); 8.3385 (1.1); 8.3354 (1.0); 8.3150 (1.6); 8.1284 (0.5); 7.8837 (1.3); 7.8646 (2.0); 7.8103 (1.8); 7.7902 (2.7); 7.7702 (1.1); 7.5702 (0.3); 7.5520 (0.5); 7.5259 (0.4); 4.4990 (0.4); 4.4943 (0.4); 4.2174 (0.4); 4.2123 (0.4); 4.1370 (13.9); 3.9268 (16.0); 3.8228 (0.9); 3.8044 (3.1); 3.7859 (3.2); 3.7675 (0.9); 3.4193 (0.4); 3.4086 (0.4); 3.3251 (836.3); 2.6796 (1.5); 2.6752 (3.1); 2.6707 (4.3); 2.6663 (3.2); 2.6617 (1.5); 2.5840 (0.3); 2.5242 (11.8); 2.5193 (17.6); 2.5107 (254.7); 2.5063 (521.6); 2.5018 (688.6); 2.4972 (491.8); 2.4927 (234.0); 2.4219 (0.3); 2.3376 (1.4); 2.3330 (3.0); 2.3286 (4.3); 2.3240 (3.1); 2.3196 (1.4); 2.0740 (3.9); 1.3377 (3.5); 1.3193 (8.0); 1.3008 (3.7); 1.2964 (2.6); 1.0685 (0.3); 0.9195 (0.5); −0.0003 (2.0)

I-20: $^1$H-NMR(400.2 MHz, $d_6$-DMSO):
δ = 9.3120 (4.5); 9.1687 (2.3); 8.7879 (2.3); 8.7833 (2.4); 8.6507 (2.8); 8.6445 (2.9); 8.5810 (2.4); 8.5767 (2.4); 8.4516 (5.3); 8.4343 (0.8); 8.4286 (1.3); 8.4227 (0.7); 8.4091 (0.8); 8.4033 (1.3); 8.3973 (0.7); 8.3155 (0.8); 5.3934 (0.7); 5.3239 (0.4); 4.1315 (14.1); 3.9227 (16.0); 3.8209 (0.9); 3.8027 (3.1); 3.7843 (3.2); 3.7657 (1.0); 3.3239 (223.3); 2.6753 (1.8); 2.6709 (2.6); 2.6663 (1.9); 2.5242 (6.3); 2.5107 (153.7); 2.5063 (315.5); 2.5019 (419.0); 2.4974 (308.1); 2.4931 (153.9); 2.3376 (1.0); 2.3331 (1.9); 2.3287 (2.6); 2.3242 (2.0); 2.1781 (0.4); 2.0265 (0.4); 2.0079 (0.8); 1.9888 (1.0); 1.9739 (0.4); 1.9627 (0.3); 1.5512 (0.7); 1.4743 (0.4); 1.4589 (0.4); 1.3361 (3.8); 1.3178 (8.2); 1.2991 (4.8); 1.2586 (3.0); 1.2354 (10.7); 1.1927 (0.3); 1.1751 (0.3); 1.1558 (1.5); 1.1389 (1.4); 0.8700 (0.7); 0.8539 (2.0); 0.8360 (0.9); 0.1459 (0.5); 0.0080 (3.7); −0.0001 (125.6); −0.0083 (5.3); −0.1496 (0.6)

I-21: $^1$H-NMR(400.2 MHz, $d_6$-DMSO):
δ = 8.7874 (2.1); 8.7826 (2.2); 8.5834 (2.2); 8.5787 (2.1); 8.2562 (2.9); 8.2497 (3.0); 8.1426 (6.0); 6.4079 (3.4); 6.4013 (3.4); 5.7503 (1.8); 4.0268 (14.7); 3.8986 (16.0); 3.8335 (1.0); 3.8150 (3.2); 3.7965 (3.2); 3.7781 (1.1); 3.7198 (0.3); 3.7062 (0.3); 3.6719 (0.4); 3.3842 (230.4); 2.6794 (0.6); 2.6747 (0.8); 2.6703 (0.6); 2.5282 (2.2); 2.5233 (3.6); 2.5148 (47.3); 2.5103 (96.3); 2.5058 (126.1); 2.5012 (89.6); 2.4967 (42.4); 2.3372 (0.6); 2.3325 (0.8); 2.3281 (0.6); 2.0728 (0.5); 2.0652 (0.6); 2.0571 (0.7); 2.0446 (1.3); 2.0323 (0.7); 2.0237 (0.7); 2.0112 (0.3); 1.3341 (3.5); 1.3157 (8.0); 1.2972 (3.4); 1.0206 (0.8); 1.0100 (2.1); 1.0039 (2.4); 0.9998 (1.0); 0.9944 (1.2); 0.9890 (2.1); 0.9829 (2.2); 0.9735 (0.9); 0.8249 (1.0); 0.8153 (2.4); 0.8124 (1.7); 0.8093 (2.4); 0.8030 (2.4); 0.7970 (2.4); 0.7863 (0.7); 0.1460 (0.6); 0.0186 (0.3); 0.0079 (5.2); −0.0002 (147.4); −0.0085 (5.0); −0.1495 (0.6)

I-22: $^1$H-NMR(400.2 MHz, $d_6$-DMSO):
δ = 8.8169 (2.1); 8.8112 (2.2); 8.7805 (2.2); 8.7758 (2.4); 8.5723 (2.3); 8.5675 (2.3); 8.3150 (0.5); 8.1007 (1.6); 8.0949 (1.6); 8.0803 (1.8); 8.0746 (1.8); 7.5422 (2.0); 7.5217 (2.0); 3.9684 (14.8); 3.9204 (16.0); 3.8651 (0.9); 3.8467 (3.1); 3.8282 (3.2); 3.8098 (0.9); 3.3241 (274.4); 2.6752 (1.1); 2.6708 (1.5); 2.6662 (1.1); 2.5243 (3.7); 2.5195 (5.8); 2.5108 (87.3); 2.5064 (180.1); 2.5018 (239.4); 2.4972 (173.2); 2.4927 (83.6); 2.3379 (0.6); 2.3332 (1.2); 2.3286 (1.6); 2.3241 (1.2); 2.2679 (0.4); 2.2552 (0.6); 2.2482 (0.7); 2.2357 (1.2); 2.2292 (0.6); 2.2233 (0.7); 2.2161 (0.7); 2.2036 (0.4); 1.3514 (3.6); 1.3330 (8.2); 1.3145 (3.5); 1.2342 (0.4); 1.0822 (0.4); 1.0689 (1.3); 1.0622 (2.8); 1.0567 (1.4); 1.0486 (1.2); 1.0417 (3.3); 1.0354 (3.1); 1.0276 (2.5); 1.0229 (2.9); 1.0161 (1.4); 1.0025 (0.3); −0.0002 (8.7)

I-23: $^1$H-NMR(400.2 MHz, $d_6$-DMSO):
δ = 8.7834 (2.2); 8.7788 (2.3); 8.5753 (2.3); 8.5707 (2.2); 7.7958 (1.3); 7.7771 (1.7); 7.7744 (1.7); 7.7557 (1.6); 7.4727 (2.6); 7.4546 (2.3); 7.3084 (0.6); 7.0474 (2.0); 7.0259 (1.9); 4.3321 (13.9); 4.0382 (0.7); 4.0204 (0.7); 3.8992 (16.0); 3.8199 (0.9); 3.8014 (3.2); 3.7829 (3.3); 3.7659 (3.4); 3.7554 (4.2); 3.7424 (3.4); 3.5549 (3.4); 3.5423 (4.1); 3.5307 (2.6); 3.3264 (109.7); 2.6760 (0.4); 2.6715 (0.6); 2.6669 (0.5); 2.5249 (1.8); 2.5201 (2.8); 2.5115 (36.8); 2.5071 (75.5); 2.5025 (99.7); 2.4980 (71.3); 2.4935 (34.0); 2.3338 (0.4); 2.3293 (0.6); 2.3248 (0.4); 1.9892 (3.3); 1.3351 (0.3); 1.3245 (3.5); 1.3062 (8.1); 1.2877 (3.5); 1.2492 (0.6); 1.2347 (1.3); 1.1930 (0.9); 1.1752 (1.8); 1.1574 (0.9); 0.9639 (0.4); 0.9457 (0.7); 0.9279 (0.4); 0.8537 (0.4); 0.0080 (0.5); −0.0002 (15.4); −0.0084 (0.5)

I-24: $^1$H-NMR(400.2 MHz, $d_6$-DMSO):
δ = 8.7825 (2.4); 8.7780 (2.5); 8.5753 (2.5); 8.5709 (2.4); 7.9525 (0.6); 7.7708 (1.4); 7.7521 (1.8); 7.7488 (1.3); 7.7276 (1.8); 7.7234 (2.7); 7.6520 (1.0); 7.6324 (2.3); 7.6137 (1.6); 7.5968 (1.3); 7.5933 (1.9); 7.5892 (1.3); 7.5771 (0.7); 7.5728 (0.8); 4.0380 (0.5); 4.0203 (0.5); 3.9650 (0.6); 3.9522 (14.0); 3.9155 (16.0); 3.8573 (0.9); 3.8388 (3.1); 3.8203 (3.2); 3.8017 (1.0); 3.3287 (184.3); 2.8912 (4.3); 2.7316 (3.6); 2.6759 (0.5); 2.6715 (0.7); 2.6671 (0.5); 2.5247 (2.1); 2.5113 (43.2); 2.5070 (87.2); 2.5025 (114.6); 2.4980 (82.5); 2.4937 (40.0); 2.3339 (0.5); 2.3294 (0.7); 2.3248 (0.5); 1.9891 (2.0); 1.8456 (1.1); 1.8327 (3.3); 1.8255 (3.5); 1.8140 (1.4); 1.6466 (1.5); 1.6344 (3.4); 1.6273 (3.5); 1.6138 (1.0); 1.3560 (3.5); 1.3376 (8.0); 1.3191 (3.4); 1.1929 (0.6); 1.1752 (1.1); 1.1574 (0.6); 0.0079 (0.6); −0.0002 (15.8); −0.0084 (0.6)

I-25: ¹H-NMR(400.2 MHz, d₆-DMSO):
δ = 8.8011 (2.4); 8.7963 (2.5); 8.6018 (2.5); 8.5976 (2.4); 8.3999 (3.5); 8.3943 (3.4); 8.3849 (0.3); 8.3156 (2.0); 8.0215 (0.4); 8.0152 (0.4); 7.8477 (1.9); 7.8427 (2.6); 7.8383 (1.8); 7.7337 (0.8); 7.7294 (0.9); 7.7147 (1.5); 7.7103 (1.5); 7.6953 (0.7); 7.6909 (0.9); 7.5805 (0.4); 7.5695 (0.4); 7.5646 (0.4); 7.5054 (0.4); 7.5003 (0.4); 7.4920 (0.6); 7.4873 (0.8); 7.4663 (1.1); 7.4613 (0.8); 7.4528 (0.7); 7.4485 (0.8); 7.4149 (1.2); 7.3880 (1.3); 7.3797 (1.4); 7.3670 (0.8); 7.3611 (1.8); 7.3424 (0.8); 7.3398 (0.8); 3.9450 (16.0); 3.9174 (1.0); 3.8987 (3.5); 3.8801 (3.6); 3.8703 (13.9); 3.4391 (0.4); 3.4324 (0.3); 3.4177 (0.4); 3.3240 (1010.3); 3.2813 (0.4); 2.6797 (2.6); 2.6753 (5.4); 2.6707 (7.2); 2.6662 (5.3); 2.6404 (0.4); 2.6196 (0.5); 2.5241 (21.1); 2.5193 (33.6); 2.5107 (424.6); 2.5063 (869.0); 2.5017 (1146.8); 2.4972 (822.2); 2.4927 (393.8); 2.4009 (0.3); 2.3374 (2.3); 2.3331 (4.9); 2.3286 (7.1); 2.3240 (5.2); 2.3196 (2.5); 1.3890 (3.7); 1.3704 (8.4); 1.3519 (3.6); 1.2352 (1.2); 0.1461 (0.8); 0.0079 (6.8); −0.0002 (219.7); −0.0085 (8.1); −0.0263 (0.5); −0.1500 (0.9)

I-26: ¹H-NMR(400.2 MHz, d₆-DMSO):
δ = 8.8012 (2.3); 8.7967 (2.5); 8.6023 (2.4); 8.5979 (2.4); 8.3626 (3.3); 8.3568 (3.4); 7.9134 (3.2); 7.9077 (3.1); 7.7655 (2.0); 7.7603 (0.9); 7.7521 (2.2); 7.7434 (2.6); 7.7355 (1.0); 7.7300 (2.3); 7.3811 (2.2); 7.3759 (0.8); 7.3589 (4.2); 7.3419 (0.7); 7.3367 (2.0); 5.7560 (2.8); 3.9473 (16.0); 3.9237 (1.0); 3.9052 (3.3); 3.8900 (15.1); 3.8683 (1.0); 3.3246 (74.2); 2.6759 (0.5); 2.6713 (0.7); 2.6669 (0.5); 2.5248 (2.1); 2.5112 (44.0); 2.5069 (89.7); 2.5024 (117.9); 2.4979 (85.2); 2.4935 (41.7); 2.3336 (0.5); 2.3292 (0.7); 2.3246 (0.6); 2.0748 (0.3); 1.3877 (3.4); 1.3693 (7.8); 1.3508 (3.4); 0.1459 (0.4); 0.0079 (3.4); −0.0002 (98.0); −0.0085 (3.8); −0.1496 (0.4)

I-27: ¹H-NMR(400.2 MHz, d₆-DMSO):
δ = 8.9423 (2.1); 8.9403 (2.3); 8.9367 (2.3); 8.9347 (2.1); 8.7844 (2.1); 8.7798 (2.2); 8.5783 (2.2); 8.5735 (2.2); 8.3157 (2.4); 8.3110 (1.7); 8.3053 (1.5); 8.2903 (1.8); 8.2846 (1.9); 7.7767 (2.2); 7.7748 (2.1); 7.7561 (2.1); 7.7541 (2.0); 3.9811 (14.0); 3.9224 (16.0); 3.8754 (0.9); 3.8572 (3.0); 3.8388 (3.1); 3.8205 (0.9); 3.3248 (703.0); 2.6798 (1.6); 2.6754 (3.6); 2.6708 (5.0); 2.6662 (3.6); 2.6617 (1.7); 2.5244 (14.0); 2.5196 (20.8); 2.5109 (289.1); 2.5064 (597.2); 2.5018 (790.9); 2.4972 (565.6); 2.4927 (267.4); 2.3378 (1.6); 2.3332 (3.6); 2.3287 (4.9); 2.3241 (3.6); 2.3195 (1.6); 1.9437 (1.0); 1.9312 (2.4); 1.9225 (3.3); 1.9134 (1.4); 1.8277 (1.5); 1.8179 (3.2); 1.8093 (2.4); 1.7962 (0.9); 1.3585 (3.3); 1.3400 (7.8); 1.3216 (3.2); 0.1460 (4.1); 0.0322 (0.5); 0.0228 (0.8); 0.0080 (34.8); −0.0002 (1044.9); −0.0085 (33.9); −0.0172 (1.7); −0.0253 (0.9); −0.0354 (0.5); −0.1495 (4.2)

Use Examples

*Boophilus microplus*—Injection Test

| Solvent: | dimethyl sulfoxide |

To produce a suitable active compound preparation, 10 mg of active compound are mixed with 0.5 ml of solvent and the concentrate is diluted to the desired concentration with solvent.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 95% at an application rate of 20 µg/animal: I-6.

In this test, for example, the following compounds from the preparation examples show an efficacy of 90% at an application rate of 20 µg/animal: I-10.

*Ctenocephalides felis*—Oral Test

| Solvent: | dimethyl sulfoxide |

To produce a suitable active compound preparation, 10 mg of active compound are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-1, I-5, I-6.

In this test, for example, the following compounds from the preparation examples show an efficacy of 90% at an application rate of 100 ppm: I-9, I-10, I-11, I-14.

In this test, for example, the following compounds from the preparation examples show an efficacy of 80% at an application rate of 100 ppm: I-8.

*Diabrotica balteata*—Spray Test

| Solvent: | 78 parts by weight of acetone |
| | 1.5 parts by weight of dimethylformamide |
| Emulsifier: | alkylaryl polyglycol ether |

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Pre-swollen wheat grains (*Triticum aestivum*) are incubated in a multiwell plate filled with agar and a little water for one day (5 seed grains per well). The germinated wheat grains are sprayed with an active compound preparation of the desired concentration. Subsequently, each cavity is infected with 10-20 beetle larvae of *Diabrotica balteata*.

After 7 days, the efficacy in % is determined. 100% means that all wheat plants have grown as in the untreated, uninfected control; 0% means that no wheat plant has grown.

In this test, for example, the following compounds from the preparation examples show an efficacy of 100% at an application rate of 160 µg/well: I-12, I-15, I-16, I-17, I-19, I-20, I-21, I-22, I-23, I-24, I-25, I-26.

In this test, for example, the following compounds from the preparation examples show an efficacy of 80% at an application rate of 160 µg/well: I-13, I-18.

*Myzus persicae*—Oral Test

| Solvent: | 100 parts by weight of acetone |
| --- | --- |

To produce a suitable preparation of active compound, 1 part by weight of active compound is dissolved using the specified parts by weight of solvent and made up with water until the desired concentration is attained.

50 µl of the active ingredient formulation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution through.

After 5 days, the efficacy in % is determined. 100% means that all the aphids have been killed; 0% means that no aphids have been killed.

In this test, for example, the following compounds from the preparation examples show an efficacy of 100% at an application rate of 4 ppm: I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-26.

*Myzus persicae*—Spray Test

| Solvent: | 78 parts by weight of acetone |
| --- | --- |
| | 1.5 parts by weight of dimethylformamide |
| Emulsifier: | alkylaryl polyglycol ether |

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-1, I-4, I-5, I-6, I-8, I-9, I-20.

In this test, for example, the following compounds from the preparation examples show an efficacy of 90% at an application rate of 100 g/ha: I-3, I-7, I-10, I-11, I-12, I-13, I-14, I-15, I-16, I-21, I-22.

In this test, for example, the following compounds from the preparation examples show an efficacy of 70% at an application rate of 100 g/ha: I-18.

*Phaedon cochleariae*—Spray Test

| Solvent: | 78.0 parts by weight of acetone |
| --- | --- |
| | 1.5 parts by weight of dimethylformamide |
| Emulsifier: | alkylaryl polyglycol ether |

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) are sprayed with an active compound formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: I-5, I-6, I-7, I-9, I-10, I-14.

*Spodoptera frugiperda*—Spray Test

| Solvent: | 78.0 parts by weight of acetone |
| --- | --- |
| | 1.5 parts by weight of dimethylformamide |
| Emulsifier: | alkylaryl polyglycol ether |

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Leaf discs of maize (*Zea mays*) are sprayed with an active compound formulation of the desired concentration and, after drying, populated with caterpillars of the fall armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: I-2, I-3, I-5, I-6, I-8, I-9, I-10, I-11, I-12, I-14, I-15, I-16, I-17, I-18, I-19, I-20, I-21, I-22, I-23, I-24, I-25, I-26.

*Tetranychus urticae*—Spray Test, OP-Resistant

| Solvent: | 78.0 parts by weight of acetone |
| --- | --- |
| | 1.5 parts by weight of dimethylformamide |
| Emulsifier: | alkylaryl polyglycol ether |

To produce a suitable active compound preparation, 1 part by weight of active compound is dissolved using the stated parts by weight of solvent and made up with water containing an emulsifier concentration of 1000 ppm until the desired concentration is attained. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound formulation of the desired concentration.

After 6 days, the efficacy in % is determined. 100% means that all the spider mites have been killed; 0% means that no spider mites have been killed.

In this test, for example, the following compounds from the preparation examples show an efficacy of 90% at an application rate of 20 g/ha: I-10.

The invention claimed is:
1. A compound of formula (I)

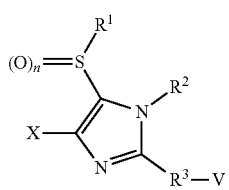

wherein
R¹ represents $(C_1-C_6)$alkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl or $(C_3-C_8)$cycloalkyl,
R² is hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, cyano$(C_3-C_8)$cycloalkyl, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkyl sulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl or $(C_1-C_6)$haloalkoxycarbonyl-$(C_1-C_6)$alkyl,
R³ represents aryl which is optionally mono- or polysubstituted by identical or different substituents or represents a saturated, partially saturated or heteroaromatic ring which is optionally mono- or polysubstituted by identical or different substituents, where at least one carbon atom is replaced by a heteroatom, which may in each case contain at least one carbonyl group and/or where possible substituents are in each case as follows: cyano, carboxyl, halogen, nitro, acetyl, hydroxy, amino, SCN, tri-$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkoxyimino, —N=C(H)—O$(C_1-C_6)$alkyl, —C(H)=N—O$(C_1-C_6)$alkyl, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkyl sulfonyl, $(C_1-C_6)$alkoxy-$(C_1-C_6)$alkylsulfonyl, $(C_1-C_6)$alkyl sulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkyl-aminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, V represents $(C_3-C_6)$cycloalkyl or aryl which are in each case optionally mono- or polysubstituted by identical or different substituents or represents a saturated, partially saturated or heteroaromatic ring which is optionally mono- or polysubstituted by identical or different substituents, where at least one carbon atom is replaced by a heteroatom, which may in each case contain at least one carbonyl group and/or where possible substituents are in each case as follows: cyano, carboxyl, halogen, nitro, acetyl, hydroxy, amino, SCN, tri-$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkoxyimino, —N=C(H)—O$(C_1-C_6)$alkyl, —C(H)=N—O$(C_1-C_6)$alkyl, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, di-$(C_1-C_6)$alkyl-aminocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di-$(C_1-C_6)$alkylamino, aminosulfonyl, $(C_1-C_6)$alkylaminosulfonyl, di-$(C_1-C_6)$alkylaminosulfonyl, $(C_1-C_6)$alkylsulfoximino, aminothiocarbonyl, $(C_1-C_6)$alkylaminothiocarbonyl, di-$(C_1-C_6)$alkylaminothiocarbonyl, $(C_3-C_8)$cycloalkylamino, $(C_1-C_6)$alkylcarbonylamino, X represents a heteroaromatic 9-membered fused bicyclic ring system from the series Q1 to Q6,

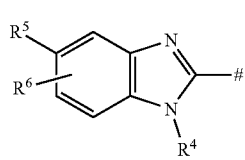

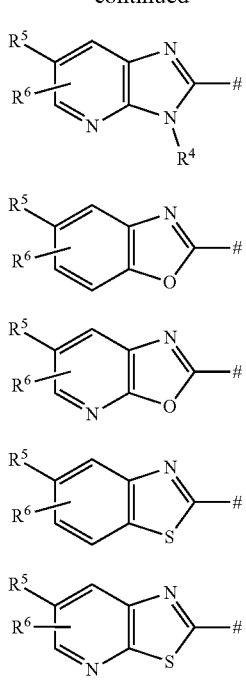

R⁴ represents hydrogen, (C₁-C₆)alkyl, (C₁-C₆)haloalkyl, (C₁-C₆)cyanoalkyl, (C₁-C₆)hydroxyalkyl, (C₁-C₆)alkoxy-(C₁-C₆)alkyl, (C₁-C₆)haloalkoxy-(C₁-C₆)alkyl, (C₂-C₆)alkenyl, (C₂-C₆)alkenyloxy-(C₁-C₆)alkyl, (C₂-C₆)haloalkenyloxy-(C₁-C₆)alkyl, (C₂-C₆)haloalkenyl, (C₂-C₆)cyanoalkenyl, (C₂-C₆)alkynyl, (C₂-C₆)haloalkynyl or (C₃-C₈)cycloalkyl, R⁵, R⁶ independently of one another represent hydrogen, cyano, halogen, (C₁-C₆)alkyl, (C₁-C₆)haloalkyl, (C₂-C₆)alkenyl, (C₂-C₆)haloalkenyl, (C₂-C₆)alkynyl, (C₂-C₆)haloalkynyl, (C₃-C₈)cycloalkyl, (C₃-C₈)cycloalkyl-(C₃-C₈)cycloalkyl, (C₁-C₆)alkyl-(C₃-C₈)cycloalkyl, (C₁-C₆)haloalkyl-(C₃-C₈)cycloalkyl, cyano-(C₃-C₈)cycloalkyl, halo(C₃-C₈)cycloalkyl, (C₁-C₆)alkoxy, (C₁-C₆)haloalkoxy, (C₁-C₆)alkoxyimino, (C₁-C₆)haloalkoxyimino, (C₁-C₆)alkylthio, (C₁-C₆)haloalkylthio, (C₁-C₆)alkylsulfinyl, (C₁-C₆)haloalkylsulfinyl, (C₁-C₆)alkylsulfonyl, (C₁-C₆)haloalkyl sulfonyl, (C₁-C₆)alkylsulfonyloxy, (C₁-C₆)haloalkylsulfonyloxy, (C₁-C₆)alkylcarbonyl, (C₁-C₆)haloalkylcarbonyl, aminocarbonyl, (C₁-C₆)alkylaminocarbonyl, di(C₁-C₆)alkylaminocarbonyl, (C₁-C₆)alkylsulfonylamino, (C₁-C₆)alkylamino, di(C₁-C₆)alkylamino, aminosulfonyl, (C₁-C₆)alkylaminosulfonyl or di(C₁-C₆)alkylaminosulfonyl, n represents 0, 1 or 2.

2. The compound according to claim 1, wherein

R¹ represents (C₁-C₄)alkyl, (C₁-C₄)cyanoalkyl, (C₁-C₄)alkoxy-(C₁-C₄)alkyl, (C₁-C₄)haloalkyl, (C₂-C₄)alkenyl, (C₂-C₄)haloalkenyl, (C₂-C₄)alkynyl, (C₂-C₄)haloalkynyl or (C₃-C₆)cycloalkyl, R² represents hydrogen, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₁-C₄)haloalkoxy-(C₁-C₄)alkyl, (C₃-C₆)cycloalkyl, (C₃-C₆)cycloalkyl-(C₃-C₆)cycloalkyl, (C₁-C₄)alkyl-(C₃-C₆)cycloalkyl, halo(C₃-C₆)cycloalkyl, cyano(C₃-C₆)cycloalkyl, (C₁-C₄)alkylthio-(C₁-C₄)alkyl, (C₁-C₄)haloalkylthio-(C₁-C₄)alkyl, (C₁-C₄)alkylsulfinyl-(C₁-C₄)alkyl, (C₁-C₄)haloalkylsulfinyl-(C₁-C₄)alkyl, (C₁-C₄)alkylsulfonyl-(C₁-C₄)alkyl or (C₁-C₄)haloalkylsulfonyl-(C₁-C₄)alkyl, R³ represents aryl which is optionally mono- or disubstituted by identical or different substituents or represents a saturated, partially saturated or heteroaromatic ring which is optionally mono- or disubstituted by identical or different substituents, where at least one carbon atom is replaced by a heteroatom from the group consisting of N, O and S, which may in each case contain at least one carbonyl group and/or where possible substituents are in each case as follows: cyano, halogen, nitro, acetyl, amino, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₃-C₆)cycloalkyl, (C₃-C₆)cycloalkyl-(C₃-C₆)cycloalkyl, (C₁-C₄)alkyl-(C₃-C₆)cycloalkyl, (C₁-C₄)alkoxy, (C₁-C₄)haloalkoxy, (C₁-C₄)cyanoalkoxy, (C₁-C₄)alkoxy-(C₁-C₄)alkoxy, (C₁-C₄)alkoxyimino, —N=C(H)—O(C₁-C₄)alkyl, —C(H)=N—O(C₁-C₄)alkyl, (C₁-C₄)haloalkyl-(C₁-C₄)alkoxyimino, (C₁-C₄)alkylthio, (C₁-C₄)haloalkylthio, (C₁-C₄)alkylthio-(C₁-C₄)alkyl, (C₁-C₄)alkylsulfinyl, (C₁-C₄)haloalkylsulfinyl, (C₁-C₄)alkylsulfinyl-(C₁-C₄)alkyl, (C₁-C₄)alkylsulfonyl, (C₁-C₄)haloalkylsulfonyl, (C₁-C₄)alkyl sulfonyl-(C₁-C₄)alkyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl, di(C₁-C₄)alkylaminosulfonyl, (C₁-C₄)alkylcarbonylamino, V represents (C₃-C₆)cycloalkyl or aryl which are in each case optionally mono- or disubstituted by identical or different substituents or represents a saturated, partially saturated or heteroaromatic ring which is optionally mono- or disubstituted by identical or different substituents, where at least one carbon atom is replaced by a heteroatom from the group consisting of N, O and S, which may in each case contain at least one carbonyl group and/or where possible substituents are in each case as follows: cyano, halogen, nitro, acetyl, amino, (C₁-C₄)alkyl, (C₁-C₄)haloalkyl, (C₁-C₄)cyanoalkyl, (C₁-C₄)hydroxyalkyl, (C₁-C₄)alkoxy-(C₁-C₄)alkyl, (C₂-C₄)alkenyl, (C₂-C₄)haloalkenyl, (C₂-C₄)cyanoalkenyl, (C₂-C₄)alkynyl, (C₂-C₄)haloalkynyl, (C₂-C₄)cyanoalkynyl, (C₃-C₆)cycloalkyl, (C₃-C₆)cycloalkyl-(C₃-C₆)cycloalkyl, (C₁-C₄)alkyl-(C₃-C₆)cycloalkyl, (C₁-C₄)alkoxy, (C₁-C₄)haloalkoxy, (C₁-C₄)cyanoalkoxy, (C₁-C₄)alkoxy-(C₁-C₄)alkoxy, (C₁-C₄)alkoxyimino, —N=C(H)—O(C₁-C₄)alkyl, —C(H)=N—O(C₁-C₄)alkyl, (C₁-C₄)haloalkyl-(C₁-C₄)alkoxyimino, (C₁-C₄)alkylthio, (C₁-C₄)haloalkylthio, (C₁-C₄)alkylthio-(C₁-C₄)alkyl, (C₁-C₄)alkyl sulfinyl, (C₁-C₄)haloalkylsulfinyl, (C₁-C₄)alkylsulfinyl-(C₁-C₄)alkyl, (C₁-C₄)alkyl sulfonyl, (C₁-C₄)haloalkylsulfonyl, (C₁-C₄)alkylsulfonyl-(C₁-C₄)alkyl, (C₁-C₄)alkylsulfonyloxy, (C₁-C₄)alkylcarbonyl, (C₁-C₄)haloalkylcarbonyl, aminocarbonyl, (C₁-C₄)alkylaminocarbonyl, di(C₁-C₄)alkylaminocarbonyl, (C₁-C₄)alkylsulfonylamino, (C₁-C₄)alkylamino, di(C₁-C₄)alkylamino, aminosulfonyl, (C₁-C₄)alkylaminosulfonyl, di(C₁-C₄)alkylaminosulfonyl, (C₁-C₄)alkylcarbonylamino, X represents a heteroaromatic 9-membered fused bicyclic ring system from the series Q1 to Q6, R⁴ represents hydrogen, (C₁-C₄)alkyl, (C₁-C₄)haloalkyl, (C₁-C₄)cyanoalkyl, (C₁-C₄)alkoxy-(C₁-C₄)alkyl, (C₁-C₄)haloalkoxy-(C₁-C₄)alkyl, (C₂-C₄)alkenyl, (C₂-C₄)haloalkenyl, (C₂-C₄)alkynyl, (C₂-C₄)haloalkynyl or (C₃-C₆)cycloalkyl, R⁵, R⁶ independently of one another represent hydrogen, cyano, halogen, (C₁-C₄)alkyl, (C₁-C₄)haloalkyl, (C₂-C₄)alkenyl, (C₂-C₄)haloalkenyl, (C₂-C₄)alkynyl, (C₂-C₄)haloalkynyl, (C₃-C₆)cycloalkyl, (C₃-C₆)cycloalkyl-(C₃-C₆)cycloalkyl, (C₁-C₄)alkyl-(C₃-C₆)cycloalkyl, (C₁-C₄)haloalkyl-(C₃-C₆)cycloalkyl, cyano(C₃-C₆)cycloalkyl, halo(C₃-C₆)cycloalkyl, (C₁-C₄)alkoxy, (C₁-C₄)haloalkoxy, (C₁-C₄)alkoxyimino, (C₁-C₄)haloalkoxyimino, (C₁-C₄)alkylthio, (C₁-C₄)haloalkylthio, (C₁-C₄)alkyl sulfinyl, (C₁-C₄)haloalkyl sulfinyl, (C₁-C₄)alkylsulfonyl, (C₁-C₄)haloalkylsulfonyl, (C₁-C₄)alkylsulfonyloxy, (C₁-C₄)haloalkylsulfonyloxy, (C₁-C₄)alkylcarbonyl or (C₁-C₄)haloalkylcarbonyl, n represents 0, 1 or 2.

3. The compound according to claim 1, wherein

R¹ represents (C₁-C₄)alkyl, (C₁-C₄)haloalkyl, (C₂-C₄)alkenyl, (C₂-C₄)haloalkenyl or (C₃-C₆)cycloalkyl, R² represents hydrogen, (C₁-C₄)alkyl, (C₁-C₄)haloalkyl, (C₃-C₆)cycloalkyl or halo(C₃-C₆)cycloalkyl, R³–V represents a 5- or 6-membered ring optionally mono- or disubstituted by identical or different substituents from the series U-1 to U-83, where possible substituents are in each case: cyano, halogen, (C₁-C₄)alkyl, (C₁-C₄)alkoxy or (C₁-C₄)haloalkoxy,

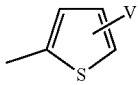
U-1

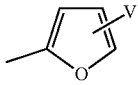
U-2

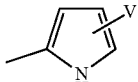
U-3

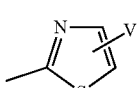
U-4

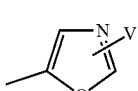
U-5

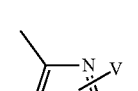
U-6

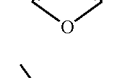
U-7

-continued

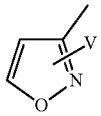
U-8

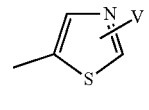
U-9

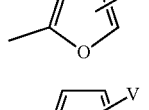
U-10

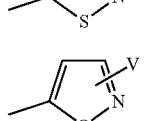
U-11

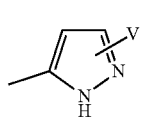
U-12

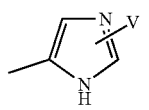
U-13

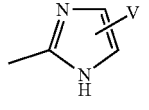
U-14

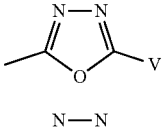
U-15

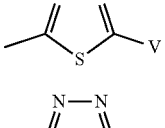
U-16

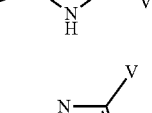
U-17

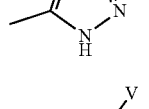
U-18

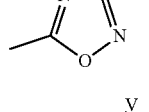
U-19

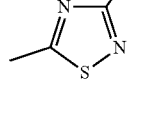
U-20

U-21

-continued
U-22 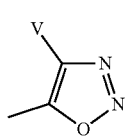
U-23 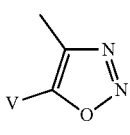
U-24 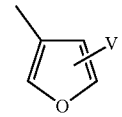
U-25 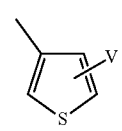
U-26 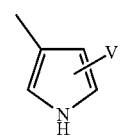
U-27 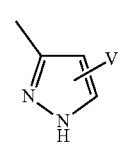
U-28 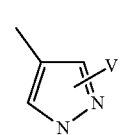
U-29 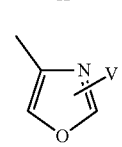
U-30 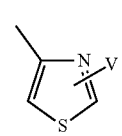
U-31 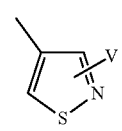
U-32 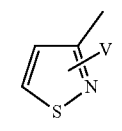
U-33 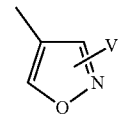
-continued
U-34 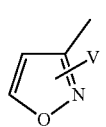
U-35 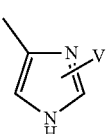
U-36 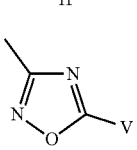
U-37 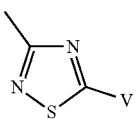
U-38 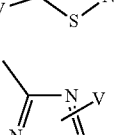
U-39 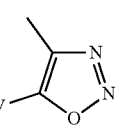
U-40 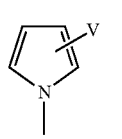
U-41 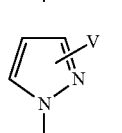
U-42 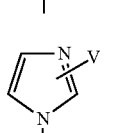
U-43 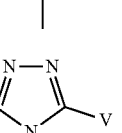
U-44 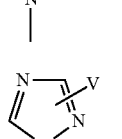
U-45 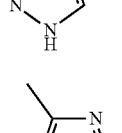

| | | | |
|---|---|---|---|
| 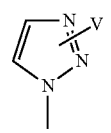 | U-46 | 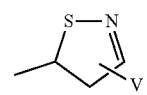 | U-58 |
| 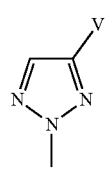 | U-47 | 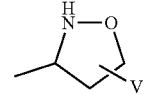 | U-59 |
| 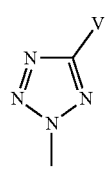 | U-48 | 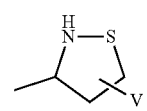 | U-60 |
| 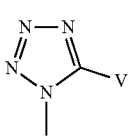 | U-49 | 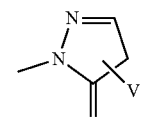 | U-61 |
| 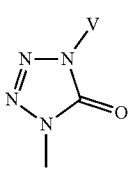 | U-50 | 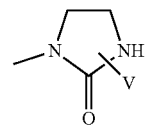 | U-62 |
| 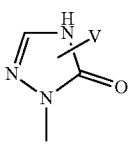 | U-51 | 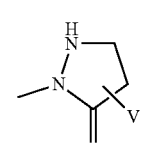 | U-63 |
| 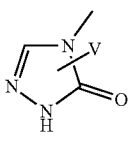 | U-52 | 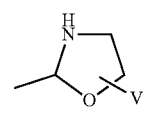 | U-64 |
| 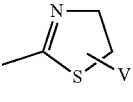 | U-53 | 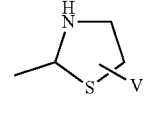 | U-65 |
| 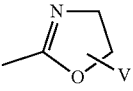 | U-54 | 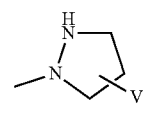 | U-66 |
| 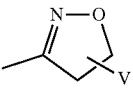 | U-55 | 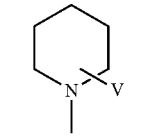 | U-67 |
| 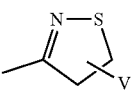 | U-56 | 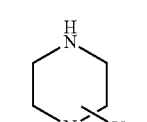 | U-68 |
| 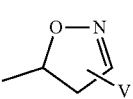 | U-57 | 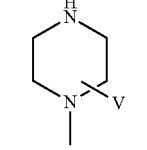 | U-69 |

U-70 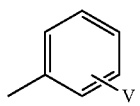
U-71 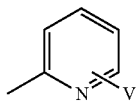
U-72 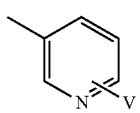
U-73 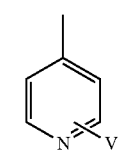
U-74 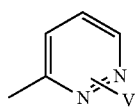
U-75 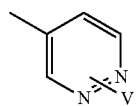
U-76 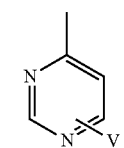
U-77 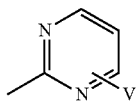
U-78 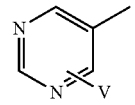
U-79 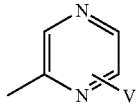
U-80 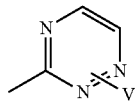
U-81 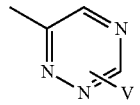
U-82 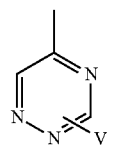
U-83 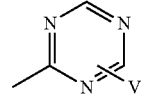
where
V represents a 3- to 6-membered ring optionally mono- or disubstituted by identical or different substituents from the series V-1 to V-105, where possible substituents are in each case: cyano, halogen, $(C_1\text{-}C_4)$alkyl, $(C_1\text{-}C_4)$alkoxy or $(C_1\text{-}C_4)$haloalkoxy,
V-1 
V-2 
V-3 
V-4 
V-5 
V-6 
V-7 
V-8 
V-9 
V-10 
V-11 

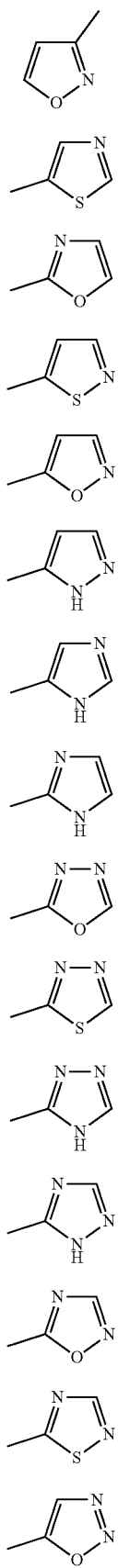
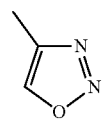
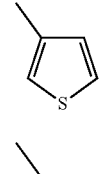

-continued
V-39 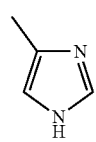
V-40 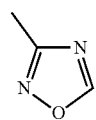
V-41 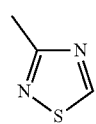
V-42 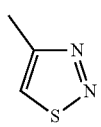
V-43 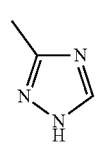
V-44 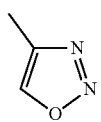
V-45 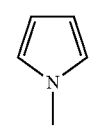
V-46 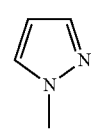
V-47 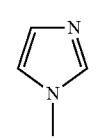
V-48 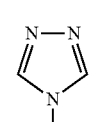
V-49 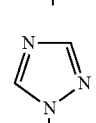
V-50 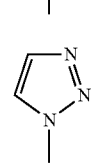
-continued
V-51 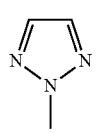
V-52 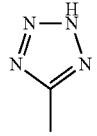
V-53 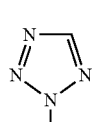
V-54 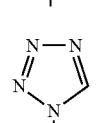
V-55 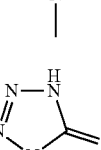
V-56 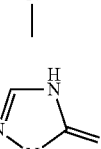
V-57 
V-58 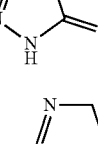
V-59 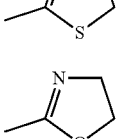
V-60 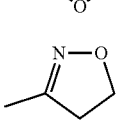
V-61 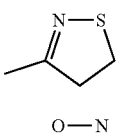
V-62 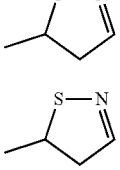
V-63

-continued
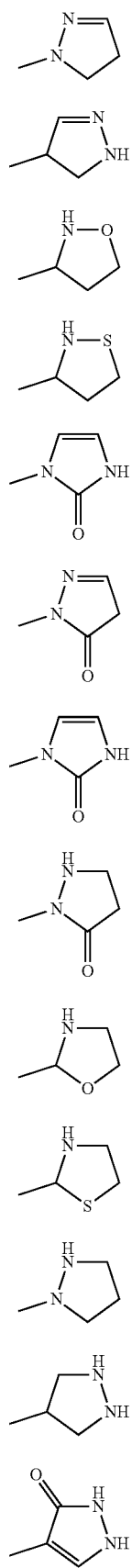
V-64
V-65
V-66
V-67
V-68
V-69
V-70
V-71
V-72
V-73
V-74
V-75
V-76
-continued
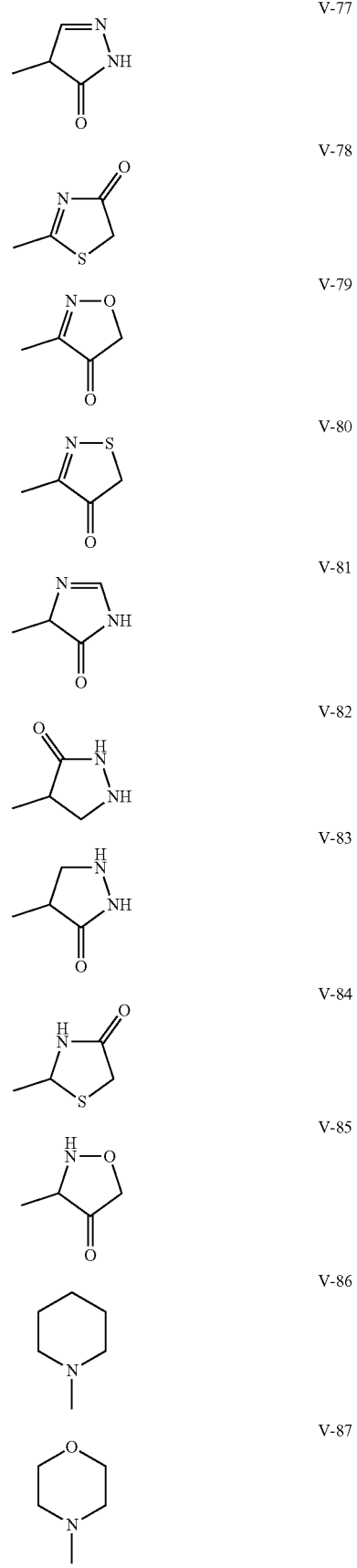
V-77
V-78
V-79
V-80
V-81
V-82
V-83
V-84
V-85
V-86
V-87

-continued

V-88
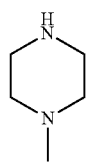

V-89
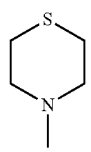

V-90
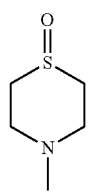

V-91
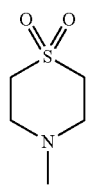

V-92
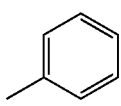

V-93
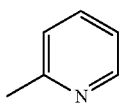

V-94
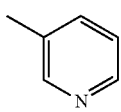

V-95
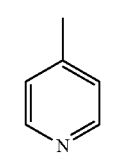

V-96
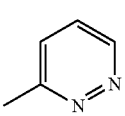

V-97
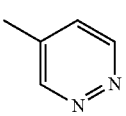

V-98
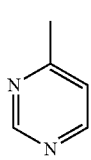

-continued

V-99
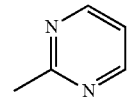

V-100
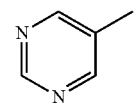

V-101
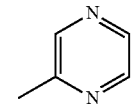

V-102
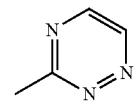

V-103
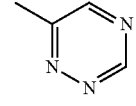

V-104
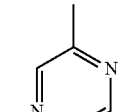

V-105
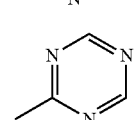

X represents a heteroaromatic 9-membered fused bicyclic ring system from the series Q1, Q2 and Q3, $R^4$ represents hydrogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_1-C_4)$alkoxy-$(C_1-C_4)$alkyl or $(C_3-C_6)$cycloalkyl, $R^5$ represents halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_1-C_4)$haloalkyl-$(C_3-C_6)$cycloalkyl, cyano-$(C_3-C_6)$cycloalkyl, halo-$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, $R^6$ represents hydrogen, cyano, halogen, $(C_1-C_4)$alkyl, $(C_1-C_4)$haloalkyl or $(C_3-C_6)$cycloalkyl, n represents 0, 1 or 2.

4. The compound according to claim 3, wherein $R^1$ represents methyl, ethyl, n-propyl, isopropyl, cyclopropyl, fluoromethyl, difluoromethyl, trifluoromethyl, fluoroethyl, difluoroethyl, trifluoroethyl, tetrafluoroethyl or pentafluoroethyl, $R^2$ represents hydrogen, methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R³–V represents an optionally monosubstituted 5- or 6-membered ring from the series U-1, U-2, U-3, U-4, U-5, U-6, U-7, U-8, U-9, U-10, U-11, U-12, U-13, U-14, U-15, U-24, U-25, U-26, U-27, U-28, U-29, U-30, U-31, U-32, U-33, U-34, U-35, U-41, U-42, U-43, U-44, U-45, U-46, U-47, U-51, U-52, U-53, U-54, U-55, U-56, U-57, U-58, U-61, U-62, U-68, U-69, U-70, U-71, U-72, U-73, U-74, U-75, U-76, U-77, U-78 or U-79, where possible substituents are in each case: cyano, fluorine, chlorine, bromine, methyl, ethyl, n-propyl, isopropyl, n-butyl, isobutyl, tert-butyl, methoxy or trifluoromethoxy,
where
V represents a 3- to 6-membered ring optionally mono- or disubstituted by identical or different substituents selected from cyano, fluorine, chlorine, bromine, methyl, ethyl, n-propyl, isopropyl, n-butyl, isobutyl, tert-butyl, methoxy or trifluoromethoxy, selected from V-1, V-2, V-3, V-4, V-5, V-6, V-7, V-8, V-9, V-10, V-11, V-12, V-13, V-14, V-15, V-16, V-17, V-18, V-19, V-28, V-29, V-30, V-31, V-32, V-33, V-34, V-35, V-36, V-37, V-38, V-39, V-45, V-46, V-47, V-48, V-49, V-50, V-51, V-58, V-59, V-62, V-63, V-86, V-87, V-88, V-89, V-90, V-91, V-92, V-93, V-94, V-95, V-96, V-97, V-98, V-99, V-100 or V-101,
X represents a heteroaromatic ring system from the series Q2 or Q3,
R⁴ represents methyl, ethyl, n-propyl, isopropyl, n-butyl, isobutyl, tert-butyl, methoxymethyl or methoxyethyl,
R⁵ represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl,
R⁶ represents hydrogen, cyano, methyl, trifluoromethyl, fluorine or chlorine,
n represents 0, 1 or 2.
5. The compound according to claim 3, wherein
R¹ represents ethyl,
R² represents methyl,
R³–V represents a ring, optionally monosubstituted by cyano or bromine, from the series U-1, U-13, U-28, U-41, U-42, U-57, U-70, U-71 and U-72,
where
V represents a ring, optionally monosubstituted by cyano, fluorine or chlorine, from the series V-1, V-5, V-87, V-92, V-93 and V-94,
X represents a heteroaromatic ring system from the series Q2,
R⁴ represents methyl,
R⁵ represents trifluoromethyl or pentafluoroethyl,
R⁶ represents hydrogen,
n represents 2.
6. The compound according to claim 1, wherein the compound has a structure below:

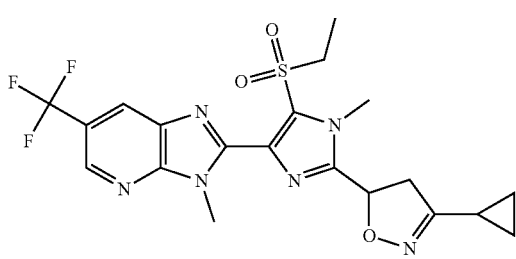

-continued

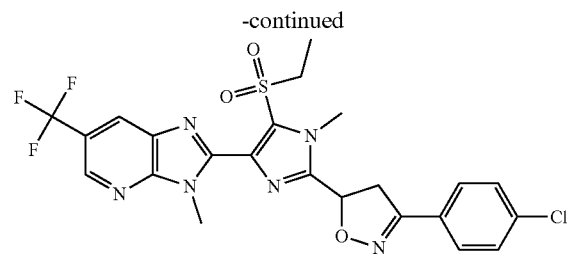

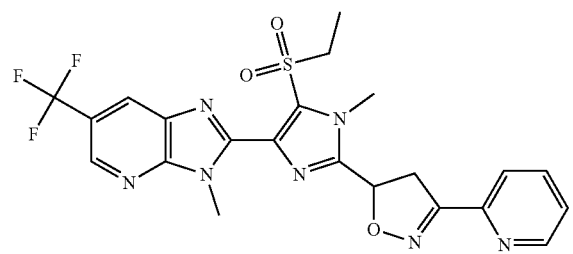

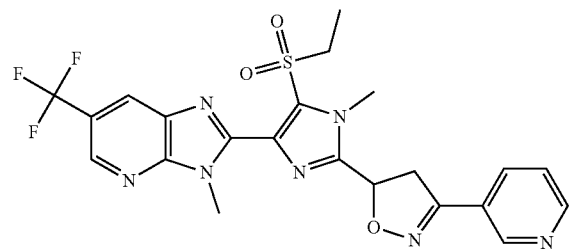

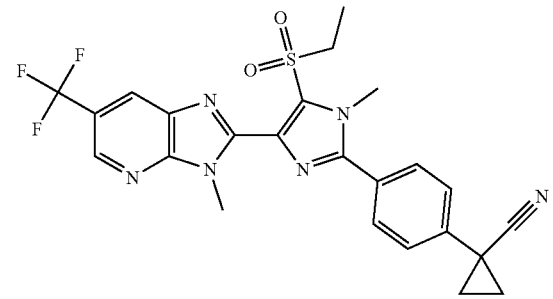

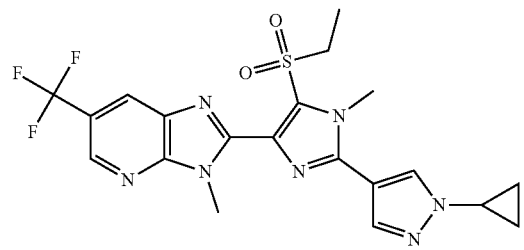

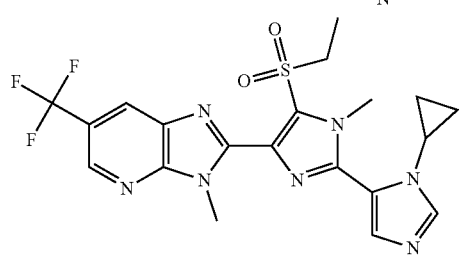

117
-continued
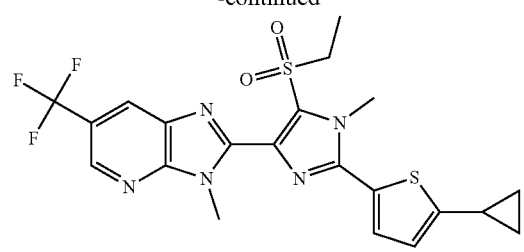
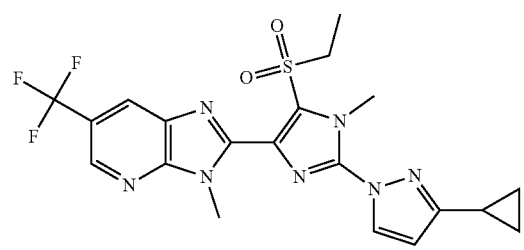
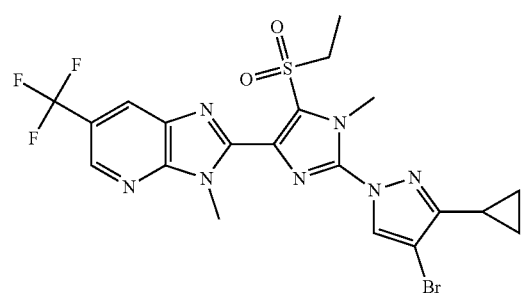
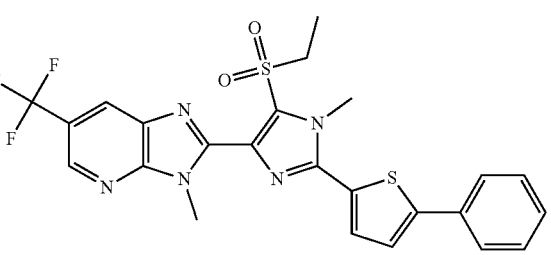
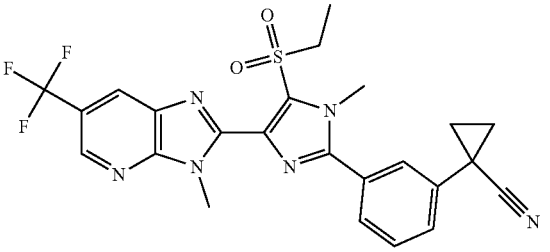
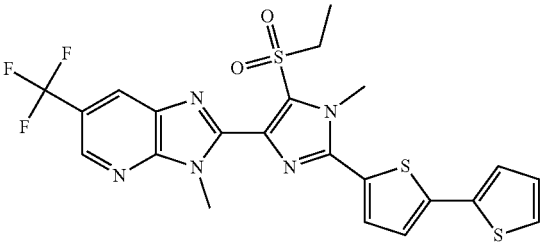
118
-continued
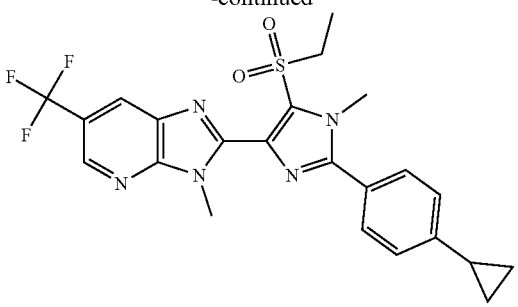
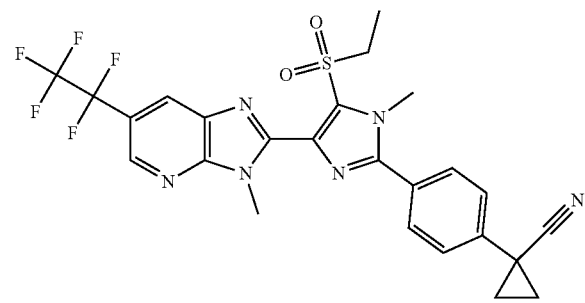 [SMILES: CCS(=O)(=O)c1c(-c2nc3cc(C(F)(F)C(F)(F)F)cnc3n2C)nc(-c2ccc(C3(C#N)CC3)cc2)n1C]
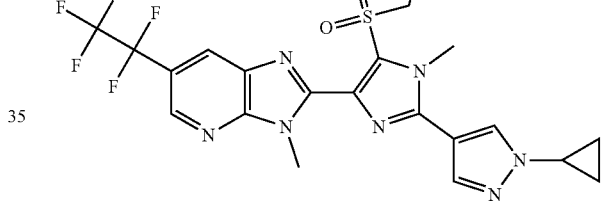
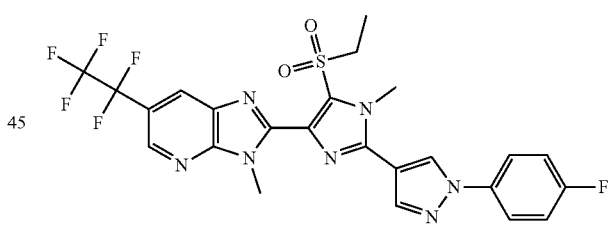
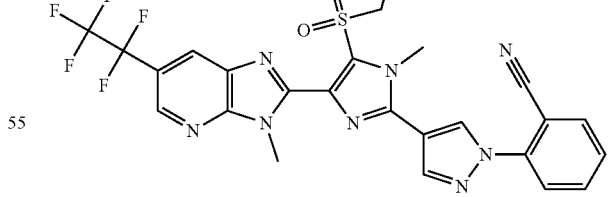
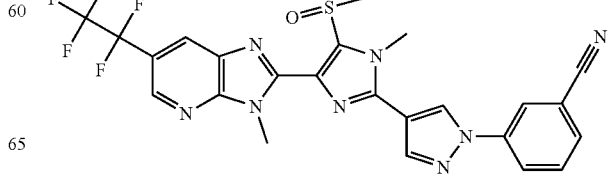

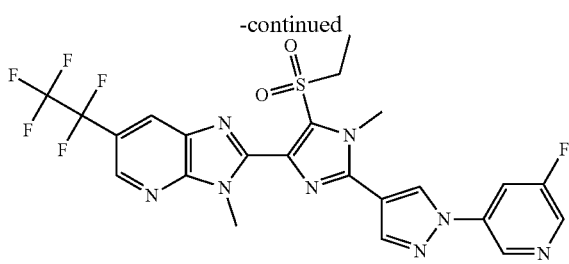
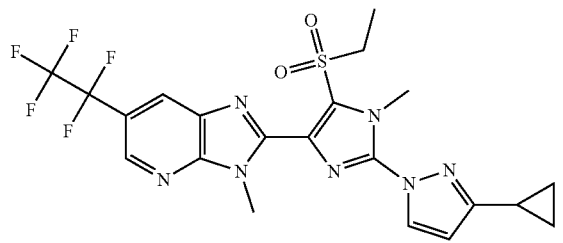
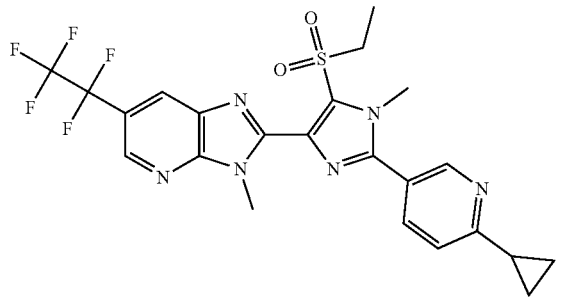
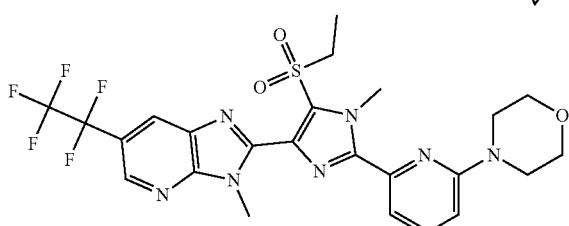
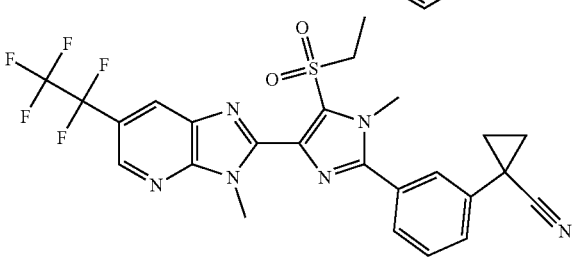
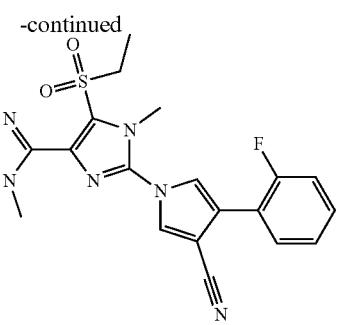
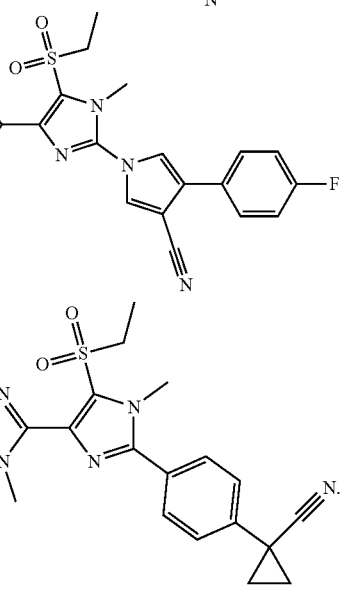

7. An agrochemical formulation comprising the compound according to claim 1 and one or more extenders and/or surfactants.

8. The agrochemical formulation according to claim 7, additionally comprising a further agrochemical active compound.

9. A method for controlling one or more animal pests, comprising allowing the compound according to claim 1 or an agrochemical formulation thereof to act on the animal pests and/or a habitat thereof.

10. A product comprising the compound according to claim 1 or an agrochemical formulation thereof for controlling one or more animal pests.

* * * * *